US010857155B2

(12) United States Patent
Chan et al.

(10) Patent No.: US 10,857,155 B2
(45) Date of Patent: Dec. 8, 2020

(54) COMPOUNDS TARGETING PROTEINS, COMPOSITIONS, METHODS, AND USES THEREOF

(71) Applicant: BioTheryX, Inc., Chappaqua, NY (US)

(72) Inventors: Kyle W. H. Chan, San Diego, CA (US); Paul E. Erdman, San Diego, CA (US); Leah Fung, San Diego, CA (US); Frank Mercurio, Rancho Santa Fe, CA (US); Robert Sullivan, Vista, CA (US)

(73) Assignee: BioTheryX, Inc., Chappaqua, NY (US)

( * ) Notice: Subject to any disclaimer, the term of this patent is extended or adjusted under 35 U.S.C. 154(b) by 0 days.

(21) Appl. No.: 16/539,933

(22) Filed: Aug. 13, 2019

(65) Prior Publication Data

US 2019/0365775 A1 Dec. 5, 2019

Related U.S. Application Data

(62) Division of application No. 15/916,752, filed on Mar. 9, 2018, now Pat. No. 10,406,165.

(60) Provisional application No. 62/470,996, filed on Mar. 14, 2017.

(51) Int. Cl.
A61K 31/55 (2006.01)
A61P 35/02 (2006.01)
A61P 35/00 (2006.01)
C07D 403/04 (2006.01)

(52) U.S. Cl.
CPC .............. A61K 31/55 (2013.01); A61P 35/00 (2018.01); A61P 35/02 (2018.01); C07D 403/04 (2013.01)

(58) Field of Classification Search
None
See application file for complete search history.

(56) References Cited

U.S. PATENT DOCUMENTS

| 2009/0142297 | A1 | 6/2009 | Muller et al. |
| 2015/0374678 | A1 | 12/2015 | Chamberlain et al. |
| 2016/0362397 | A1* | 12/2016 | Chan ........................ A61P 21/00 |
| 2018/0264000 | A1 | 9/2018 | Chan |

FOREIGN PATENT DOCUMENTS

| JP | 2000-159761 | 6/2000 |
| WO | WO 10/053732 | 5/2010 |
| WO | WO 16/064935 | 4/2016 |
| WO | WO 16/191178 | 12/2016 |

OTHER PUBLICATIONS

Amit et al., 2002, Axin-mediated CKI phosphorylation of β-catenin at Ser 45: a molecular switch for the Wnt pathway, Genes & Development, 16:1066-1076.
Brenner et al., 2008, The protective role of melanin against UV damage in human skin, Photochem. Photobiol., 84:539-549.
Brito et al., 2005, Polyglycine expansions in eRF3/GSPT1 are associated with gastric cancer susceptibility, Carcinogenesis, 26(12):2046-2049.
Chauvin et al., Aug. 2007, Human eukaryotic release factor 3a depletion causes cell cycle arrest at $G_1$ phase through inhibition of the mTOR pathway, Mol. Cell. Bio., 27(16):5619-5629.
Cheong et al., 2011, Casein kinase 1: complexity in the family, J. Biochem. Cell Biol., 43:465-469.
Costin et al., 2007, Human skin pigmentation: melanocytes modulate skin color in response to stress, Faseb J., 21(4):976-994.
Cui et al., Mar. 9, 2007, Central role of p53 in the suntan response and pathologic hyperpigmentation, Cell, 128:853-864.
D'Orazio et al., Sep. 21, 2006, Topical drug rescue strategy and skin protection based on the role of Mc1r in UV-induced tanning, Nature, 443:340-344.
Eger et al., 1990, Arzneimittel-Forschung, 40(10):1073-1075.
Elyada et al., Feb. 17, 2011, CK1α ablation highlights a critical role for p53 in invasiveness control, Nature, 470:409-413.
Hashimoto et al., 2012, Translation termination factor eRF3 is targeted for caspase-mediated proteolytic cleavage and degradation during DNA damage-induced apoptosis, Apoptosis, 17:1287-1299.
Huart et al., Nov. 20, 2009, CK1α plays a central role in mediating MDM2 control of p53 and E2F-1 protein stability, J. Biol. Chem., 284(47):32384-32394.
Hyter et al., Mar. 2013, Endothelin-1 is a transcriptional target of p53 in epidermal keratinocytes and regulates UV induced melanocyte homeostasis, Pigment. Cell Melanoma Res., 26(2):247-258.
Ishii et al., Jan. 27, 2017, A novel Rac1-GSPT1 signaling pathway controls astrogliosis following central nervous system injury, J. Biol. Chem., 292(4):1240-1250.
Kadekaro et al., 2003, Cutaneous photobiology. The melanocyte vs. the sun: who will win the final round? Pigment Cell Res., 16:434-447.
Kondo, 1999, The roles of keratinocyte-derived cytokines in the epidermis and their possible responses to UVA-irradiation, J. Invest. Dermatol. Symp. Proc., 4:177-183.
Levine et al., Oct. 2009, The first 30 years of p53: growing ever more complex, Nat. Rev. Cancer, 9(10):749-758.
Li et. al., Jan. 2014, eRF3b, a biomarker for hepatocellular carcinoma, influences cell cycle and phosphoralation status of 4E-BP1, PLOS One, 9(1):e86371.
Malta-Vacas et al., 2009, Differential expression of GSPT1 $GGC_n$ alleles in cancer, Canc. Geneti. Cytogen., 195:132-142.
Matyskiela et al., Jul. 14, 2016, A novel cereblon modulator recruits GSPT1 to the $CRL4^{CRBN}$ ubiquitin ligase, Nature, 535:252-257 with additional material.

(Continued)

Primary Examiner — Dennis Heyer
(74) Attorney, Agent, or Firm — Lin Yu, Esq.; Juniv LLP

(57) ABSTRACT

The present invention provides modulators of protein function, to restore protein homeostasis, including GSPT1 activity. The invention provides methods of modulating protein-mediated diseases, such as GSPT1-mediated diseases, disorders, conditions, or responses. Compositions are also provided. Methods of treatment, amelioration, or prevention of protein-mediated diseases, disorders, and conditions, such as GSPT1-mediated diseases, disorders, and conditions, including cancer and astrogliosis.

9 Claims, 5 Drawing Sheets

(56) References Cited

OTHER PUBLICATIONS

Miri et al., 2012, GGCn polymorphism of eRF3a/GSPT1 gene and breast cancer susceptibility, Med. Oncol., 29:1581-1585.
Mitra et al., Nov. 15, 2012, A UV-independent pathway to melanoma carcinogenesis in the redhair-fairskin background, Nature, 491:449-453.
Murase et al., Feb. 13, 2009, The essential role of p53 in hyperpigmentation of the skin via regulation of paracrine melanogenic cytokine receptor signaling, J. Biol. Chem., 284(7):4343-4353.
Nasti et al., 1015, MC1R, eumelanin and pheomelanin: their role in determining the susceptibility to skin cancer, Photochem. Photobiol., 91:188-200.
Natarajan et al., Jul. 2014, Multifaceted pathways protect human skin from UV radiation, Nat. Chem. Biol., 10:542-551.
Ogmundsdottir et al., 2014, Selection, p53, and pigmentation, Pigment Cell Melanoma Res., 27:154-155.
Prota, 1992, The role of peroxidase in melanogenesis revisited, Pigment. Cell Res., Suppl. 2:25-31.
Schittek et al., 2014 Biological functions of casein kinase 1 isoforms and putative roles in tumorigenesis, Mol. Cancer., 13:231.
Schneider et al., Oct. 13, 2014, Role of casein kinase 1A1 in the biology and targeted therapy of del(5q) MDS, Cancer Cell, 26:509-520.
Slominski et al., 2004, Melanin pigmentation in mammalian skin and its hormonal regulation, Physiol. Rev., 84:1155-1228.
Stern, Mar. 2010, Prevalence of a history of skin cancer in 2007, Arch Dermatol., 146(3):279-282.
Thody et al., 1991, Pheomelanin as well as eumelanin is present in human epidermis, J. Invest. Dermatol., 97:340-344.
Wright et al., 2007, Newer potential biomarkers in prostate cancer, Rev. Urol., 9(4):207-213.
International Search Report and Written Opinion dated May 11, 2018 in application No. PCT/2018/021704.

\* cited by examiner

COMPOUNDS TARGETING PROTEINS, COMPOSITIONS, METHODS, AND USES THEREOF

CROSS-REFERENCE TO RELATED APPLICATION

This application is a division of U.S. patent application Ser. No. 15/916,752, filed Mar. 9, 2018, which claims the benefit of priority to U.S. Provisional Patent Application No. 62/470,996 filed Mar. 14, 2017, each of which is incorporated by reference herein in its entirety.

BACKGROUND OF THE INVENTION

Field of the Invention

Compounds, methods of making such compounds, pharmaceutical compositions and medicaments comprising such compounds, and methods of using such compounds to treat, prevent or diagnose diseases, disorders, or conditions associated with protein malfunction are provided.

Description of the Related Technology

Aberrant protein function, and/or protein imbalance is a hallmark of many disease states. For example, protein synthesis, cell growth, and cell proliferation are each strictly regulated processes, both spatially and temporally. Misregulation of these processes may contribute to uncontrolled cell growth, proliferation, and migration, leading to cancer.

For example, the translation termination factor GSPT1 (eRF3a) mediates stop codon recognition and facilitates release of a nascent peptide from the ribosome. In addition to its role in translation termination, GSPT1 is also involved in several other critical cellular processes, such as cell cycle regulation, cytoskeleton organization and apoptosis. GSPT1 has been implicated as an oncogenic driver of several different cancer types, including breast cancer, hepatocellular carcinoma, gastric cancer, and prostate cancer. See, e.g., Brito, et al., *Carcinogenesis*, Vol. 26, No. 12, pp. 2046-49 (2005); Brito, et al., *Canc. Genet. Cyto.*, Vol. 195, pp. 132-42 (2009); Tavassoli, et al., *Med. Oncol.*, Vol. 29, pp. 1581-85 (2011); Wright and Lange, *Rev. Urol.*, Vol. 9, No. 4, pp. 207-213 (2007); Hoshino, et al., *Apoptosis*, Vol. 17, pp. 1287-99 (2012); Liu, et. al., *PLOS One*, Vol. 9, No. 1, e86371 (2014); and Jean-Jean, et al., *Mol. Cell. Bio.*, Vol. 27, No. 16, pp. 5619-29 (2007). GSPT1 also contributes to glial scar formation and astrogliosis after a central nervous system (CNS) injury. See, e.g., Ishii et al., *J. Biol. Chem.*, Vol. 292, No. 4, pp. 1240-50 (2017).

Similarly, the functioning of the immune system is finely balanced by the activities of pro-inflammatory and anti-inflammatory mediators or cytokines. Some cytokines promote inflammation (pro-inflammatory cytokines), whereas other cytokines suppress the activity of the pro-inflammatory cytokines (anti-inflammatory cytokines). For example, IL-4, IL-10, and IL-13 are potent activators of B lymphocytes, and also act as anti-inflammatory agents. They are anti-inflammatory cytokines by virtue of their ability to suppress genes for pro-inflammatory cytokines such as IL-1, TNF, and chemokines.

Unregulated activities of these mediators can lead to the development of serious inflammatory conditions. For example, autoimmune diseases arise when immune system cells (lymphocytes, macrophages) become sensitized against the "self." Lymphocytes, as well as macrophages, are usually under control in this system. However, a misdirection of the system toward the body's own tissues may happen in response to still unexplained triggers. One hypothesis is that lymphocytes recognize an antigen which mimics the "self" and a cascade of activation of different components of the immune system takes place, ultimately leading to tissue destruction. Genetic predisposition has also been postulated to be responsible for autoimmune disorders.

Tumor necrosis factor-alpha (TNF-alpha) and interleukin-1 (IL-1) are pro-inflammatory cytokines that mediate inflammatory responses associated with infectious agents and other cellular stresses. Overproduction of these cytokines is believed to underlie the progression of many inflammatory diseases including rheumatoid arthritis (RA), Crohn's disease, inflammatory bowel disease, multiple sclerosis, endotoxin shock, osteoporosis, Alzheimer's disease, congestive heart failure, and psoriasis among others.

Recent data from clinical trials support the use of protein antagonists of cytokines, for example soluble TNF-alpha receptor fusion protein (etanercept) or the monoclonal TNF-alpha antibody (infliximab), for the treatment of rheumatoid arthritis, Crohn's disease, juvenile chronic arthritis and psoriatic arthritis. Thus, the reduction of pro-inflammatory cytokines such as TNF-alpha and interleukin-1 (IL-I) has become an accepted therapeutic approach for potential drug intervention in these conditions.

Moreover, IL-2 is now FDA approved for the treatment of renal cancer and melanoma patients, with durable, complete remissions achieved with IL-2 up to 148 months. However, the short half-life of IL-2 in serum requires that large amounts of IL-2 be injected to achieve therapeutic levels. Many attempts have been made to minimize side effects of systemic IL-2 treatment, for example, introducing IL-2 directly into the tumor, though this complicates treatment, and has largely been unsuccessful.

Local delivery of cytokines is appealing compared to systemic delivery for a variety of reasons. It takes advantage of the natural biology of cytokines that have evolved to act locally in a paracrine or autocrine fashion. Local expression also dramatically minimizes many of the side effects of systemic delivery of cytokines. Thus, compounds and methods to increase local expression of IL-2 would be better tolerated than high dose IL-2 treatment, which would expand therapeutic utility of strategies that increase IL-2.

Additional therapeutic targets include several candidate genes involved in apoptosis and cell survival, including the zinc-finger transcription factors aiolos, helios, and ikaros. These proteins are transcription factors whose expression is restricted to lymphoid lineages. For example, aiolos binds to the Bcl-2 promoter, and also interacts with the Bcl-2 and Bcl-XL proteins to promote cell survival. Upregulation of aiolos expression, for example, can reduce apoptosis of HIV-1 infected cells.

Likewise, expression of aiolos in lung and breast cancers predicts significantly reduced patient survival. Aiolos decreases expression of a large set of adhesion-related genes, disrupting cell-cell and cell-matrix interactions, facilitating metastasis. Aiolos may also function as an epigenetic driver of lymphocyte mimicry in certain metastatic epithelial cancers. Similarly, aberrant ikaros and helios expression may promote Bcl-XL expression, driving the development of hematopoietic malignancies. Thus, downregulation of aiolos, ikaros, and/or helios may reduce or eliminate metastasis.

Furthermore, Casein kinase 1α (CK1α) is a component of the β-catenin-degradation complex and a critical regulator of the Wnt signaling pathway, and its ablation induces both Wnt and p53 activation. Schittek and Sinnberg, *Mol. Cancer.* 2014, 13, 231; Cheong and Virshup, *J. Biochem. Cell Biol.* 2011, 43, 465-469; Elyada et al., *Nature* 2011, 470, 409-413. CK1α phosphorylates β-catenin, which is subsequently further phosphorylated by GSK-3P3. This destabilizes β-catenin and marks the protein for ubiquitination and proteasomal degradation. Thus, CK1α functions as a molecular switch for the Wnt pathway. Amit et al., *Genes Dev.* 2002, 16, 1066-1076. CK1α is critical for embryogenesis and plays an important role in tissue development and response to DNA damage, at least partly coordinated with p53. Elyada et al., *Nature* 2011, 470, 409-413; Schneider et al., *Cancer Cell* 2014, 26, 509-520. Levine and Oren, *Nat. Rev. Cancer* 2009, 9, 749-758.

Indeed, CK1α also phosphorylates p53, which inhibits binding to MDM2 (a p53 inhibitor) and stabilizes p53's binding interactions with the transcriptional machinery. Huart, et al., *J. Biol. Chem.* 2009, 284, 32384-32394. Thus, inhibiting CK1α activity increases cellular levels of p53. This is of particular importance for skin cancer, which has killed more people since 1980 than all other types of cancer combined. Stern, *Arch Dermatol.* 2010, 146, 279-282.

In the skin, p53 also acts as a central player against UV damage via the p53/POMC/α-MSH/MC1R/MITF skin tanning pathway and through the DNA repair/cell cycle arrest/apoptotic pathway. Cui et al., *Cell* 2007, 128, 853-864; Ogmundsdottir and Steingrimsson, *Pigment. Melanoma Res.* 2014, 27, 154-155. UV radiation can injure the skin both by indirect cellular damage via the generation of reactive oxygen species and by direct damage to the structure of DNA. This damage may cause a sunburn reaction and ultimately the development of skin cancers. Keratinocytes in the epidermis are sensitive to UV radiation and are the major responders in the skin. Upon exposure to UV radiation, keratinocytes produce various paracrine factors (for example, α-melanocyte stimulating hormone (α-MSH), adrenocorticosteroid hormone (ACTH), endothelin-1 (Edn1) and Kit) that activate adjacent melanocytes to increase melanin synthesis. Natarajan et al., *Nat. Chem. Biol.* 2014, 10, 542-551; Kondo, *J. Invest. Dermatol. Symp. Proc.* 1999, 4, 177-183; Costin, *FASEB J.* 2007, 21, 976-994; Cui et al., *Cell* 2007, 128, 853-864; Nasti, *Photochem. Photobiol.* 2015, 91, 188-200; Slominski et al., *Physiol. Rev.* 2004, 84, 1155-1228; Murase et al., *J. Biol. Chem.* 2009, 284, 4343-4353; Hyter et al., *Pigment. Cell Melanoma Res.* 2013, 26, 247-258; D'Orazio et al., *Nature* 2006, 443, 340-344. In particular, p53 promotes UV-induced skin pigmentation by stimulating the transcription of a melanogenic cytokine, POMC (pro-opiomelanocortin), in keratinocytes.

Skin hyperpigmentation, from the increased synthesis of melanin in melanocytes followed by the distribution of melanin to neighboring keratinocytes, is one of the biological responses to exposure to UV radiation. Melanin acts as a natural sunscreen that directly protects against UV and visible light radiation from penetrating to deep skin layers, where proliferating cells reside, as well as acting as a potent antioxidant and free-radical scavenger. Kadekaro et al., *Pigment Cell Res.* 2003, 16, 434-447. Individuals with darker skin generally have a reduced incidence of UV-induced skin cancers, whereas individuals with lighter skin are more prone to UV-induced damage and tumor formation and have weak tanning responses. Brenner, et al., *Photochem. Photobiol.* 2008, 84, 539-549.

Melanocytes produce two distinct types of melanin pigments: black-brown eumelanin that is prevalent in individuals with black and/or brown hair, and yellow-reddish pheomelanin that is primarily produced in individuals with red hair and freckles. Costin and Hearing, *FASEB J.* 2007, 21, 976-994; Slominski et al., *Physiol. Rev.* 2004, 84, 1155-1228; Prota, *Pigment. Cell Res.* 1992, Suppl. 2, 25-31. Pheomelanin is also produced in the skin of individuals that don't have red hair and freckles. Thody et al., *J. Invest. Dermatol.* 1991, 97, 340-344. The beneficial effects of melanin are mainly due to the presence of eumelanin that absorbs most of the UV and scavenges the UV-generated free radicals, whereas pheomelanin is known to be carcinogenic. Brenner, et al.; Mitra et al., *Nature* 2012, 491, 449-453.

In some instances, a protein malfunction is not a direct result of protein over- or under-expression, or alterations to the protein's sequence and structure. Rather, the malfunction may simply be the inability of a wild-type protein, with normal function and expression levels, to (for example) combat a growing tumor. Accordingly, compounds that modulate protein function in both normal proteins and directly malfunctioning proteins, as well as restore protein homeostasis, are necessary for the treatment and prevention of disease.

SUMMARY OF THE INVENTION

The compounds disclosed in the present application have been discovered to exert surprising and unexpected biological effects. In particular, the compounds disclosed in the present application modulate protein levels to restore protein homeostasis.

Some embodiments provide a compound of Formula (I):

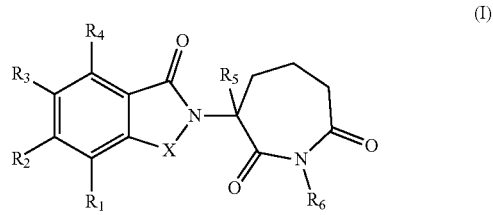

or a pharmaceutically acceptable salt or solvate thereof.

In some embodiments, $R_1$, $R_2$, $R_3$, and $R_4$, are each independently selected from the group consisting of H, deuterium, $-NH_2$, $-NHR_7$, $NR_7R_7$, halogen, cyano, nitro, an optionally substituted $C_1$ to $C_6$ alkoxy, an optionally substituted $C_1$ to $C_6$ alkyl,

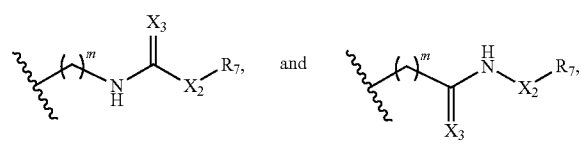

wherein at least one of $R_1$, $R_2$, $R_3$, and $R_4$ is

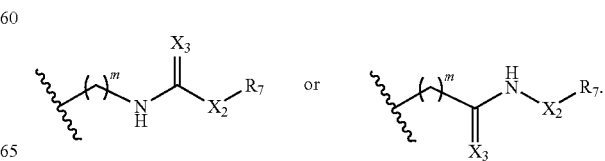

In some embodiments, $R_5$ is selected from the group consisting of H, deuterium, an optionally substituted $C_1$ to $C_6$ alkyl, and halogen. In some embodiments, $R_6$ is selected from the group consisting of H, deuterium, an optionally substituted $C_1$ to $C_6$ alkyl, and an optionally substituted $C_2$ to $C_6$ alkenyl. In some embodiments, X is selected from the group consisting of $CH_2$, $(CH_2)_2$, $CH(R_6)$, and C=O. In some embodiments, $X_2$ is selected from the group consisting of $(CH_2)_n$, $(CD_2)_n$, $(CF_2)_n$, C=O, NH, N-(an optionally substituted $C_1$ to $C_6$ alkyl), $[(CH_2)_p—NH—(CH_2)_q]_t$, and $[(CH_2)_p—O—(CH_2)_q]_t$. In some embodiments, $X_3$ is selected from the group consisting of NH, O, and S.

In some embodiments, m is 1, 2, 3, 4, or 5. In some embodiments, n is 0, 1, 2, 3, 4, 5, 6, 7, 8, 9, or 10. In some embodiments, p and q are independently 0, 1, 2, 3, 4, 5, or 6. In some embodiments, t is 0, 1, 2, 3, or 4.

In some embodiments, $R_7$ is selected from the group consisting of an optionally substituted $C_3$ to $C_{10}$ cycloalkyl, an optionally substituted $C_6$ to $C_{10}$ aryl, an optionally substituted 5 to 10-membered heteroaryl, an optionally substituted 3 to 10-membered heterocyclyl, and an optionally substituted $C_1$ to $C_{10}$ alkyl.

In some embodiments, $R^1$ is

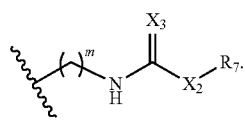

In some embodiments, $R^2$ is

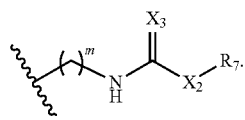

In some embodiments, $R^1$ is

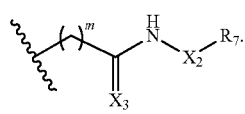

In some embodiments, $R^2$ is

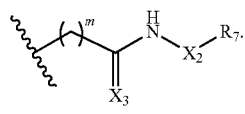

In some embodiments, when any of $R_1$, $R_2$, $R_3$, and $R_4$ is

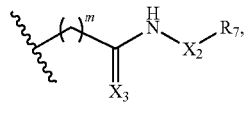

then $X^2$ is $(CH_2)_n$, $(CD_2)_n$, $(CF_2)_n$, C=O, $[(CH_2)_p—NH—(CH_2)_q]_t$, and $[(CH_2)_p—O—(CH_2)_q]_t$. In some embodiments, when any of $R_1$, $R_2$, $R_3$, and $R_4$ is

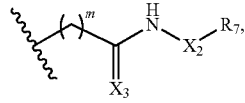

then $X^2$ is not NH or N-(an optionally substituted $C_1$ to $C_6$ alkyl).

In some embodiments, m is 1, 2, 3, or 4. In some embodiments, m is 1. In some embodiments, m is 2. In some embodiments, m is 3. In some embodiments, m is 4.

In some embodiments, $X_3$ is NH. In some embodiments, $X_3$ is O. In some embodiments, $X_3$ is S. In some embodiments, $X_2$ is selected from the group consisting of $(CH_2)_n$, C=O, $[(CH_2)_p—NH—(CH_2)_q]_t$, and $[(CH_2)_p—O—(CH_2)_q]_t$. In some embodiments, $X_2$ is $(CH_2)_n$.

In some embodiments, n is 0, 1, 2, or 3. In some embodiments, n is 0. In some embodiments, n is 1. In some embodiments, n is 2. In some embodiments, n is 3. In some embodiments, p and q are independently 0, 1, 2, or 3. In some embodiments, p and q are independently 2 or 3. In some embodiments, p and q are independently 0, 1, or 2. In some embodiments, p and q are independently 1 or 2. In some embodiments, t is 0, 1, 2, or 3. In some embodiments, t is 1. In some embodiments, t is 2. In some embodiments, t is 3.

In some embodiments, $X_2$ is NH or N-(an optionally substituted $C_1$ to $C_6$ alkyl). In some embodiments, $X_2$ is NH.

In some embodiments, $R_3$ and $R_4$, are each independently selected from the group consisting of H and halogen. In some embodiments, $R_5$ is selected from the group consisting of H and an optionally substituted $C_1$ to $C_6$ alkyl. In some embodiments, $R_5$ is H. In some embodiments, $R_5$ is an unsubstituted methyl. In some embodiments $R_5$ is halogen. In some embodiments, $R_5$ is chloro or fluoro. In some embodiments, $R_5$ is not halogen. In some embodiments, $R_6$ is selected from the group consisting of H and an optionally substituted $C_1$ to $C_6$ alkyl. In some embodiments, $R_6$ is H. In some embodiments, $R_6$ is an unsubstituted methyl.

In some embodiments, $R_7$ is selected from the group consisting of an optionally substituted $C_3$ to $C_{10}$ cycloalkyl, an optionally substituted $C_6$ to $C_{10}$ aryl, an optionally substituted 5 to 10-membered heteroaryl, and an optionally substituted 3 to 10-membered heterocyclyl. In some embodiments, the optionally substituted $C_6$ to $C_{10}$ aryl is an unsubstituted phenyl group. In some embodiments, the optionally substituted $C_6$ to $C_{10}$ aryl is an unsubstituted naphthyl group. In some embodiments, the optionally substituted $C_6$ to $C_{10}$ aryl is a $C_6$ aryl group independently substituted with an unsubstituted $C_1$ to $C_6$ alkyl, an unsubstituted alkyl(amino), or an unsubstituted (heterocyclyl)alkyl. In some embodiments, the optionally substituted $C_6$ to $C_{10}$ aryl is a $C_6$ aryl group substituted with an unsubstituted alkyl(amino) (for example, a —$CH_2NH_2$, —$CH_2$—$N(CH_3)_2$, or —$CH_2N(CH_2CH_3)_2$). In some embodiments, the optionally substituted $C_6$ to $C_{10}$ aryl is a $C_6$ aryl group substituted with an unsubstituted (heterocyclyl)alkyl (for example, —$CH_2$(N-morpholino) or —$CH_2$(N-piperazinyl)). In some embodiments, the optionally substituted $C_6$ to $C_{10}$ aryl is a $C_6$ aryl group substituted with halogen. In some embodiments, the optionally substituted $C_6$ to $C_{10}$ aryl is a $C_6$ aryl group substituted with an unsubstituted $C_1$ to $C_6$ alkyl. In some embodiments, the optionally substituted $C_6$ to $C_{10}$ aryl is a $C_6$ aryl group substituted with an unsubstituted $C_1$ to $C_6$ alkyl and halogen. In some embodiments, the optionally substituted 5 to 10-membered heteroaryl is 5 or 6-membered heteroaryl independently substituted with an unsubstituted $C_1$ to $C_6$ alkyl, an unsubstituted alkyl(amino), or an unsubstituted (heterocyclyl)alkyl. In some embodiments, the optionally substituted 5 to 10-membered heteroaryl is 5 or 6-membered heteroaryl substituted with an unsubstituted alkyl(amino) (for example, a —$CH_2NH_2$, —$CH_2$—$N(CH_3)_2$, or —$CH_2N(CH_2CH_3)_2$). In some embodiments, the optionally substituted 5 to 10-membered heteroaryl is 5 or 6-membered heteroaryl substituted with an unsubstituted (heterocyclyl)alkyl (for example, —$CH_2$(N-morpholino) or —$CH_2$(N-piperazinyl)). In some embodiments, the optionally substituted 5 to 10-membered heteroaryl is 5 or 6-membered heteroaryl substituted with halogen. In some embodiments, the optionally substituted 5 to 10-membered heteroaryl is 5 or 6-membered heteroaryl substituted with an unsubstituted $C_1$ to $C_6$ alkyl. In some embodiments, the optionally substituted 5 to 10-membered heteroaryl is 5 or 6-membered heteroaryl substituted with an unsubstituted $C_1$ to $C_6$ alkyl and halogen.

In some embodiments, the compound of Formula (I), or a pharmaceutically acceptable salt thereof, has the structure:

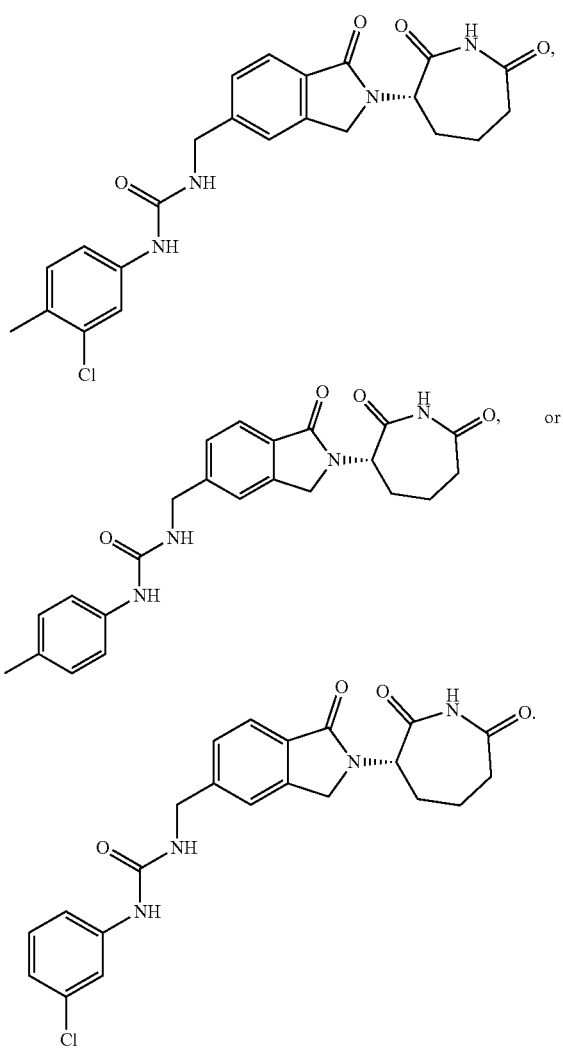

Some embodiments provide a pharmaceutical composition comprising a compound of Formula (I), or a pharmaceutically acceptable salt thereof, and at least one pharmaceutically acceptable carrier.

In some embodiments, the composition is formulated for oral, parenteral, topical, ophthalmic, inhalation, nasal, or intravenous administration. In some embodiments, the pharmaceutical composition further comprises a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent.

Some embodiments provide a method of treating, ameliorating, or preventing a disease, disorder, or condition associated with GSPT1, comprising administering a therapeutically effective amount of a compound of Formula (I), or a pharmaceutically acceptable salt thereof, or a composition comprising a compound of Formula (I), to a subject in need thereof.

In some embodiments, the disease, disorder, or condition is selected from the group consisting of a breast cancer, a lung cancer, a leukemia, a lymphoma, a hepatocellular carcinoma, a gastric cancer, a prostate cancer and astrogliosis.

In some embodiments, the compound is administered in combination with a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent.

Some embodiments provide a method of inhibiting GSPT1 activity, comprising contacting a cell with a compound of Formula (I), or a pharmaceutically acceptable salt thereof. In some embodiments, the compound is provided in combination with a second agent. In some embodiments, the second agent is selected from the group consisting of anti-inflammatory agents, anti-cancer agents, immunostimulatory agents, and immunosuppressive agents. In some embodiments, the second agent is an anti-cancer agent.

Some embodiments provide a method of treating, ameliorating, or preventing a disease, disorder, or condition associated with GSPT1 malfunction, comprising administering a therapeutically effective amount of Formula (I), or a pharmaceutically acceptable salt thereof, or a composition comprising a compound of Formula (I), to a subject in need thereof.

In some embodiments of the method for treating GSPT1 malfunction, the disease, disorder, or condition is selected from the group consisting of a breast cancer, a lung cancer, a leukemia, a lymphoma, a hepatocellular carcinoma, a gastric cancer, a prostate cancer and astrogliosis.

In some embodiments of the method for treating GSPT1 malfunction, the compound of Formula (I) is administered in combination with a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent.

In some embodiments, the subject in need thereof is known to possess wild-type GSPT1. In some embodiments, the subject in need thereof is known to possess aberrant GSPT1.

Any of the features of an embodiment is applicable to all embodiments identified herein. Moreover, any of the features of an embodiment is independently combinable, partly or wholly with other embodiments described herein in any way, e.g., one, two, or three or more embodiments may be combinable in whole or in part. Further, any of the features of an embodiment may be made optional to other embodiments. Any embodiment of a method can comprise another embodiment of a compound, and any embodiment of a compound can be configured to perform a method of another embodiment.

DETAILED DESCRIPTION

Figure 1:
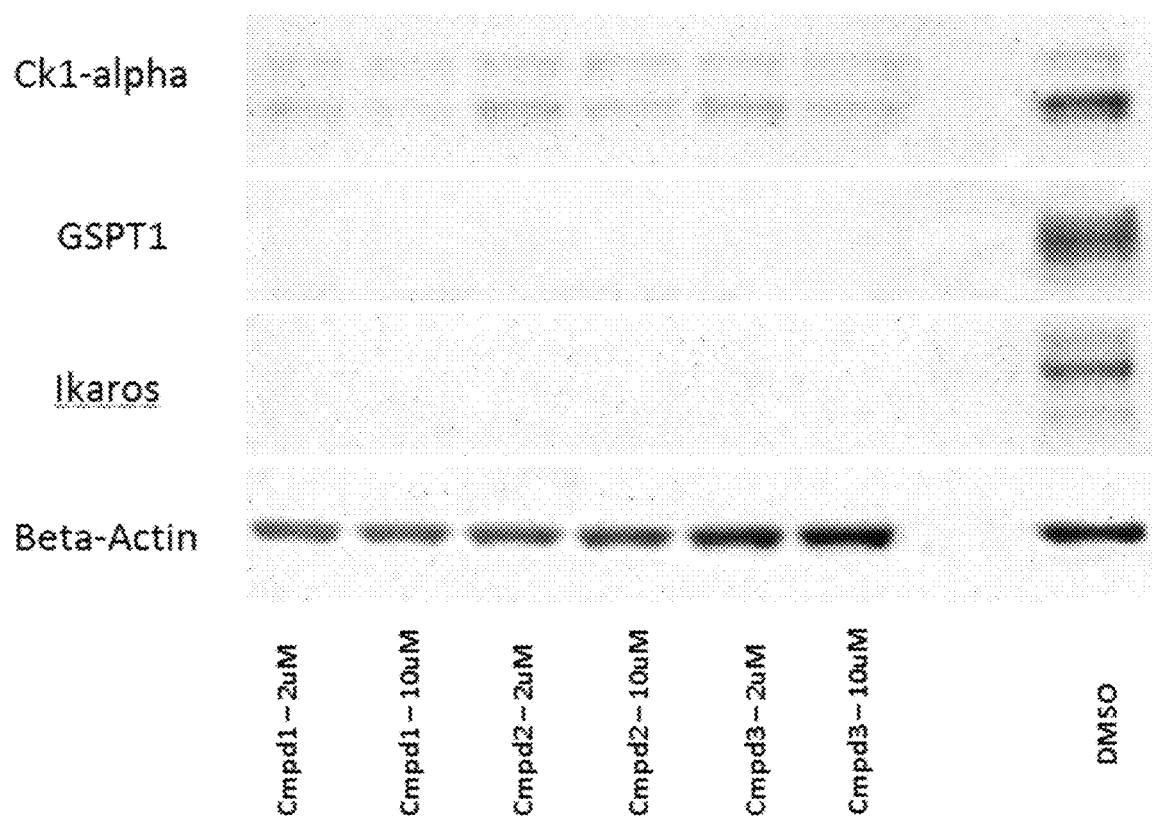
FIG. 1 represents the activity against CK1α, ikaros, and GPST1 in Jurkat cells, plated in 96 well plates. Cells were pretreated with compounds for 4 h and then lysed and protein levels measure via Western blots. The negative control wells were treated with DMSO. Cells were treated with the indicated compound at the indicated concentration. Compound activity is measured as a decrease in GSPT1 protein levels.

Some embodiments provide a compound of Formula (I):

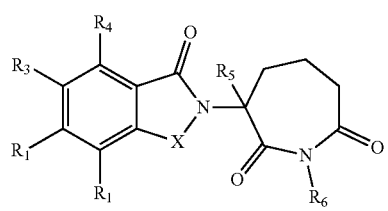

or a pharmaceutically acceptable salt or solvate thereof. Some embodiments provide a pharmaceutically acceptable salt of a compound of Formula (I). Some embodiments provide a solvate of a compound of Formula (I). In some embodiments, the compound of Formula (I) is racemic. In some embodiments, the compound of Formula (I) is a diastereomeric mixture. In some embodiments, the compound of Formula (I) is an (R)-stereoisomer. In some embodiments, the compound of Formula (I) is an (S)-stereoisomer.

In some embodiments, $R_1$, $R_2$, $R_3$, and $R_4$, are each independently selected from the group consisting of H, deuterium, —$NH_2$, —$NHR_7$, $NR_7R_7$, halogen, cyano, nitro, an optionally substituted $C_1$ to $C_6$ alkoxy, and an optionally substituted $C_1$ to $C_6$ alkyl,

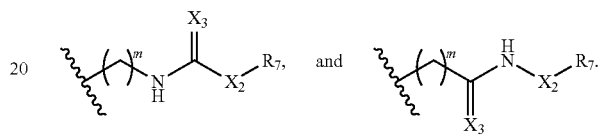

In some embodiments, at least one of $R_1$, $R_2$, $R_3$, and $R_4$ is

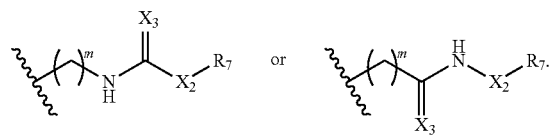

In some embodiments, when any of $R_1$, $R_2$, $R_3$, and $R_4$ is

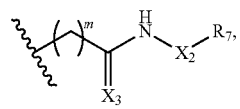

$X_3$, then $X^2$ is $(CH_2)_n$, $(CD_2)_n$, $(CF_2)_n$, C=O, $[(CH_2)_p$—NH—$(CH_2)_q]_r$, and $[(CH_2)_p$—O—$(CH_2)_q]_r$. In some embodiments, when any of $R_1$, $R_2$, $R_3$, and $R_4$ is

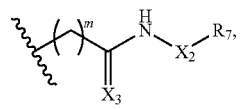

then $X_2$ is not NH or N-(an optionally substituted $C_1$ to $C_6$ alkyl).

In some embodiments, $R_2$, $R_3$, and $R_4$ are each H. In some embodiments, $R_1$, $R_3$, and $R_4$ are each H. In some embodiments, $R_1$ is

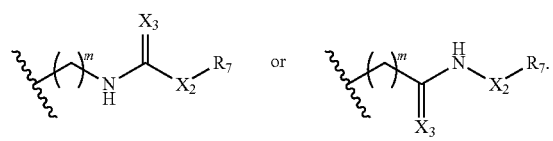

In some embodiments, $R_2$ is

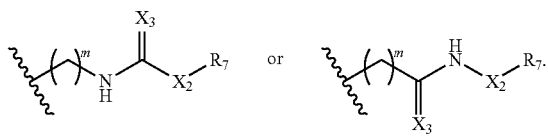

In some embodiments, $R_1$ is

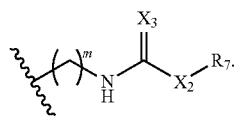

In some embodiments, $R_1$ is

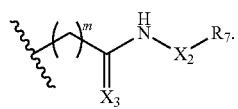

In some embodiments, $R_2$ is

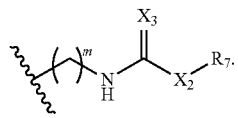

In some embodiments, $R_2$ is

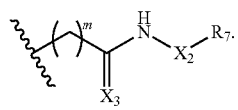

In some embodiments, the halogen of $R^1$ is fluoro or chloro. In some embodiments, the optionally substituted $C_1$ to $C_6$ alkyl of $R^1$ is substituted with halogen. In some embodiments, the optionally substituted $C_1$ to $C_6$ alkoxy of $R^1$ is substituted with halogen. In some embodiments, the optionally substituted $C_1$ to $C_6$ alkyl of $R^1$ is an unsubstituted $C_1$ to $C_6$ alkyl, for example, methyl, ethyl, isopropyl, or t-butyl. In some embodiments, the optionally substituted $C_1$ to $C_6$ alkyl of $R^1$ is an unsubstituted $C_1$ to $C_6$ alkoxy, for example, methoxy, ethoxy, or isopropoxy.

In some embodiments, $R_5$ is selected from the group consisting of H, deuterium, an optionally substituted $C_1$ to $C_6$ alkyl, and halogen. In some embodiments, $R_5$ is H. In some embodiments, $R_5$ is deuterium. In some embodiments, $R_5$ is an optionally substituted $C_1$ to $C_6$ alkyl. In some embodiments, the optionally substituted $C_1$ to $C_6$ alkyl is an unsubstituted $C_1$ to $C_6$ alkyl, for example, methyl, ethyl, isopropyl, or t-butyl. In some embodiments $R_5$ is halogen. In some embodiments, $R_5$ is chloro or fluoro. In some embodiments, $R_5$ is not halogen.

In some embodiments, $R_6$ is selected from the group consisting of H, deuterium, an optionally substituted $C_1$ to $C_6$ alkyl, and an optionally substituted $C_2$ to $C_6$ alkenyl. In some embodiments, $R_6$ is H. In some embodiments, $R_6$ is deuterium. In some embodiments, $R_6$ is an optionally substituted $C_1$ to $C_6$ alkyl. In some embodiments, $R_6$ is and an optionally substituted $C_2$ to $C_6$ alkenyl. In some embodiments, the optionally substituted $C_1$ to $C_6$ alkenyl is an unsubstituted $C_1$ to $C_6$ alkenyl, for example vinyl, allyl, or propenyl. In some embodiments, the optionally substituted $C_1$ to $C_6$ alkyl is an unsubstituted $C_1$ to $C_6$ alkyl, for example, methyl, ethyl, isopropyl, or t-butyl.

In some embodiments, $R_7$ is selected from the group consisting of an optionally substituted $C_3$ to $C_{10}$ cycloalkyl, an optionally substituted $C_6$ to $C_{10}$ aryl, an optionally substituted 5 to 10-membered heteroaryl, an optionally substituted 3 to 10-membered heterocyclyl, and an optionally substituted $C_1$ to $C_{10}$ alkyl.

In some embodiments, $R_7$ is an optionally substituted $C_3$ to $C_{10}$ cycloalkyl. In some embodiments, $R_7$ is an optionally substituted $C_6$ to $C_{10}$ aryl. In some embodiments, $R_7$ is an optionally substituted 5 to 10-membered heteroaryl. In some embodiments, $R_7$ is an optionally substituted 3 to 10-membered heterocyclyl. In some embodiments, $R_7$ is an optionally substituted $C_1$ to $C_{10}$ alkyl. In some embodiments, $R_7$ is an unsubstituted $C_3$ to $C_{10}$ cycloalkyl. In some embodiments, $R_7$ is an unsubstituted $C_6$ to $C_{10}$ aryl. In some embodiments, $R_7$ is an unsubstituted 5 to 10-membered heteroaryl. In some embodiments, $R_7$ is an unsubstituted 3 to 10-membered heterocyclyl. In some embodiments, $R_7$ is an unsubstituted $C_1$ to $C_{10}$ alkyl.

In some embodiments, $R_7$ is a mono-substituted $C_6$ aryl. In some embodiments, $R_7$ is a di-substituted $C_6$ aryl. In some embodiments, $R_7$ is a tri-substituted $C_6$ aryl. In some embodiments, $R_7$ is a substituted 5 or 6-membered heteroaryl. In some embodiments, $R_7$ is a mono-substituted 5 or 6-membered heteroaryl. In some embodiments, $R_7$ is a di-substituted 5 or 6-membered heteroaryl. In some embodiments, $R_7$ is a tri-substituted 5 or 6-membered heteroaryl.

In some embodiments, X is selected from the group consisting of $CH_2$, $(CH_2)_2$, $CH(R_6)$, and $C=O$. In some embodiments, X is $CH_2$. In some embodiments, X is $(CH_2)_2$. In some embodiments, X is $CH(R_6)$. In some embodiments, X is $C=O$.

In some embodiments, $X_2$ is selected from the group consisting of $(CH_2)_n$, $(CD_2)_n$, $(CF_2)_n$, $C=O$, NH, N-(an optionally substituted $C_1$ to $C_6$ alkyl), $[(CH_2)_p-NH-(CH_2)_q]_t$, and $[(CH_2)_p-O-(CH_2)_q]_t$. In some embodiments, $X_2$ is $(CH_2)$. In some embodiments, $X_2$ is $(CD_2)_n$. In some embodiments, $X_2$ is $(CF_2)_n$. In some embodiments, $X_2$ is $C=O$. In some embodiments, $X_2$ is NH. In some embodiments, $X_2$ is N-(an optionally substituted $C_1$ to $C_6$ alkyl). In some embodiments, $X_2$ is $[(CH_2)_p-O-(CH_2)_q]_t$. In some embodiments, $X_2$ is $[(CH_2)_p-NH-(CH_2)_q]_t$.

In some embodiments, $X_3$ is selected from the group consisting of NH, O, and S. In some embodiments, $X_3$ is O. In some embodiments, $X_3$ is S.

In some embodiments, m is 1, 2, 3, 4, or 5. In some embodiments, m is 1. In some embodiments, m is 2. In some embodiments, m is 3. In some embodiments, m is 4. In some embodiments, m is 5. In some embodiments, m is 1 and $X_2$ is NH.

In some embodiments, n is 0, 1, 2, 3, 4, 5, 6, 7, 8, 9, or 10. In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, p and q are independently 0, 1, 2, 3, 4, 5, or 6. In some embodiments, p and q are independently 0. In some embodiments, p and q are independently 1. In some embodiments, p and q are independently 2. In some embodiments, p and q are independently 3. In some embodiments, p and q are independently 4. In some embodiments, p and q are independently 5. In some embodiments, p and q are independently 6.

In some embodiments, p is 0. In some embodiments, p is 1. In some embodiments, p is 2. In some embodiments, p is 3. In some embodiments, p is 4. In some embodiments, p is 5. In some embodiments, p is 6. In some embodiments, q is 0. In some embodiments, q is 1. In some embodiments, q is 2. In some embodiments, q is 3. In some embodiments, q is 4. In some embodiments, q is 5. In some embodiments, q is 6. In some embodiments, p and q are each 0, 1, 2, 3, 4, 5, or 6.

In some embodiments, t is 0, 1, 2, 3, or 4. In some embodiments, t is 0. In some embodiments, t is 1. In some embodiments, t is 2. In some embodiments, t is 3. In some embodiments, t is 4.

In some embodiments, the compound of Formula (I) is selected from:

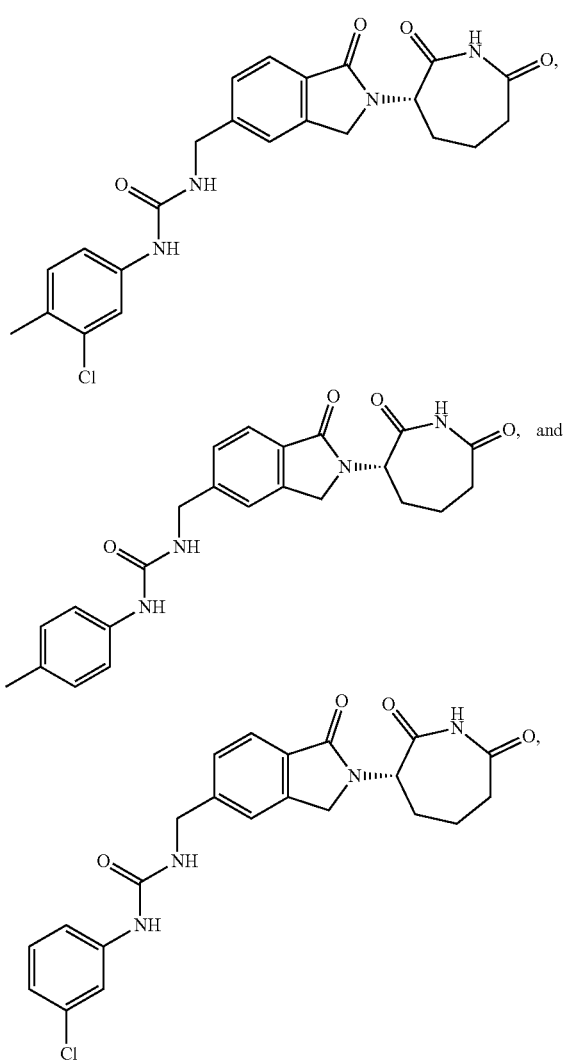

or pharmaceutically acceptable salts, solvates, and combinations of the foregoing.

Some embodiments provide a pharmaceutical composition comprising a compound of Formula (I) and at least one pharmaceutically acceptable carrier. Some embodiments provide a pharmaceutical composition comprising a pharmaceutically acceptable salt or a solvate of a compound of Formula (I) and at least one pharmaceutically acceptable carrier. The definitions for compounds of Formula (I) are the same as those set forth above.

Some embodiments provide methods of treating, ameliorating, or preventing a disease, disorder, or condition associated with GSPT1 function or imbalance, comprising administering a therapeutically effective amount of a compound of Formula (I). Some embodiments provide methods of treating, ameliorating, or preventing a disease, disorder, or condition associated with protein function or imbalance, comprising administering a pharmaceutically acceptable salt of solvate of a compound of Formula (I), to a subject in need thereof. The definitions for compounds of Formula (I) are the same as those set forth above.

In some embodiments of the method for treating, ameliorating, or preventing a disease, disorder, or condition associated with GSPT1 function or imbalance, the disease, disorder, or condition is selected from cancer (for example, a breast cancer, a lung cancer, a leukemia, a lymphoma, a hepatocellular carcinoma, a gastric cancer, or a prostate cancer) and astrogliosis. In some embodiments, the cancer is a breast cancer. In some embodiments, the cancer is a lung cancer. In some embodiments, the cancer is a leukemia. In some embodiments, the cancer is a lymphoma. In some embodiments, the cancer is a hepatocellular carcinoma. In some embodiments, the cancer is a gastric cancer. In some embodiments, the cancer is a prostate cancer. In some embodiments, the disease, disorder, or condition is astrogliosis.

In some embodiments of the method for treating, ameliorating, or preventing a disease, disorder, or condition associated with GSPT1 function or imbalance, the compound of Formula (I) is administered in combination with a second therapeutic agent. In some embodiments the second therapeutic agent is selected from the group consisting of anti-inflammatory agents, anti-cancer agents, immunostimulatory agents, and immunosuppressive agents. In some embodiments the second therapeutic agent is an anti-cancer agent.

Some embodiments provide methods of inhibiting GSPT1 activity, comprising contacting a cell with a compound of Formula (I). Some embodiments provide methods of inhibiting GSPT1 activity, comprising contacting a cell with a pharmaceutically acceptable salt of a compound of Formula (I). The definitions for compounds of Formula (I) are the same as those set forth above.

Some embodiments provide methods of treating, ameliorating, or preventing a disease, disorder, or condition associated with GSPT1 malfunction, comprising administering a therapeutically effective amount of a compound of Formula (I), or a pharmaceutically acceptable salt thereof, to a subject in need thereof.

In some embodiments, the disease, disorder, or condition is cancer. In some embodiments the cancer is selected from a breast cancer, a lung cancer, a leukemia, a lymphoma, a hepatocellular carcinoma, a gastric cancer, and a prostate cancer. In some embodiments, the disease, disorder, or condition is astrogliosis.

Some embodiments provide methods of treating, ameliorating, or preventing a disease, disorder, or condition associated with a protein selected from a cytokine, ailios, ikaros, helios, CK1-alpha, and combinations of any of the foregoing, the method comprising administering a therapeutically effective amount of a compound Formula (I), or a pharmaceutically acceptable salt thereof.

In some embodiments, the disease, disorder, or condition is selected from the group consisting of inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer.

In some embodiments, the compound of Formula (I) is administered in combination with a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent.

Some embodiments provide methods of inhibiting protein activity, comprising contacting a cell with a compound of Formula (I), or a pharmaceutically acceptable salt thereof, wherein the protein is ailios, ikaros, helios, CK1α, a cytokine, or a combination of any of the foregoing.

Some embodiments provide methods of decreasing the risk of skin cancer in a subject in need thereof, comprising administering an effective amount of a compound of Formula (I), or a pharmaceutically acceptable salt thereof.

Some embodiments provide methods for treating, ameliorating, or preventing a skin disorder, disease, or condition in a subject, comprising administering to the subject a therapeutically effective amount of a compound of Formula (I), or a pharmaceutically acceptable salt thereof. In some embodiments, the skin disorder, disease, or condition is sunburn or skin hypopigmentation.

Some embodiments provide methods for treating, ameliorating, or preventing a skin disorder, disease, or condition in a subject, comprising administering to the subject a therapeutically effective amount of a compound of Formula (I), or a pharmaceutically acceptable salt thereof.

Some embodiments provide methods for increasing skin pigmentation in a subject in need thereof, comprising administering a therapeutically effective amount of a compound of Formula (I), or a pharmaceutically acceptable salt thereof. In some embodiments, the administering comprises contacting the skin with a therapeutically effective amount of Formula (I), or a pharmaceutically acceptable salt thereof.

Some embodiments provide methods for increasing eumelanin level in a subject in need thereof, comprising administering a therapeutically effective amount of a compound of Formula (I), or a pharmaceutically acceptable salt thereof. In some embodiments, administering comprises contacting the skin with a therapeutically effective amount of a compound of Formula (I), or a pharmaceutically acceptable salt thereof.

Some embodiments provide methods for increasing p53 activity, comprising contacting a cell with a compound of Formula (I), or a pharmaceutically acceptable salt thereof. Some embodiments provide methods for decreasing MDM2 activity, comprising contacting a cell with a compound of Formula (I), or a pharmaceutically acceptable salt thereof.

In some embodiments of the method for treating, ameliorating, or preventing a disease, disorder, or condition associated with GSPT1 function or imbalance, the compound of Formula (I) is administered in combination with a second therapeutic agent. In some embodiments the second therapeutic agent is selected from the group consisting of anti-inflammatory agents, anti-cancer agents, immunostimulatory agents, and immunosuppressive agents. In some embodiments the second therapeutic agent is an anti-cancer agent.

In some embodiments the compound of Formula (I) is selected from the group consisting of:

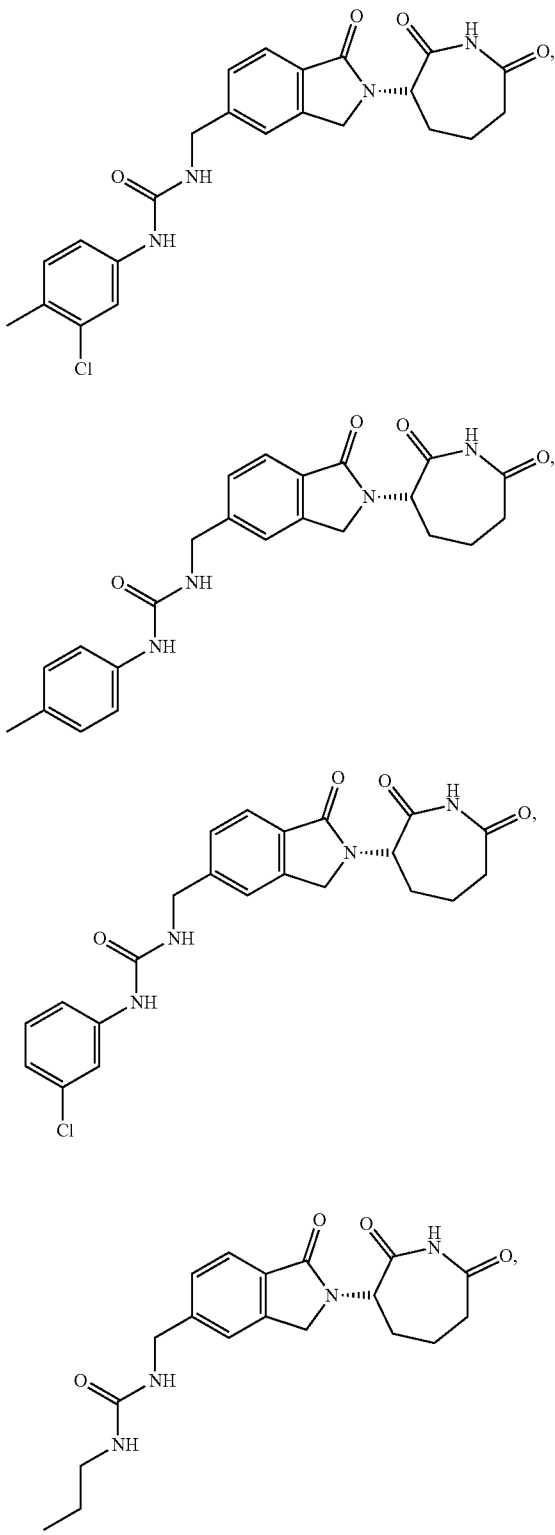

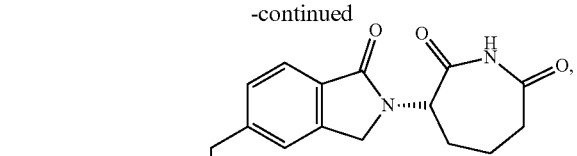
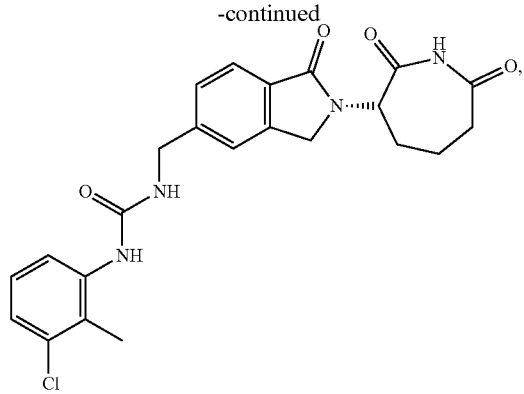
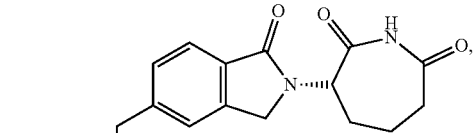
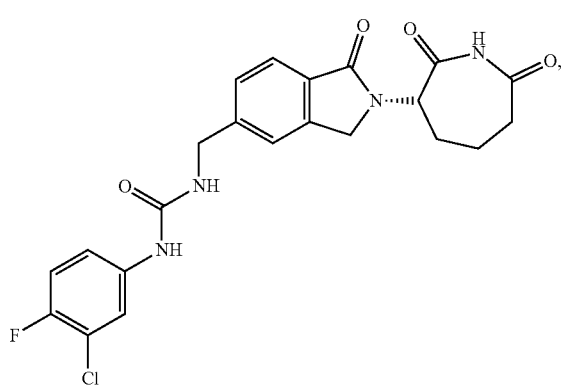
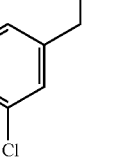
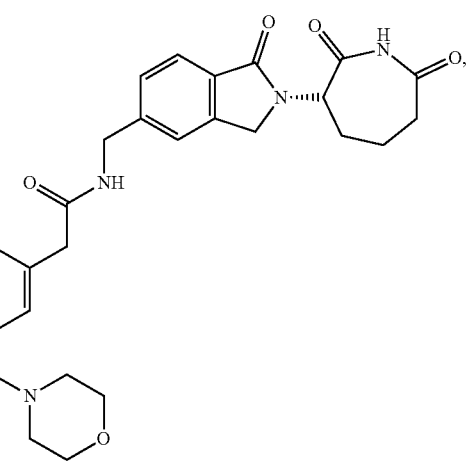
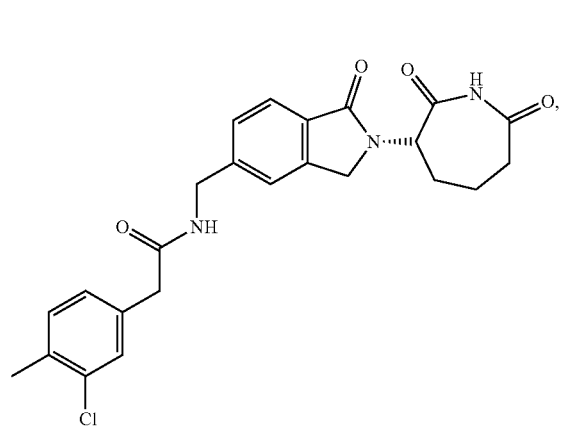
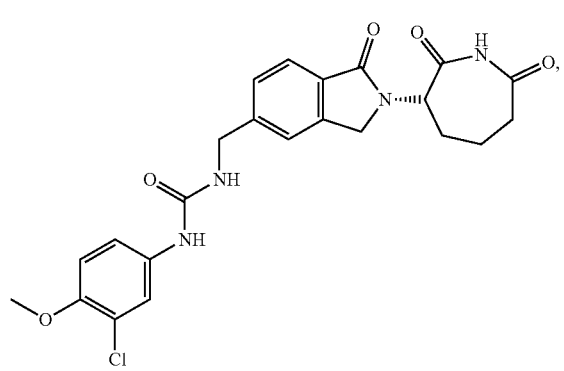
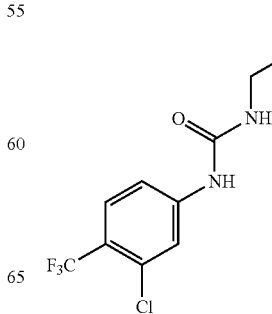

19
-continued
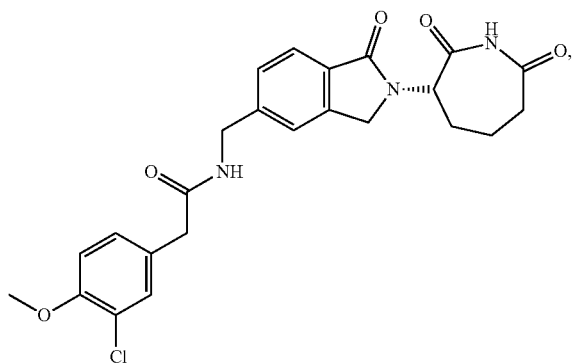
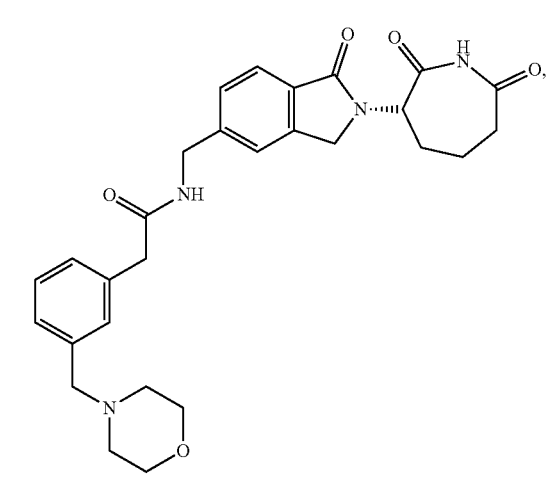
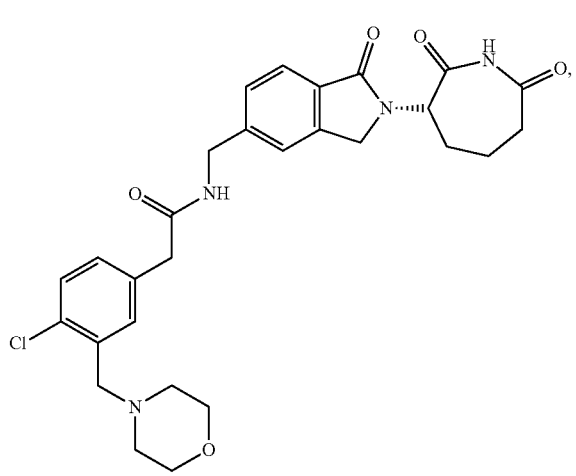
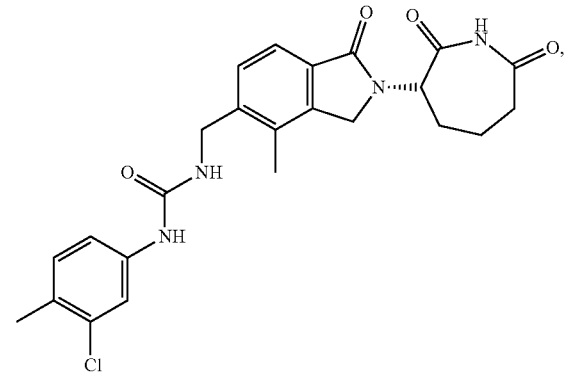
20
-continued
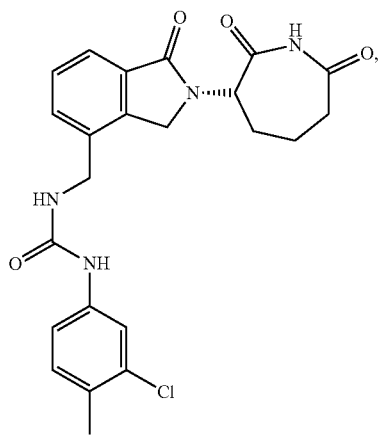
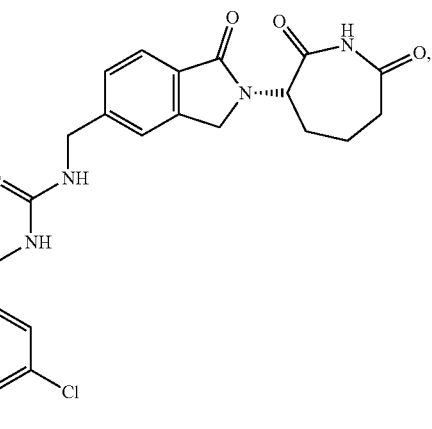
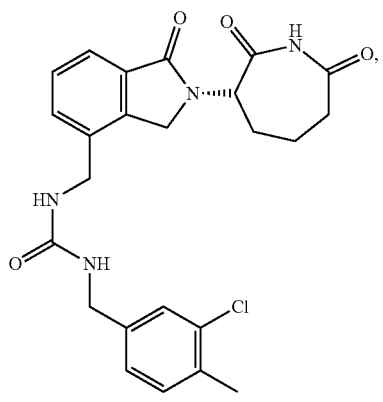

21
-continued

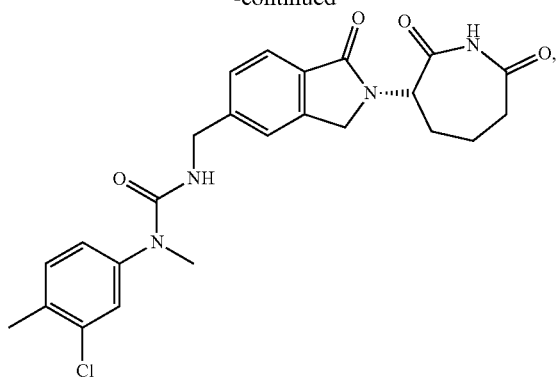

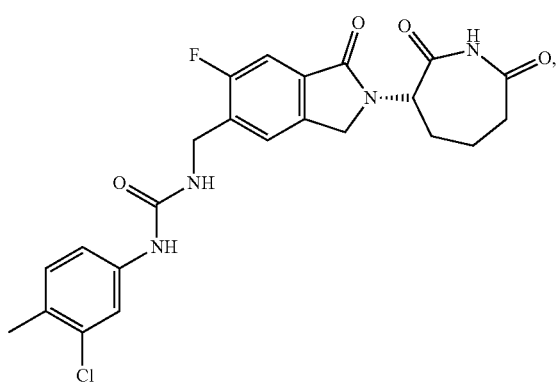

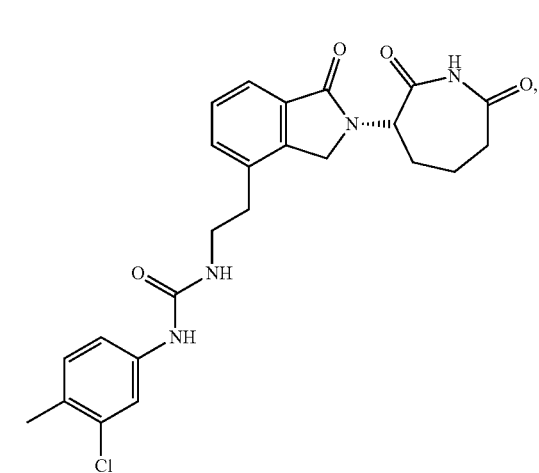

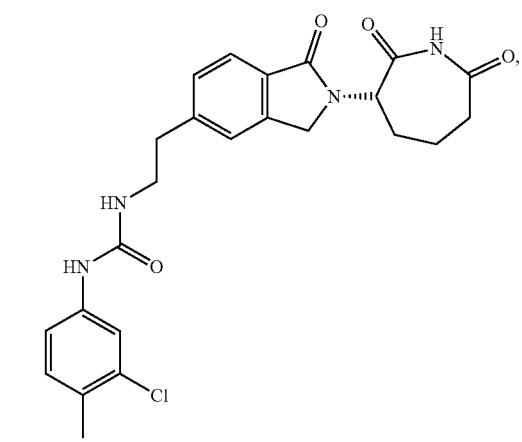

22
-continued

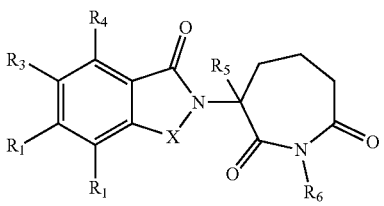

and and pharmaceutically acceptable salts and combinations of the foregoing.

In some embodiments, the subject in need thereof is known to possess wild-type GSPT1. In some embodiments, the subject in need thereof is known to possess aberrant GSPT1.

Some embodiments provide a compound of Formula (I):

$$\text{(I)}$$

or a pharmaceutically acceptable salt or solvate thereof.

In some embodiments, $R_1$, $R_2$, $R_3$, and $R_4$, are each independently selected from the group consisting of H, deuterium, halogen, cyano, nitro, —NH$_2$, —NHR$_7$, NR$_7$R$_7$, an optionally substituted C$_1$ to C$_6$ alkoxy, an optionally substituted C$_1$ to C$_6$ alkyl,

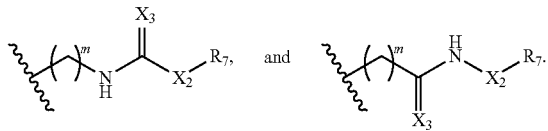

In some embodiments, at least one of R$_1$, R$_2$, R$_3$, and R$_4$ is

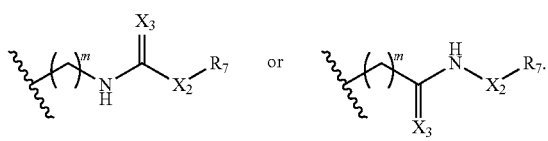

In some embodiments, R$_5$ is selected from the group consisting of H, deuterium, fluoro, and an optionally substituted C$_1$ to C$_6$ alkyl.

In some embodiments, R$_6$ is selected from the group consisting of H, deuterium, and an optionally substituted C$_1$ to C$_6$ alkyl.

In some embodiments, X is selected from the group consisting of CH$_2$ and C=O;

In some embodiments, X$_2$ is selected from the group consisting of (CH$_2$)$_n$, (CD$_2$)$_n$, (CF$_2$)$_n$, C=O, NH, N-(an optionally substituted C$_1$ to C$_6$ alkyl), [(CH$_2$)$_p$—NH—(CH$_2$)$_q$]$_t$ and [(CH$_2$)$_p$—O—(CH$_2$)$_q$]$_t$.

In some embodiments, X$_3$ is selected from the group consisting of NH, O, and S.

In some embodiments, when any of R$_1$, R$_2$, R$_3$, or R$_4$ is

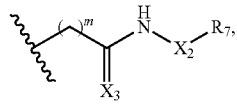

X$_2$ is selected from the group consisting of (CH$_2$)$_n$, (CD$_2$)$_n$, C=O, [(CH$_2$)$_p$—NH—(CH$_2$)$_q$]$_t$, and [(CH$_2$)$_p$—O—(CH$_2$)$_q$]$_t$;

In some embodiments, m is 1, 2, 3, 4, or 5. In some embodiments, n is 0, 1, 2, 3, 4, 5, 6, 7, 8, 9, or 10. In some embodiments, p and q are independently 0, 1, 2, 3, 4, 5, or 6. In some embodiments, t is 0, 1, 2, 3, or 4.

In some embodiments, R$_7$ is selected from the group consisting of an optionally substituted C$_3$ to C$_{10}$ cycloalkyl, an optionally substituted C$_6$ to C$_{10}$ aryl, an optionally substituted 5 to 10-membered heteroaryl, an optionally substituted 3 to 10-membered heterocyclyl, and an optionally substituted C$_1$ to C$_{10}$ alkyl.

In some embodiments, R$^1$ is

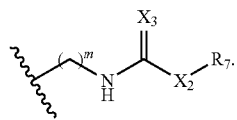

In some embodiments, R$^2$ is

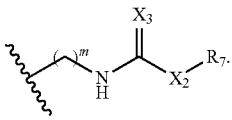

In some embodiments, R$^1$ is

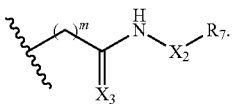

In some embodiments, R$^2$ is

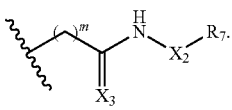

In some embodiments, m is 1. In some embodiments, m is 2. In some embodiments, X$_3$ is NH. In some embodiments, X$_3$ is O. In some embodiments, X$_3$ is S. In some embodiments, X$_2$ is selected from the group consisting of (CH$_2$)$_n$, C=O, and [(CH$_2$)$_p$—NH—(CH$_2$)$_q$]$_t$. In some embodiments, X$_2$ is (CH$_2$)$_n$ and n is 0, 1, or 2. In some embodiments, X$_2$ is [(CH$_2$)$_p$—NH—(CH$_2$)$_q$]$_t$ and p and q are independently 0, 1, or 2; and t is 1 or 2. In some embodiments, X$_2$ is NH or N-(an unsubstituted C$_1$ to C$_6$ alkyl). In some embodiments, X$_2$ is NH.

In some embodiments, R$_3$ and R$_4$, are each independently selected from the group consisting of H and halogen. In some embodiments, R$_5$ is selected from the group consisting of H and deuterium. In some embodiments, R$_6$ is H.

In some embodiments, R$_7$ is selected from the group consisting of an optionally substituted C$_3$ to C$_{10}$ cycloalkyl, an optionally substituted C$_6$ to C$_{10}$ aryl, an optionally substituted 5 to 10-membered heteroaryl, and an optionally substituted 3 to 10-membered heterocyclyl. In some embodiments, the optionally substituted C$_6$ to C$_{10}$ aryl is a mono-substituted phenyl group. In some embodiments, the optionally substituted C$_6$ to C$_{10}$ aryl is a di-substituted phenyl group. In some embodiments, the optionally substituted C$_6$ to C$_{10}$ aryl is a tri-substituted phenyl group. In some embodiments, the optionally substituted C$_6$ to C$_{10}$ aryl is a phenyl group mono-substituted or independently di-substituted with halogen.

In some embodiments, the optionally substituted 5 to 10-membered heteroaryl is 5 or 6-membered heteroaryl independently substituted with halogen, an unsubstituted C$_1$ to C$_6$ alkyl, an unsubstituted alkyl(amino), or an unsubstituted (heterocyclyl)alkyl. In some embodiments, the optionally substituted C$_6$ to C$_{10}$ aryl is a phenyl group mono-substituted with an unsubstituted C$_1$ to C$_6$ alkyl. In some embodiments, the optionally substituted C$_6$ to C$_{10}$ aryl is a phenyl group substituted with —N(CH$_3$)$_2$, —N(CH$_2$CH$_3$)$_2$,

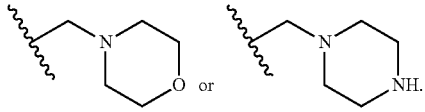 [SMILES: *CN1CCOCC1 ; *CN1CCNCC1]

In some embodiments, the optionally substituted $C_6$ to $C_{10}$ aryl is a phenyl group substituted with 1, 2, or 3 substituents independently selected from halogen, unsubstituted $C_1$ to $C_6$ alkyl, —N(unsubstituted $C_1$ to $C_6$ alkyl)(unsubstituted $C_1$ to $C_6$ alkyl), and unsubstituted $C_1$ to $C_6$ alkoxy. In some embodiments, the optionally substituted $C_6$ to $C_{10}$ aryl is a phenyl group substituted with 1 or 2 unsubstituted $C_1$ to $C_6$ alkyl groups and 1 or 2 halogens. In some embodiments, the optionally substituted $C_6$ to $C_{10}$ aryl is a phenyl group substituted with 1 unsubstituted $C_1$ to $C_6$ alkyl group and 1 halogen.

In some embodiments, $R_1$ is an optionally substituted $C_1$ to $C_6$ alkyl; $R_2$ is

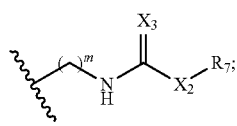

$R_3$ and $R_4$ are independently hydrogen or halogen; m is 1; $X_2$ is NH; and $X_3$ is O or S. In some embodiments, $R_1$ is an unsubstituted $C_1$ to $C_6$ alkyl and $X_3$ is O. In some embodiments, $R_1$ is an unsubstituted methyl; and $R_3$ and $R_4$ are both hydrogen.

In some embodiments, the optionally substituted 5 to 10-membered heteroaryl is 5 or 6-membered heteroaryl substituted with an unsubstituted $C_1$ to $C_6$ alkyl and halogen.

Some embodiments provide a method of treating, ameliorating, or preventing a disease, disorder, or condition associated with GSPT1, comprising administering a therapeutically effective amount of a compound of Formula (I), or a pharmaceutically acceptable salt thereof, to a subject in need thereof; and wherein the disease, disorder, or condition is selected from the group consisting of a breast cancer, a lung cancer, a leukemia, a lymphoma, a hepatocellular carcinoma, a gastric cancer, a prostate cancer and astrogliosis.

Some embodiments provide a method of inhibiting GSPT1 activity, comprising contacting a cell with a compound of Formula (I), or a pharmaceutically acceptable salt thereof.

Some embodiments provide for the use of a compound of Formula (I), or a pharmaceutically acceptable salt thereof, for preparing a medicament for treating, ameliorating, or preventing a disease, disorder, or condition associated with GSPT1; wherein the disease, disorder, or condition is selected from the group consisting of breast cancer, hepatocellular carcinoma, gastric cancer, prostate cancer and astrogliosis.

Some embodiments provide for the use of a compound of Formula (I), or a pharmaceutically acceptable salt thereof, for preparing a medicament for contacting a cell having aberrant GSPT1, thereby inhibiting GSPT1 activity.

One or more of the compounds of preferred embodiments can be provided in the form of pharmaceutically acceptable salts, solvates, active metabolites, tautomers, or prodrugs thereof. Some embodiments can be provided in pharmaceutical compositions comprising a therapeutically effective amount of the compound. In some embodiments, the pharmaceutical composition also contains at least one pharmaceutically acceptable inactive ingredient. The pharmaceutical composition can be formulated for intravenous injection, subcutaneous injection, oral administration, buccal administration, inhalation, nasal administration, topical administration, transdermal administration, ophthalmic administration, or otic administration. The pharmaceutical composition can be in the form of a tablet, a pill, a capsule, a liquid, an inhalant, a nasal spray solution, a suppository, a suspension, a gel, a colloid, a dispersion, a solution, an emulsion, an ointment, a lotion, an eye drop, or an ear drop.

The pharmaceutical compositions of preferred embodiments can further comprise one or more additional therapeutically active agents other than a compound of the preferred embodiments. Such agents can include, but are not limited to, anti-inflammatory agents, anti-cancer agents, immunostimulatory agents, and immunosuppressive agents.

Other objects, features, and advantages of the compounds, methods, and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise. As used in the specification and the appended claims, the singular forms "a," "an" and "the" include plural referents unless the context clearly dictates otherwise. Unless otherwise indicated, conventional methods of mass spectroscopy, NMR, HPLC, protein chemistry, biochemistry, recombinant DNA techniques and pharmacology are employed. The use of "or" or "and" means "and/or" unless stated otherwise. Furthermore, use of the term "including" as well as other forms, such as "include", "includes," and "included," is not limiting. As used in this specification, whether in a transitional phrase or in the body of the claim, the terms "comprise(s)" and "comprising" are to be interpreted as having an open-ended meaning. That is, the terms are to be interpreted synonymously with the phrases "having at least" or "including at least." When used in the context of a process, the term "comprising" means that the process includes at least the recited steps, but may include additional steps. When used in the context of a compound, composition, or device, the term "comprising" means that the compound, composition, or device includes at least the recited features or components, but may also include additional features or components.

The section headings used herein are for organizational purposes only and are not to be construed as limiting the subject matter described.

As used herein, common organic abbreviations are defined as follows:
ACN Acetonitrile
AIBN 2,2'-Azobis(2-methylpropionitrile)
° C. Temperature in degrees Centigrade
DIEA Diisopropylethylamine
DMSO Dimethylsulfoxide
EDCI 1-Ethyl-3-(3-dimethylaminopropyl)carbodiimide
g Gram(s)
h or hr Hour(s)
HOBt 1-hydroxybenzotriazole
IL Interleukin LPS Lipopolysaccharide
M-CSF Macrophage colony-stimulating factor
MS Mass spectrometry
mg Milligram(s)
mL Milliliter(s)
NaCl Sodium chloride
NBS N-bromosuccinimide
nM Nanomolar
PBMC Peripheral blood mononuclear cell
PG Protecting group
RPMI Roswell Park Memorial Institute medium
rt Room temperature
Sat. Saturated solution
TEA Triethylamine
TFA Trifluoroacetic acid (or 2,2,2-trifluoroacetic acid)
TNF Tumor necrosis factor
μL Microliter(s)
μM Micromolar
wt. weight The term "protein malfunction," as used herein, refers to a protein or proteins not properly performing its intended biological function. For example, overexpression or underexpression and mutations in structure/function constitute a protein malfunction. Likewise, a protein or proteins that are expressed normally, and function normally, but are unable to perform their intended biological function (i.e., suppress tumor growth) are also malfunctioning proteins.

The term "protein homeostasis," as used herein, refers to the normal range of physiological levels of a protein or proteins.

The terms "co-administration" and similar terms as used herein are broad terms, and are to be given their ordinary and customary meaning to a person of ordinary skill in the art (and are not to be limited to a special or customized meaning), and refer without limitation to administration of the selected therapeutic agents to a single patient, and are intended to include treatment regimens in which the agents are administered by the same or different route of administration or at the same or different time.

The terms "effective amount" and "therapeutically effective amount" are broad terms, and are to be given their ordinary and customary meaning to a person of ordinary skill in the art (and are not to be limited to a special or customized meaning), and refer without limitation to a sufficient amount of an agent or a compound being administered which will relieve to some extent one or more of the symptoms of the disease or condition being treated. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case may be determined using techniques, such as a dose escalation study. Where a drug has been approved by the U.S. Food and Drug Administration (FDA) or a counterpart foreign medicines agency, a "therapeutically effective amount" an optionally refers to the dosage approved by the FDA or its counterpart foreign agency for treatment of the identified disease or condition.

The term "pharmaceutical combination" as used herein is a broad term, and is to be given its ordinary and customary meaning to a person of ordinary skill in the art (and is not to be limited to a special or customized meaning), and refers without limitation to a product that results from the mixing or combining of more than one active ingredient and includes both fixed and non-fixed combinations of the active ingredients. The term "fixed combination" means that the active ingredients, e.g., a compound of a preferred embodiment and a co-agent, are both administered to a patient simultaneously in the form of a single entity or dosage. The term "non-fixed combination" means that the active ingredients, e.g., a compound of a preferred embodiment and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g., the administration of three or more active ingredients.

As used herein, any "R" group(s) such as, without limitation, $R_2$, $R_3$, $R_4$, $R_5$, $R_6$, $R_9$, and $R_{10}$ represent substituents that can be attached to the indicated atom. An R group may be substituted or an unsubstituted. If two "R" groups are described as being "taken together" the R groups and the atoms they are attached to can form a cycloalkyl, aryl, heteroaryl, or heterocycle. For example, without limitation, if $R^2$ and $R^3$, or $R^2$, $R^3$, or $R^4$, and the atom to which it is attached, are indicated to be "taken together" or "joined together" it means that they are covalently bonded to one another to form a ring:

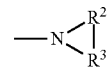

Whenever a group is described as being "an optionally substituted" that group may be an unsubstituted or substituted with one or more of the indicated substituents. Likewise, when a group is described as being "an unsubstituted or substituted" if substituted, the substituent may be selected from one or more the indicated substituents. If no substituents are indicated, it is meant that the indicated "an optionally substituted" or "substituted" group may be individually and independently substituted with one or more group(s) individually and independently selected from alkyl, alkenyl, alkynyl, cycloalkyl, cycloalkenyl, cycloalkynyl, aryl, heteroaryl, heterocyclyl, aralkyl, heteroaralkyl, (heterocyclyl)alkyl, hydroxy, protected hydroxyl, alkoxy, aryloxy, acyl, mercapto, alkylthio, arylthio, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, protected C-carboxy, O-carboxy, isocyanato, thiocyanato, isothiocyanato, nitro, silyl, sulfenyl, sulfinyl, sulfonyl, haloalkyl, alkyl(amino), haloalkoxy, trihalomethanesulfonyl, trihalomethanesulfonamido, amino, mono-substituted amino group and di-substituted amino group, and protected derivatives thereof.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, cycloalkynyl, aryl, heteroaryl or heteroyclyl group. That is, the alkyl, alkenyl, alkynyl, ring of the cycloalkyl, ring of the cycloalkenyl, ring of the cycloalkynyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, cycloalkynyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. By way of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl, and t-butyl. Typical alkyl groups include, but are in no way limited to, methyl, ethyl, propyl, isopropyl, butyl, isobutyl, tertiary butyl, pentyl, and hexyls. The alkyl group may be substituted or an unsubstituted.

As used herein, "alkenyl" refers to an alkyl group, as defined herein, that contains in the straight or branched hydrocarbon chain one or more double bonds. An alkenyl group may be an unsubstituted or substituted.

As used herein, "alkynyl" refers to an alkyl group as defined herein, that contains in the straight or branched hydrocarbon chain one or more triple bonds. An alkynyl group may be an unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s) or 3 to 8 atoms in the ring(s). A cycloalkyl group may be an unsubstituted or substituted. Typical cycloalkyl groups include, but are in no way limited to, cyclopropyl, cyclobutyl, cyclopentyl, cyclohexyl, cycloheptyl, and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl group may be an unsubstituted or substituted.

As used herein, "cycloalkynyl" refers to a mono- or multi-cyclic hydrocarbon ring system that contains one or more triple bonds in at least one ring. If there is more than one triple bond, the triple bonds cannot form a fully delocalized pi-electron system throughout all the rings. When composed of two or more rings, the rings may be joined together in a fused fashion. A cycloalkynyl group may be an unsubstituted or substituted.

As used herein, "carbocyclyl" or "cyclic hydrocarbyl" refers to all carbon ring systems. Such systems can be unsaturated, can include some unsaturation, or can contain some aromatic portion, or be all aromatic. Carbocyclyl group can contain from 3 to 30 carbon atoms. A carbocyclyl group may be an unsubstituted or substituted.

As used herein, "aryl" refers to a carbocyclic (all carbon) monocyclic or multicyclic aromatic ring system (including, e.g., fused, bridged, or spiro ring systems where two carbocyclic rings share a chemical bond, e.g., one or more aryl rings with one or more aryl or non-aryl rings) that has a fully delocalized pi-electron system throughout at least one of the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene, and azulene. An aryl group may be substituted or an unsubstituted.

As used herein, "heterocyclyl" refers to mono- or polycyclic ring systems including at least one heteroatom (e.g., O, N, S). Such systems can be unsaturated, can include some unsaturation, or can contain some aromatic portion, or be all aromatic. A heterocyclyl group can contain from 3 to 30 atoms. A heterocyclyl group may be an unsubstituted or substituted.

As used herein, "heteroaryl" refers to a monocyclic or multicyclic aromatic ring system (a ring system having a least one ring with a fully delocalized pi-electron system) that contain(s) one or more heteroatoms, that is, an element other than carbon, including but not limited to, nitrogen, oxygen, and sulfur, and at least one aromatic ring. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline, and triazine. A heteroaryl group may be substituted or an unsubstituted.

As used herein, "heterocyclic" or "heterocyclyl" refers to three-, four-, five-, six-, seven-, eight-, nine-, ten-, up to 18-membered monocyclic, bicyclic, and tricyclic ring system wherein carbon atoms together with from 1 to 5 heteroatoms constitute said ring system. A heterocycle may an optionally contain one or more unsaturated bonds situated in such a way, however, that a fully delocalized pi-electron system does not occur throughout all the rings. The heteroatoms are independently selected from oxygen, sulfur, and nitrogen. A heterocycle may further contain one or more carbonyl or thiocarbonyl functionalities, so as to make the definition include oxo-systems and thio-systems such as lactams, lactones, cyclic imides, cyclic thioimides, and cyclic carbamates. When composed of two or more rings, the rings may be joined together in a fused fashion. Additionally, any nitrogens in a heterocyclic may be quaternized. Heterocyclyl or heterocyclic groups may be an unsubstituted or substituted. Examples of such "heterocyclic" or "heterocyclyl" groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-oxide, piperidine, piperazine, pyrrolidine, pyrrolidone, pyrrolidine, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone, and their benzo-fused analogs (e.g., benzimidazolidinone, tetrahydroquinoline, 3,4-methylenedioxyphenyl).

"Lower alkylene groups" are straight-chained —$CH_2$— tethering groups, forming bonds to connect molecular fragments via their terminal carbon atoms. Lower alkylene groups contain from 1 to 6 carbon atoms. Examples include but are not limited to methylene (—$CH_2$—), ethylene (—$CH_2CH_2$—), propylene (—$CH_2CH_2CH_2$—), and butylene (—$CH_2CH_2CH_2CH_2$—). A lower alkylene group can be substituted by replacing one or more hydrogen of the lower alkylene group with a substituent(s) listed under the definition of "substituted."

As used herein, "aralkyl" and "aryl(alkyl)" refer to an aryl group, as defined above, connected, as a substituent, via a lower alkylene group, as described above. The lower alkylene and aryl group of an aralkyl may be substituted or an unsubstituted. Examples include but are not limited to benzyl, 2-phenylalkyl, 3-phenylalkyl, and naphthylalkyl.

As used herein, "heteroaralkyl" and "heteroaryl(alkyl)" refer to a heteroaryl group, as defined above, connected, as a substituent, via a lower alkylene group, as defined above. The lower alkylene and heteroaryl group of heteroaralkyl may be substituted or an unsubstituted. Examples include but are not limited to 2-thienylalkyl, 3-thienylalkyl, furylalkyl, thienylalkyl, pyrrolylalkyl, pyridylalkyl, isoxazolylalkyl, and imidazolylalkyl, and their benzo-fused analogs.

A "(heterocyclyl)alkyl" is a heterocyclic or a heterocyclic group, as defined above, connected, as a substituent, via a lower alkylene group, as defined above. The lower alkylene and heterocyclic or a heterocyclyl of a (heterocyclyl)alkyl may be substituted or an unsubstituted. Examples include but are not limited to tetrahydro-2H-pyran-4-yl) methyl, (piperidin-4-yl)ethyl, (piperidin-4-yl)propyl, (tetrahydro-2H-thiopyran-4-yl)methyl, and (1,3-thiazinan-4-yl) methyl. The heterocyclyl group can be connected to the lower alkylene group via a carbon atom of the heterocyclyl group or via a heteroatom of the heterocyclyl group (for example, by a nitrogen atom).

As used herein, "alkoxy" refers to the formula —OR wherein R is an alkyl, an alkenyl, an alkynyl, a cycloalkyl, a cycloalkenyl or a cycloalkynyl, as defined above. A non-limiting list of alkoxys is methoxy, ethoxy, n-propoxy, 1-methylethoxy (isopropoxy), n-butoxy, iso-butoxy, sec-butoxy, and tert-butoxy. An alkoxy may be substituted or an unsubstituted.

As used herein, "acyl" refers to a hydrogen, alkyl, alkenyl, alkynyl, or aryl, as defined above, connected, as substituents, via a carbonyl group. Examples include formyl, acetyl, propanoyl, benzoyl, and acryl. An acyl may be substituted or an unsubstituted.

As used herein, "hydroxyalkyl" refers to an alkyl group in which one or more of the hydrogen atoms are replaced by a hydroxy group. Exemplary hydroxyalkyl groups include but are not limited to, 2-hydroxyethyl, 3-hydroxypropyl, 2-hydroxypropyl, and 2,2-dihydroxyethyl. A hydroxyalkyl may be substituted or an unsubstituted.

As used herein, "haloalkyl" refers to an alkyl group in which one or more of the hydrogen atoms are replaced by a halogen (e.g., mono-haloalkyl, di-haloalkyl, and tri-haloalkyl). Such groups include but are not limited to, chloromethyl, fluoromethyl, difluoromethyl, trifluoromethyl and 1-chloro-2-fluoromethyl, 2-fluoroisobutyl. A haloalkyl may be substituted or an unsubstituted.

As used herein, "haloalkoxy" refers to an alkoxy group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy and 1-chloro-2-fluoromethoxy, 2-fluoroisobutoxy. A haloalkoxy may be substituted or an unsubstituted.

As used herein, "aryloxy" and "arylthio" refers to RO— and RS—, in which R is an aryl, as defined above, such as but not limited to phenyl. Both an aryloxy and arylthio may be substituted or an unsubstituted.

A "sulfenyl" group refers to an "—SR" group in which R can be hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. A sulfenyl may be substituted or an unsubstituted.

A "sulfinyl" group refers to an "—S(=O)—R" group in which R can be the same as defined with respect to sulfenyl. A sulfinyl may be substituted or an unsubstituted.

A "sulfonyl" group refers to an "$SO_2R$" group in which R can be the same as defined with respect to sulfenyl. A sulfonyl may be substituted or an unsubstituted.

An "O-carboxy" group refers to a "RC(=O)O—" group in which R can be hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined herein. An O-carboxy may be substituted or an unsubstituted.

The terms "ester" and "C-carboxy" refer to a "—C(=O) OR" group in which R can be the same as defined with respect to O-carboxy. An ester and C-carboxy may be substituted or an unsubstituted.

A "thiocarbonyl" group refers to a "—C(=S)R" group in which R can be the same as defined with respect to O-carboxy. A thiocarbonyl may be substituted or an unsubstituted.

A "trihalomethanesulfonyl" group refers to an "$X_3CSO_2$—" group wherein X is a halogen.

A "trihalomethanesulfonamido" group refers to an "$X_3CS(O)_2N(R_A)$—" group wherein X is a halogen and $R_A$ hydrogen, alkyl, alkenyl, alkynyl, cycloalkyl, cycloalkenyl, cycloalkynyl, aryl, heteroaryl, heterocyclyl, aralkyl, or (heterocyclyl)alkyl.

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C=O group.

An "alkyl(amino)" group refers to a "—$(CH_2)_{1-6}$—N$(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. An alkyl(amino) may be substituted or an unsubstituted.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, cycloalkynyl, aryl, heteroaryl, heterocyclyl, aralkyl, or (heterocyclyl) alkyl, as defined above. An S-sulfonamido may be substituted or an unsubstituted.

An "N-sulfonamido" group refers to a "RSO$_2$N(R$_A$)—" group in which R and R$_A$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. An N-sulfonamido may be substituted or an unsubstituted.

An "O-carbamyl" group refers to a "—OC(=O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. An O-carbamyl may be substituted or an unsubstituted.

An "N-carbamyl" group refers to an "ROC(=O)N(R$_A$)—" group in which R and R$_A$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. An N-carbamyl may be substituted or an unsubstituted.

An "O-thiocarbamyl" group refers to a "—OC(=S)—N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. An O-thiocarbamyl may be substituted or an unsubstituted.

An "N-thiocarbamyl" group refers to an "ROC(=S)N(R$_A$)—" group in which R and R$_A$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. An N-thiocarbamyl may be substituted or an unsubstituted.

A "C-amido" group refers to a "—C(=O)N(R$_A$R$_B$)" group in which R$_A$ and R$_B$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. A C-amido may be substituted or an unsubstituted.

An "N-amido" group refers to a "RC(=O)N(R$_A$)—" group in which R and R$_A$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. An N-amido may be substituted or an unsubstituted.

A "urea" group refers to a "—N(R$_A$R$_B$)—C(=O)—N(R$_A$R$_B$)—" group in which R$_A$ and R$_B$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. A urea group may be substituted or an unsubstituted.

A "thiourea" group refers to a "—N(R$_A$R$_B$)—C(=S)—N(R$_A$R$_B$)—" group in which R$_A$ and R$_B$ can be independently hydrogen, alkyl, alkenyl, alkynyl, cycloalkyl, cycloalkenyl, cycloalkynyl, aryl, heteroaryl, heterocyclyl, aralkyl, or (heterocyclyl)alkyl, as defined above. A thiourea group may be substituted or an unsubstituted.

The term "halogen atom" or "halogen" as used herein, means any one of the radio-stable atoms of column 7 of the Periodic Table of the Elements, such as, fluorine, chlorine, bromine, and iodine.

In all of the definitions described herein, the terms used to define a new term are as previously defined herein.

Where the numbers of substituents is not specified (e.g., haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two, or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, *Biochem.* 11:942-944 (1972)).

The terms "protecting group" and "protecting groups" as used herein refer to any atom or group of atoms that is added to a molecule in order to prevent existing groups in the molecule from undergoing unwanted chemical reactions. Examples of protecting group moieties are described in T. W. Greene and P. G. M. Wuts, *Protective Groups in Organic Synthesis*, 3. Ed. John Wiley & Sons, 1999, and in J. F. W. McOmie, *Protective Groups in Organic Chemistry* Plenum Press, 1973, both of which are hereby incorporated by reference for the limited purpose of disclosing suitable protecting groups. The protecting group moiety may be chosen in such a way, that they are stable to certain reaction conditions and readily removed at a convenient stage using methodology known from the art. A non-limiting list of protecting groups include benzyl; substituted benzyl; alkylcarbonyls (e.g., t-butoxycarbonyl (BOC), acetyl, or isobutyryl); arylalkylcarbonyls (e.g., benzyloxycarbonyl or benzoyl); substituted methyl ether (e.g., methoxymethyl ether); substituted ethyl ether; a substituted benzyl ether; tetrahydropyranyl ether; silyl ethers (e.g., trimethylsilyl, triethylsilyl, triisopropylsilyl, t-butyldimethylsilyl, or t-butyldiphenylsilyl); esters (e.g., benzoate ester); carbonates (e.g., methoxymethylcarbonate); sulfonates (e.g., tosylate or mesylate); acyclic ketal (e.g., dimethyl acetal); cyclic ketals (e.g., 1,3-dioxane or 1,3-dioxolanes); acyclic acetal; cyclic acetal; acyclic hemiacetal; cyclic hemiacetal; cyclic dithioketals (e.g., 1,3-dithiane or 1,3-dithiolane); and triarylmethyl groups (e.g., trityl; monomethoxytrityl (MMTr); 4,4'-dimethoxytrityl (DMTr); or 4,4',4"-trimethoxytrityl (TMTr)).

"Leaving group" as used herein refers to any atom or moiety that is capable of being displaced by another atom or moiety in a chemical reaction. More specifically, in some embodiments, "leaving group" refers to the atom or moiety that is displaced in a nucleophilic substitution reaction. In some embodiments, "leaving groups" are any atoms or moieties that are conjugate bases of strong acids. Examples of suitable leaving groups include, but are not limited to, tosylates and halogens. Non-limiting characteristics and examples of leaving groups can be found, for example in *Organic Chemistry*, 2d ed., Francis Carey (1992), pages 328-331; *Introduction to Organic Chemistry*, 2d ed., Andrew Streitwieser and Clayton Heathcock (1981), pages 169-171; and *Organic Chemistry*, 5$^{th}$ ed., John McMurry (2000), pages 398 and 408; all of which are incorporated herein by reference for the limited purpose of disclosing characteristics and examples of leaving groups.

The term "pharmaceutically acceptable salt" as used herein is a broad term, and is to be given its ordinary and customary meaning to a person of ordinary skill in the art (and is not to be limited to a special or customized meaning), and refers without limitation to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid, and phosphoric acid. Pharmaceutical salts can also be obtained by reacting a compound with an organic acid such as aliphatic or aromatic carboxylic or sulfonic acids, for example formic acid, acetic acid, propionic acid, glycolic acid, pyruvic acid, malonic acid, maleic acid, fumaric acid, trifluoroacetic acid, benzoic acid, cinnamic acid, mandelic acid, succinic acid, lactic acid, malic acid, tartaric acid, citric acid, ascorbic acid, nicotinic acid, methanesulfonic acid, ethanesulfonic acid, p-toluenesulfonic acid, salicylic acid, stearic acid, muconic acid, butyric acid, phenylacetic acid, phenylbutyric acid, valproic acid, 1,2-ethanedisulfonic acid, 2-hydroxyethanesulfonic acid, benzenesulfonic acid, 2-naphthalenesulfonic acid, or naphthalenesulfonic acid. Pharmaceutical salts can also be obtained by reacting a compound with a base to form a salt such as an ammonium salt, an alkali metal salt, such as a lithium, sodium or a potassium salt, an alkaline earth metal salt, such as a calcium, magnesium or aluminum salt, a salt of organic bases such as dicyclohexylamine, N-methyl-D-glucamine, tris(hydroxymethyl)methylamine, $C_1$-$C_7$ alkylamine, cyclohexylamine, dicyclohexylamine, triethanolamine, ethylenediamine, ethanolamine, diethanolamine, triethanolamine, tromethamine, and salts with amino acids such as arginine and lysine; or a salt of an inorganic base, such as aluminum hydroxide, calcium hydroxide, potassium hydroxide, sodium carbonate, sodium hydroxide, or the like.

The term "solvate" as used herein is a broad term, and is to be given its ordinary and customary meaning to a person of ordinary skill in the art (and is not to be limited to a special or customized meaning), and refers without limitation to mean that the solvent is complexed with a compound in a reproducible molar ratio, including, but not limited to, 0.5:1, 1:1, or 2:1. Thus, the term "pharmaceutically acceptable solvate," refers to a solvate wherein the solvent is one that does not cause significant irritation to an organism to which it is administered and does not abrogate the biological activity and properties of the compound.

The term "prodrug" as used herein is a broad term, and is to be given its ordinary and customary meaning to a person of ordinary skill in the art (and is not to be limited to a special or customized meaning), and refers without limitation to a compound or a pharmaceutical composition that can be administered to a patient in a less active or inactive form, which can then be metabolized in vivo into a more active metabolite. In certain embodiments, upon in vivo administration, a prodrug is chemically converted to the biologically, pharmaceutically, or therapeutically active form of the compound. In certain embodiments, a prodrug is enzymatically metabolized by one or more steps or processes to the biologically, pharmaceutically, or therapeutically active form of the compound.

It is understood that, in any compound described herein having one or more chiral centers, if an absolute stereochemistry is not expressly indicated, then each center may independently be of R-configuration or S-configuration or a mixture thereof. Thus, the compounds provided herein may be enantiomerically pure, enantiomerically enriched, or may be stereoisomeric mixtures, and include all diastereomeric, and enantiomeric forms. In addition it is understood that, in any compound described herein having one or more double bond(s) generating geometrical isomers that can be defined as E or Z, each double bond may independently be E or Z a mixture thereof. Stereoisomers are obtained, if desired, by methods such as, stereoselective synthesis and/or the separation of stereoisomers by chiral chromatographic columns.

Likewise, it is understood that, in any compound described, all tautomeric forms are also intended to be included.

Wherever a substituent is depicted as a di-radical (i.e., has two points of attachment to the rest of the molecule), it is to be understood that the substituent can be attached in any directional configuration unless otherwise indicated. Thus, for example, a substituent depicted as -AE- or

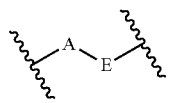

includes the substituent being oriented such that the A is attached at the leftmost attachment point of the molecule as well as the case in which A is attached at the rightmost attachment point of the molecule.

It is to be understood that where compounds disclosed herein have unfilled valencies, then the valencies are to be filled with hydrogens and/or deuteriums.

It is understood that the compounds described herein can be labeled isotopically or by another other means, including, but not limited to, the use of chromophores or fluorescent moieties, bioluminescent labels, or chemiluminescent labels. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium), hydrogen-2 (deuterium), and hydrogen-3 (tritium). Thus, reference herein to a compound encompasses all potential isotopic forms unless the context clearly dictates otherwise.

It is understood that the methods and formulations described herein include the use of crystalline forms, amorphous phases, and/or pharmaceutically acceptable salts, solvates, hydrates, and conformers of compounds of preferred embodiments, as well as metabolites and active metabolites of these compounds having the same type of activity. A conformer is a structure that is a conformational isomer. Conformational isomerism is the phenomenon of molecules with the same structural formula but different conformations (conformers) of atoms about a rotating bond. In specific embodiments, the compounds described herein exist in solvated forms with pharmaceutically acceptable solvents such as water, ethanol, or the like. In other embodiments, the compounds described herein exist in unsolvated form. Solvates contain either stoichiometric or non-stoichiometric amounts of a solvent, and may be formed during the process of crystallization with pharmaceutically acceptable solvents such as water, ethanol, or the like. Hydrates are formed when the solvent is water, or alcoholates are formed when the solvent is alcohol. In addition, the compounds provided herein can exist in unsolvated as well as solvated forms. In general, the solvated forms are considered equivalent to the unsolvated forms for the purposes of the compounds and methods provided herein. Other forms in which the compounds of preferred embodiments can be provided include amorphous forms, milled forms and nano-particulate forms.

Likewise, it is understood that the compounds described herein, such as compounds of preferred embodiments, include the compound in any of the forms described herein (e.g., pharmaceutically acceptable salts, prodrugs, crystalline forms, amorphous form, solvated forms, enantiomeric forms, tautomeric forms, and the like).

Additional Therapeutic Agents

Some embodiments provide pharmaceutical compositions comprising a compound of Formula (I) and a pharmaceutically acceptable carrier. Some embodiments provide pharmaceutical compositions comprising a compound of Formula (I), a pharmaceutically acceptable carrier, and a second therapeutic agent. Some embodiments provide methods of inhibiting GSPT1 activity, comprising contacting a cell with a compound of Formula (I). Some embodiments provide methods of treating, ameliorating, or preventing a disease, disorder, or condition associated with a protein selected from a cytokine, ailios, ikaros, helios, CK1-alpha, and combinations of any of the foregoing, the method comprising administering a therapeutically effective amount of a compound Formula (I), or a pharmaceutically acceptable salt thereof. In some embodiments, the disease, disorder, or condition is selected from the group consisting of inflammation, fibromyalgia, rheumatoid arthritis, osteoarthritis, ankylosing spondylitis, psoriasis, psoriatic arthritis, inflammatory bowel diseases, Crohn's disease, ulcerative colitis, uveitis, inflammatory lung diseases, chronic obstructive pulmonary disease, Alzheimer's disease, and cancer. In some embodiments, the compound of Formula (I) is administered in combination with a second therapeutic agent. In some embodiments, the second therapeutic agent is selected from the group consisting of anti-inflammatory agents, anti-cancer agents, immunostimulatory agents, and immunosuppressive agents. In some embodiments, the second therapeutic agent is an anti-cancer agent. Some embodiments provide methods of inhibiting protein activity, comprising contacting a cell with a compound of Formula (I), or a pharmaceutically acceptable salt thereof, wherein the protein is ailios, ikaros, helios, CK1α, a cytokine, or a combination of any of the foregoing. Some embodiments provide methods of decreasing the risk of skin cancer in a subject in need thereof, comprising administering an effective amount of a compound of Formula (I), or a pharmaceutically acceptable salt thereof. Some embodiments provide methods for treating, ameliorating, or preventing a skin disorder, disease, or condition in a subject, comprising administering to the subject a therapeutically effective amount of a compound of Formula (I), or a pharmaceutically acceptable salt thereof. In some embodiments, the skin disorder, disease, or condition is sunburn or skin hypopigmentation. Some embodiments provide methods for treating, ameliorating, or preventing a skin disorder, disease, or condition in a subject, comprising administering to the subject a therapeutically effective amount of a compound of Formula (I), or a pharmaceutically acceptable salt thereof. Some embodiments provide methods for increasing skin pigmentation in a subject in need thereof, comprising administering a therapeutically effective amount of a compound of Formula (I), or a pharmaceutically acceptable salt thereof. In some embodiments, the administering comprises contacting the skin with a therapeutically effective amount of Formula (I), or a pharmaceutically acceptable salt thereof. Some embodiments provide methods for increasing eumelanin level in a subject in need thereof, comprising administering a therapeutically effective amount of a compound of Formula (I), or a pharmaceutically acceptable salt thereof. In some embodiments, administering comprises contacting the skin with a therapeutically effective amount of a compound of Formula (I), or a pharmaceutically acceptable salt thereof. Some embodiments provide methods for increasing p53 activity, comprising contacting a cell with a compound of Formula (I), or a pharmaceutically acceptable salt thereof. Some embodiments provide methods for decreasing MDM2 activity, comprising contacting a cell with a compound of Formula (I), or a pharmaceutically acceptable salt thereof.

In some embodiments described herein, for example, in the previous paragraph, the compound of Formula (I) is administered with a second therapeutic agent. In some embodiments described herein, for example, in the previous paragraph, the composition comprising Formula (I) also comprises a second therapeutic agent. For example, Some embodiments provide methods of treating, ameliorating, or preventing a disease, disorder, or condition associated with GSPT1 function or imbalance, comprising administering a therapeutically effective amount of a compound of Formula (I), to a subject in need thereof. Some embodiments provide methods of treating, ameliorating, or preventing a disease, disorder, or condition associated with GSPT1 function or imbalance, comprising administering a therapeutically effective amount of a compound of Formula (I) in combination with a second therapeutic agent.

In some embodiments, the second therapeutic agent is anti-inflammatory agent. In some embodiments, the second therapeutic agent is a non-steroidal anti-inflammatory agent. In some embodiments, the second therapeutic agent is an anti-cancer agent. In some embodiments, the second therapeutic agent is an immunostimulatory agent. In some embodiments, the second therapeutic agent is an immunosuppressive agent. In some embodiments, the second therapeutic agent is antibody.

In some embodiments, the second therapeutic agent is selected from aspirin; diflunisal; salsalate; acetaminophen; ibuprofen; dexibuprofen; naproxen; fenoprofen; ketoprofen; dexketoprofen; flurbiprofen; oxaprozin; loxoprofen; indomethacin; tolmetin; sulindac; etodolac; ketorolac; diclofenac; aceclofenac; nabumetone; enolic acid; piroxicam; meloxicam; tenoxicam; droxicam; lornoxicam; isoxicam; mefenamic acid; meclofenamic acid; flufenamic acid; tolfenamic acid; sulfonanilides; clonixin; licofelone; dexamethasone; and prednisone.

In some embodiments, the second therapeutic agent is selected from mechlorethamine; cyclophosphamide; melphalan; chlorambucil; ifosfamide; busulfan; N-nitroso-N-methylurea (MNU); carmustine (BCNU); lomustine (CCNU); semustine (MeCCNU); fotemustine; streptozotocin; dacarbazine; mitozolomide; temozolomide; thiotepa; mytomycin; diaziquone (AZQ); cisplatin; carboplatin; and oxaliplatin.

In some embodiments, the second therapeutic agent is selected from vincristine; vinblastine; vinorelbine; vindesine; vinflunine; paclitaxel; docetaxel; etoposide; teniposide; tofacitinib; ixabepilone; irinotecan; topotecan; camptothecin; doxorubicin; mitoxantrone; and teniposide.

In some embodiments, the second therapeutic agent is selected from actinomycin; bleomycin; plicamycin; mitomycin; daunorubicin; epirubicin; idarubicin; pirarubicin; aclarubicin; mitoxantrone; cyclophosphamide; methotrexate; 5-fluorouracil; prednisolone; folinic acid; methotrexate; melphalan; capecitabine; mechlorethamine; uramustine; melphalan; chlorambucil; ifosfamide; bendamustine; 6-mercaptopurine; and procarbazine.

In some embodiments, the second therapeutic agent is selected from cladribine; pemetrexed; fludarabine; gemcitabine; hydroxyurea; nelarabine; cladribine; clofarabine; ytarabine; decitabine; cytarabine; cytarabine liposomal; pralatrexate; floxuridine; fludarabine; colchicine; thioguanine; cabazitaxel; larotaxel; ortataxel; tesetaxel; aminopterin; pemetrexed; pralatrexate; raltitrexed; pemetrexed; carmofur; and floxuridine.

In some embodiments, the second therapeutic agent is selected from azacitidine; decitabine; hydroxycarbamide; topotecan; irinotecan; belotecan; teniposide; aclarubicin; epirubicin; idarubicin; amrubicin; pirarubicin; valrubicin; zorubicin; mitoxantrone; pixantrone; mechlorethamine; chlorambucil; prednimustine; uramustine; estramustine; carmustine; lomustine; fotemustine; nimustine; ranimustine; carboquone; thioTEPA; triaziquone; and triethylenemelamine.

In some embodiments, the second therapeutic agent is selected from nedaplatin; satraplatin; procarbazine; dacarbazine; temozolomide; altretamine; mitobronitol; pipobroman; actinomycin; bleomycin; plicamycin; aminolevulinic acid; methyl aminolevulinate; efaproxiral; talaporfin; temoporfin; verteporfin; alvocidib; seliciclib; palbociclib; bortezomib; carfilzomib; anagrelide; masoprocol; olaparib; belinostat; panobinostat; romidepsin; vorinosta; idelalisib; atrasentan; bexarotene; testolactone; amsacrine; trabectedin; alitretinoin; tretinoin; demecolcine; elsamitrucin; etoglucid; lonidamine; lucanthone; mitoguazone; mitotane; oblimersen; omacetaxine mepesuccinate; and eribulin.

In some embodiments, the second therapeutic agent is selected from azathioprine; Mycophenolic acid; leflunomide; teriflunomide; tacrolimus; cyclosporin; pimecrolimus; abetimus; gusperimus; lenalidomide; pomalidomide; thalidomide; anakinra; sirolimus; everolimus; ridaforolimus; temsirolimus; umirolimus; zotarolimus; eculizumab; adalimumab; afelimomab; certolizumab pegol; golimumab; infliximab; nerelimomab; mepolizumab; omalizumab; faralimomab; elsilimomab; lebrikizumab; ustekinumab; etanercept; otelixizumab; teplizumab; visilizumab; clenoliximab; keliximab; zanolimumab; efalizumab; erlizumab; obinutuzumab; rituximab; and ocrelizumab.

In some embodiments, the second therapeutic agent is selected from pascolizumab; gomiliximab; lumiliximab; teneliximab; toralizumab; aselizumab; galiximab; gavilimomab; ruplizumab; belimumab; blisibimod; ipilimumab; tremelimumab; bertilimumab; lerdelimumab; metelimumab; natalizumab; tocilizumab; odulimomab; basiliximab; daclizumab; inolimomab; zolimoma; atorolimumab; cedelizumab; fontolizumab; maslimomab; morolimumab; pexelizumab; reslizumab; rovelizumab; siplizumab; talizumab; telimomab; vapaliximab; vepalimomab; abatacept; belatacept; pegsunercept; aflibercept; alefacept; and rilonacept.

Dosing Regimes

In some embodiments, about 1 mg to about 5 grams; 2 mg to 2 gram; 5 mg to about 1 gram; 10 mg to about 800 mg; 20 mg to 600 mg; 30 mg to 400 mg; 40 mg to 200 mg; 50 mg to 100 mg of a compound of Formula (I), or any amount in between, is administered each day. In some embodiments, about 1 mg to about 5 grams; 2 mg to 2 gram; 5 mg to about 1 gram; 10 mg to about 800 mg; 20 mg to 600 mg; 30 mg to 400 mg; 40 mg to 200 mg; 50 mg to 100 mg of a compound of Formula (I), or any amount in between, is administered each week. In some embodiments, about 1 mg to about 5 grams; 2 mg to 2 gram; 5 mg to about 1 gram; 10 mg to about 800 mg; 20 mg to 600 mg; 30 mg to 400 mg; 40 mg to 200 mg; 50 mg to 100 mg of a compound of Formula (I), or any amount in between, is administered each cycle of treatment.

In some embodiments, a compound of Formula (I) is administered at least once per day, at least twice per day, at least three times per day, or at least four times per day. In some embodiments, a compound of Formula (I) is administered at least once per day, at least twice per day, at least three times per day, or at least four times per week. In some embodiments, each cycle of treatment lasts 1, 2, 3, 4, 5, 6, 7, 8, 9, 10, 11, 12, 13, or 14 days, or any value in between. In some embodiments, each cycle of treatment has at least 1, 2, 3, 4, 5, 6, or 7 days between administrations of a compound of Formula (I), or any value in between.

In some embodiments, a compound of Formula (I) is provided intravenously over about 10, 20, 30, 40, 50, 60, 90, 120, 150, 180, 210, or 240 minutes, or any value in between.

EXAMPLES

Additional embodiments are disclosed in further detail in the following examples, which are not in any way intended to limit the scope of the claims.

Characterization of the compounds disclosed herein was performed with Bruker AV-500 and Bruker DRX-500 NMR spectrometers and a Perkin Elmer PE-SCIEX API-150 mass spectrometer.

Synthesis (S)-3-(5-{[3-(3-Chlorotolyl)ureido]methyl}-2-isoindolinoyl)-2,7-azepanedione (Compound 1)

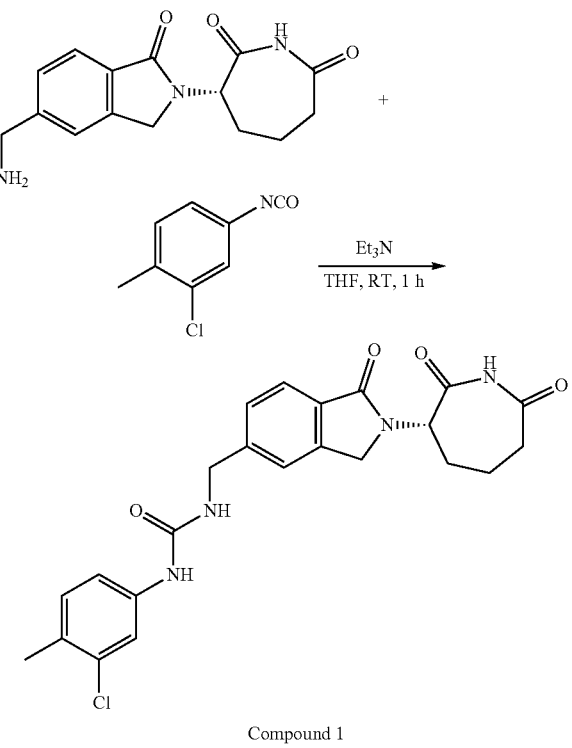

Compound 1

To a suspension of (S)-3-[5-(aminomethyl)-2-isoindolinoyl]-2,7-azepanedione trifluoroacetic acid salt (67.5 mg, 0.168 mmol) in tetrahydrofuran (6 mL) was added triethylamine (33.9 mg, 0.336 mmol), followed by 2-chloro-4-isocyanato-1-methylbenzene (31 mg, 0.185 mmol). The solution was stirred at rt for 1 h, the solvent was removed under vacuum, and the residue was purified by silica gel column chromatography using DCM/MeOH (0% to 4%) to afford Compound 1 as an off-white solid (40.5 mg, 53.1%).

MS (m+1): 455.0. ¹H NMR (DMSO-d6) δ 10.7 (s, 1H), 8.77 (s, 1H), 7.69 (m, 2H), 7.14-7.54 (m, 4H), 6.79 (t, 1H), 5.26 (d, 1H), 4.52 (s, 2H), 4.41 (d, 2H), 3.12 (m, 1H), 2.60 (m, 1H), 2.11 (s, 4H), 2.08 (m, 2H), 1.78 (m, 1H).

(S)-3-(5-{[3-(p-Tolyl)ureido]methyl}-2-isoindolinoyl)-2,7-azepanedione (Compound 2)

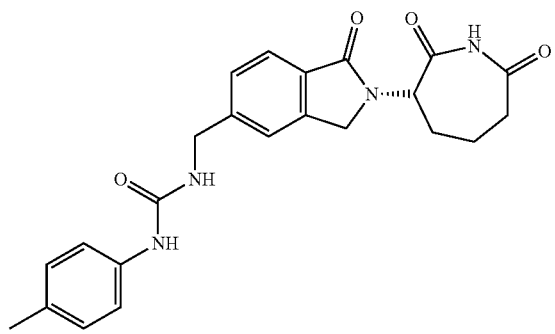

Compound 2 was afforded as an off-white solid (46.2 mg, 58%) using the methods described above for 1. MS (m+1): 421.0. ¹H NMR (DMSO-d6) δ 10.7 (s, 1H), 8.50 (s, 1H), 7.69 (m, 1H), 7.52 (s, 1H), 7.44 (d, 1H), 7.27 (d, 2H), 7.03 (d, 2H), 6.67 (t, 1H), 5.25 (d, 1H), 4.51 (s, 2H), 4.41 (d, 2H), 3.11 (m, 1H), 2.55 (m, 1H), 2.26 (s, 4H), 2.08 (m, 2H), 1.78 (m, 1H).

(S)-3-(5-{[3-(m-Chlorophenyl)ureido]methyl}-2-isoindolinoyl)-2,7-azepanedione (Compound 3)

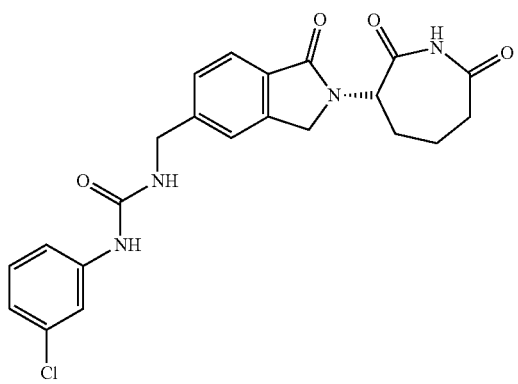

Compound 3 was afforded as an off-white solid (41.1 mg, 54%) using the methods described above for 1. MS (m+1): 440.9. 1H NMR (DMSO-d6) δ 10.7 (s, 1H), 8.91 (s, 1H), 7.71 (m, 2H), 7.54 (s, 2H), 7.45 (s, 1H), 7.25 (d, 2H), 6.96 (m, 1H), 6.88 (t, 1H), 5.23 (d, 1H), 4.52 (s, 2H), 4.42 (d, 2H), 3.06 (m, 1H), 2.51 (m, 1H), 2.29 (s, 1H), 2.25 (m, 2H), 1.80 (m, 1H).

(S)-1-((2-(2,7-dioxoazepan-3-yl)-1-oxoisoindolin-5-yl)methyl)-3-propylurea (Compound 4)

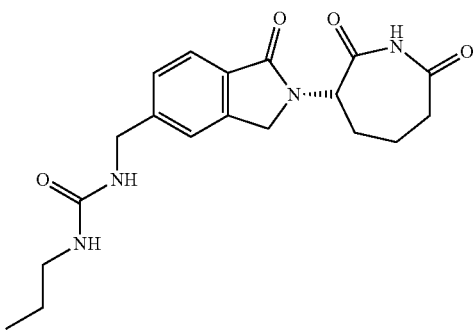

To a solution of (S)-3-(5-(aminomethyl)-1-oxoisoindolin-2-yl)azepane-2,7-dione (TFA salt) (55.6 mg, 0.194 mmol) in THF (6 mL) at RT was added 1-isocyanatopropane (18 mg, 0.21 mmol), followed by TEA (39.2 mg, 0.388 mmol). The suspension was stirred at RT for 2 h. The solvent was removed and the residue was purified by silica gel chromatography eluting with DCM/MeOH from 0% to 6% to give Compound 4 (50.2 mg, 69.6%) as a white solid. MS (ESI) m/z 373.0 [M+H]⁺. ¹H NMR (400 MHz, DMSO-d₆) δ 10.72 (s, 1H), 7.66 (d, J=58.0 Hz, 1H), 7.46 (s, 1H), 7.37 (d, J=8.0 Hz, 1H), 6.41 (t, J=5.2 Hz, 1H), 5.99 (t, J=5.6 Hz, 1H), 5.23 (dd, J=5.6, 12.4 Hz, 1H), 4.50 (s, 2H), 4.31 (d, J=6.0 Hz, 2H), 3.12-3.05 (m, 1H), 2.99 (q, J=6.4 Hz, 2H), 2.57 (d, J=16.8 Hz, 1H), 2.29-2.24 (m, 1H), 2.13-1.99 (m, 2H), 1.84-1.81 (m, 1H), 1.38 (q, J=6.0 Hz, 2H), 0.84 (t, J=7.2 Hz, 3H).

(S)-1-(3-chloro-2-methylphenyl)-3-((2-(2,7-dioxoazepan-3-yl)-1-oxoisoindolin-5-yl)methyl)urea (Compound 5)

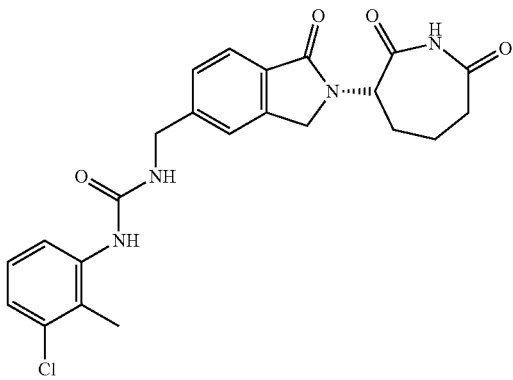

To a solution of (S)-3-(5-(aminomethyl)-1-oxoisoindolin-2-yl)azepane-2,7-dione (TFA salt) (60 mg, 0.21 mmol) in THF (3 mL) at 0° C. was added 1-chloro-3-isocyanato-2-methylbenzene (38.5 mg, 0.23 mmol) and TEA (42.4 mg, 0.42 mmol). The mixture was warmed to RT and stirred 2 h, then concentrated and purified by silica gel chromatography eluting with MeOH/DCM from 0% to 6% to give Compound 5 (27.0 mg, 28.1%) as white solid. MS (ESI) m/z 455.0, 457.0 [M+H]⁺. ¹H NMR (400 MHz, DMSO-d₆) δ 10.74 (s, 1H), 8.04 (s, 1H), 7.75 (d, J=8.0 Hz, 1H), 7.70 (d, J=8.0 Hz, 1H), 7.54 (s, 1H), 7.45 (d, J=7.6 Hz, 1H), 7.17-7.07 (m, 3H), 5.24 (dd, J=6.8, 12.0 Hz, 1H), 4.52 (s, 2H), 4.43 (d, J=5.6 Hz, 2H), 3.13-3.06 (m, 1H), 2.59-2.55 (m, 1H), 2.31-2.27 (m, 4H), 2.13-1.96 (m, 2H), 1.84-1.80 (m, 1H).

(S)-1-(3-chloro-4-fluorophenyl)-3-((2-(2,7-dioxoazepan-3-yl)-1-oxoisoindolin-5-yl)methyl) urea (Compound 6)

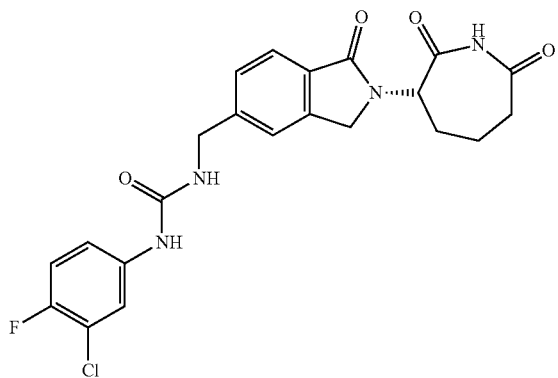

To a solution of (S)-3-(5-(aminomethyl)-1-oxoisoindolin-2-yl)azepane-2,7-dione (TFA Salt) (55.6 mg, 0.194 mmol) in THF (6 mL) at RT was added 2-chloro-1-fluoro-4-isocyanatobenzene (36.5 mg, 0.213 mmol), followed by TEA (39.2 mg, 0.388 mmol) was added. The suspension was stirred at 25° C. for 2 h. The solvent was removed and the residue was purified by silica gel chromatography eluting with DCM/MeOH from 0% to 6% to give Compound 6 (47.7 mg, 53.7%) as a white solid. MS (ESI) m/z 459.0 [M+H]⁺. ¹H NMR (400 MHz, DMSO-d₆) δ 10.73 (s, 1H), 8.90 (s, 1H), 7.79 (d, J=5.2 Hz, 1H), 7.69 (d, J=8.0 Hz, 1H), 7.53 (s, 1H), 7.74 (d, J=7.6 Hz, 1H), 7.30-7.26 (m, 2H), 6.88 (t, J=5.2 Hz, 1H), 5.24 (dd, J=4.8, 12.0 Hz, 1H), 4.51 (s, 2H), 4.41 (d, J=5.6 Hz, 2H), 3.09 (t, J=10.2 Hz, 1H), 2.57 (d, J=16.8 Hz, 1H), 2.29-2.22 (m, 1H), 2.13-2.00 (m, 2H), 1.84-1.80 (m, 1H).

(S)-2-(3-chloro-4-methylphenyl)-N-((2-(2,7-dioxoazepan-3-yl)-1-oxoisoindolin-5-yl)methyl)acetamide (Compound 7)

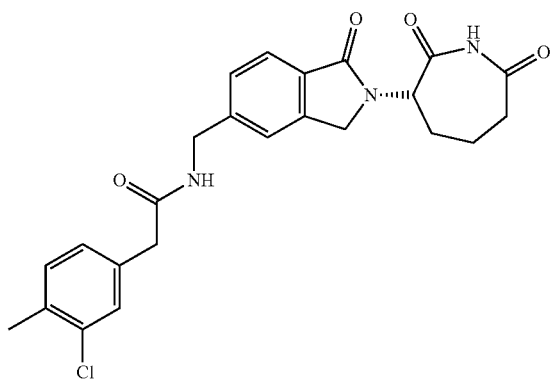

To a solution of 2-(3-chloro-4-methylphenyl)acetic acid (33 mg, 0.181 mmol) in DMF (5 mL) at RT was added HOBt (37.5 mg, 0.27 mmol) and EDCI (52.2 mg, 0.272 mmol), followed by DIEA (46.7 mg, 0.362 mmol). Then (S)-3-(5-(aminomethyl)-1-oxoisoindolin-2-yl)azepane-2,7-dione (TFA salt) (51.9 mg, 0.181 mmol) was added and the mixture was stirred at RT for 16 h. The reaction was diluted with water (10 mL), extracted with EA (20 mL×2). The combined organic layers were concentrated and purified by silica gel chromatography eluting with DCM/MeOH from 0% to 4% and triturated with EA (5 mL) to give Compound 7 (53 mg, 64.7%) as a white solid. MS (ESI) m/z 454.0 [M+H]⁺. ¹H NMR (400 MHz, DMSO-d₆) δ 10.75 (s, 1H), 8.70 (t, J=5.6 Hz, 1H), 7.67 (d, J=8.0 Hz, 1H), 7.44 (s, 1H), 7.38 (d, J=7.6 Hz, 1H), 7.34 (s, 1H), 7.29 (d, J=7.6 Hz, 1H), 7.15 (d, J=6.8 Hz, 1H), 5.24 (dd, J=4.4, 12.0 Hz, 1H), 4.49 (s, 2H), 4.39 (d, J=5.6 Hz, 2H), 3.49 (s, 2H), 3.09-3.06 (m, 1H), 2.58 (d, J=17.2 Hz, 1H), 2.31 (s, 1H), 2.28-2.26 (m, 1H), 2.14-2.01 (m, 2H), 1.88-1.77 (m, 1H).

(S)-1-(3-chloro-4-methoxyphenyl)-3-((2-(2,7-dioxoazepan-3-yl)-1-oxoisoindolin-5-yl)methyl)urea (Compound 8)

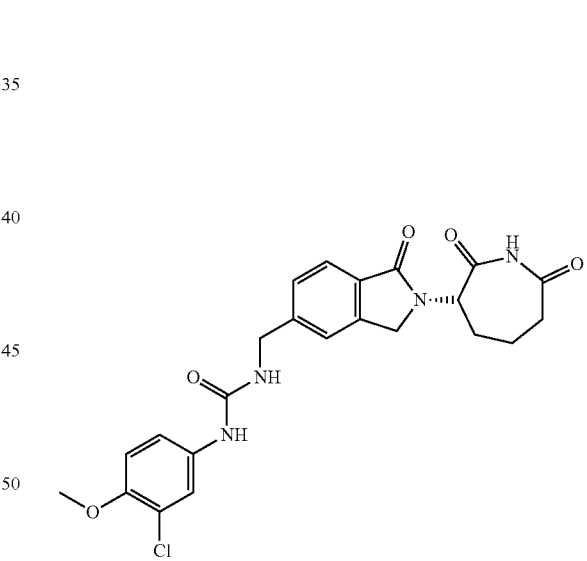

To a solution of (S)-3-(5-(aminomethyl)-1-oxoisoindolin-2-yl)azepane-2,7-dione (TFA salt) (37 mg, 0.13 mmol) in DMF (4 mL) was added CDI (20.9 mg, 0.13 mmol) and the suspension was stirred at RT for 14 h. Then 3-chloro-4-methoxyaniline (20.3 mg, 0.13 mmol) was added and the reaction stirred at RT for 8 h. The suspension was diluted with water, extracted with DCM. The combined organic layers were dried over sodium sulfate, filtered and concentrated to give the crude product, which was purified by silica gel chromatography eluting with MeOH/DCM from 0% to 10% to give Compound 8 (28.0 mg, 46%) as a white solid. MS (ESI) m/z 471.1 [M+H]$^+$. $^1$H NMR (400 MHz, DMSO-$d_6$) δ 10.72 (s, 1H), 8.64 (s, 1H), 7.68 (d, J=7.6 Hz, 1H), 7.64 (d, J=2.4 Hz, 1H), 7.52 (s, 1H), 7.43 (d, J=7.6 Hz, 1H), 7.20 (dd, J=2.4, 8.8 Hz, 1H), 7.03 (d, J=9.2 Hz, 1H), 6.75 (t, J=6 Hz, 1H), 5.25-5.21 (m, 1H), 4.51 (s, 2H), 4.40 (d, J=7.2 Hz, 2H), 3.78 (s, 3H), 3.12-3.05 (m, 1H), 2.59-2.55 (m, 1H), 2.28-2.22 (m, 1H), 2.12-1.98 (m, 2H), 1.84-1.79 (m, 1H).

(S)—N-((2-(2,7-dioxoazepan-3-yl)-1-oxoisoindolin-5-yl)methyl)-2-(p-tolyl)acetamide (Compound 9)

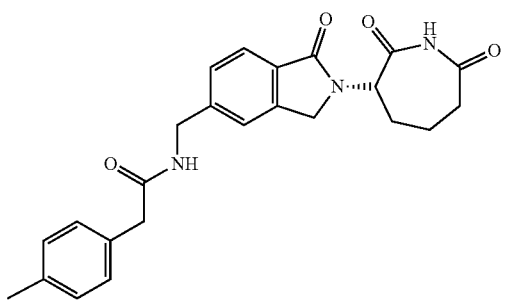

To a solution of 2-(p-tolyl)acetic acid (27.2 mg, 0.18 mmol) in DMF (5 mL) was added HOBt (37.4 mg, 0.27 mmol) and EDCI (52.1 mg, 0.27 mmol), followed by DIEA (58.0 mg, 0.36 mmol) and (S)-3-(5-(aminomethyl)-1-oxoisoindolin-2-yl)azepane-2,7-dione (TFA salt) (51.7 mg, 0.18 mmol). The solution was stirred at RT for 16 h, diluted with water (10 mL), extracted with EA (20 mL×2). The combined organic layers were concentrated to give the crude product, which was purified by silica gel chromatography eluting with MeOH/DCM from 0% to 10% to give (Compound 9 (61.0 mg, 80.1%) as white solid. MS (ESI) m/z 420.0 [M+H]$^+$. $^1$H NMR (400 MHz, DMSO-d6) δ 10.74 (s, 1H), 8.63 (t, J=5.6 Hz, 1H), 7.67 (d, J=7.6 Hz, 1H), 7.43 (s, 1H), 7.37 (d, J=8.0 Hz, 1H), 7.18 (d, J=8.0 Hz, 2H), 7.12 (d, J=8.0 Hz, 2H), 5.24 (dd, J=7.2, 12.0 Hz, 1H), 4.49 (s, 2H), 4.38 (d, J=5.6 Hz, 2H), 3.46 (s, 2H), 3.13-3.06 (m, 1H), 2.61-2.57 (m, 1H), 2.28-2.23 (m, 4H), 2.13-2.01 (m, 2H), 1.86-1.81 (m, 1H).

(S)-2-(3-chloro-4-(trifluoromethyl)phenyl)-N-((2-(2,7-dioxoazepan-3-yl)-1-oxoisoindolin-5-yl)methyl)acetamide (Compound 10)

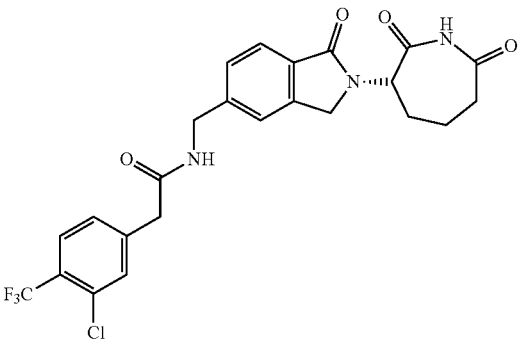

The solution of 3-chloro-4-(trifluoromethyl)benzoic acid (920 mg, 4.09 mmol) in thionyl chloride (5 mL) was heated at 80° C. for 1 h. The solvent was removed and the residue was dried in vacuo to give 3-chloro-4-(trifluoromethyl) benzoyl chloride as a white solid, which was dissolved in THF (10 mL) and cooled to 0° C. Trimethylsilyldiazomethane (3.07 mL, 6.14 mmol, 2M in hexane) was added, followed by TEA (620.1 mg, 6.14 mmol). The mixture was stirred at RT for 18 h, poured NaHCO$_3$ (sat, 10 mL) and extracted with EA (30 mL×2). The combined organic layers were dried over sodium sulfate, filtered and concentrated to give the crude 1-(3-chloro-4-(trifluoromethyl)phenyl)-2-diazoethanone (833 mg, 82.5%) as a yellow solid, which was used directly for the next step without further purification.

To a mixture of (benzoyloxy)silver (229 mg, 1.00 mmol) in EtOH/toluene (30 mL/12 mL) was added TEA (1.4 mL, 10.08 mmol). The mixture was refluxed at 90° C. for 1 min and a solution of 1-(3-chloro-4-(trifluoromethyl)phenyl)-2-diazoethanone (833 mg, 3.36 mmol) in EtOH (6 mL) was added. The solution was stirred at 90° C. for 2 h, filtered and the filtrate was concentrated to give a yellow gum, which was purified by silica gel chromatography eluting with EA/petroleum ether from 0% to 10% to give ethyl 2-(3-chloro-4-(trifluoromethyl)phenyl)acetate (408 mg, 45.6%) as a yellow oil. $^1$H NMR (300 MHz, CDCl$_3$) δ 7.65 (d, J=7.8 Hz, 1H), 7.47 (s, 1H), 7.30 (d, J=8.4 Hz, 1H), 4.19 (q, J=7.2 Hz, 2H), 3.66 (s, 2H), 1.28 (t, J=7.5 Hz, 3H).

To a solution of ethyl 2-(3-chloro-4-(trifluoromethyl)phenyl)acetate (408 mg, 1.53 mmol) in EtOH (10 mL) was added NaOH (1.53 mL, 3.06 mmol, 2 M). The mixture was heated at 50° C. for 3 h. The solvent was removed and the residue was adjusted to pH=3 with 1M HCl. The solution was extracted with EA (15 mL×2). The combined organic layers were dried over sodium sulfate, filtered and concentrated to give 2-(3-chloro-4-(trifluoromethyl)phenyl)acetic acid (335 mg, 92.0%) as a yellow solid. $^1$H NMR (300 MHz, CDCl$_3$) δ 7.66 (d, J=7.6 Hz, 1H), 7.46 (s, 1H), 7.29 (d, J=8.4 Hz, 1H), 3.70 (s, 2H).

To a solution of 2-(3-chloro-4-(trifluoromethyl)phenyl) acetic acid (46.1 mg, 0.194 mmol) in DMF (5 mL) at RT was added HOBt (41 mg, 0.291 mmol) and EDCI (56 mg, 0.291 mmol), followed by DIEA (45.1 mg, 0.35 mmol). (S)-3-(5-(aminomethyl)-1-oxoisoindolin-2-yl)azepane-2,7-dione (TFA salt) (55.6 mg, 0.194 mmol) was added and the solution was stirred at RT for 16 h. The reaction was diluted with water (10 mL), extracted with EA (20 mL×2) and the combined organic layers were concentrated and purified by silica gel chromatography eluting with DCM/MeOH from 0% to 5% to give Compound 10 (70 mg, 71.0%) as a white solid. MS (ESI) m/z 507.9 [M+H]$^+$. $^1$H NMR (400 MHz, DMSO-d$_6$) δ 10.73 (s, 1H), 8.78 (t, J=6.0 Hz, 1H), 7.81 (d, J=8.0 Hz, 1H), 7.67 (d, J=7.6 Hz, 1H), 7.65 (s, 1H), 7.47-7.45 (m, 2H), 7.39 (d, J=8.0 Hz, 1H), 5.23 (dd, J=5.2, 12.4 Hz, 1H), 4.49 (s, 2H), 4.40 (d, J=5.6 Hz, 2H), 3.65 (s, 2H), 3.13-3.04 (m, 1H), 2.58 (d, J=16.8 Hz, 1H), 2.28-2.25 (m, 1H), 2.13-2.01 (m, 2H), 1.83-1.82 (m, 1H).

(S)—N-((2-(2,7-dioxoazepan-3-yl)-1-oxoisoindolin-5-yl)methyl)-2-(4-methyl-3-(morpholinomethyl)phenyl)acetamide (Compound 11)

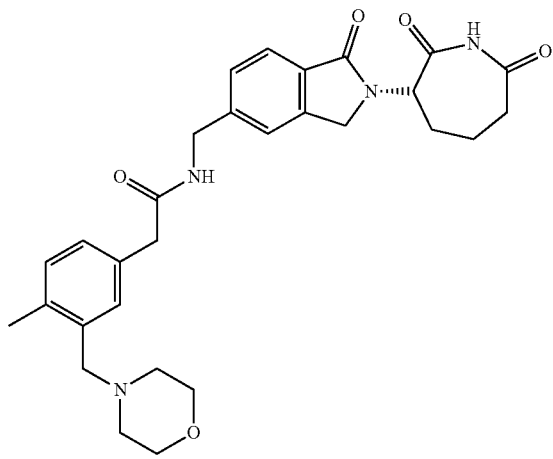

To a solution of methyl 4-bromo-3-methylbenzoate (5.0 g, 21.83 mmol) in carbon tetrachloride (120 mL) was added NBS (4.67 g, 26.20 mmol), the suspension was heated at 80° C. for 5 min. Then AIBN (1.79 g, 10.92 mmol) was added. The suspension was stirred at 80° C. for 16 h. The reaction was cooled to RT and filtered. The filtrate was concentrated and purified by silica gel chromatography eluting with EA/petroleum ether from 0% to 3% to give methyl 4-bromo-3-(bromomethyl)benzoate (4.12 g, 61.5%) as a white solid.

To a solution of methyl 4-bromo-3-(bromomethyl)benzoate (2.0 g, 6.51 mmol) in ACN (50 mL) was added morpholine (624 mg, 7.17 mmol), then DIEA (1.68 g, 13.02 mmol) was added. The reaction was stirred at RT for 1 h. The solvent was removed and the residue was purified by silica gel chromatography eluting with EA/petroleum ether from 10% to 18% to give methyl 4-bromo-3-(morpholinomethyl)benzoate (1.97 g, 96.6%) as a white solid.

To a suspension of methyl 4-bromo-3-(morpholinomethyl)benzoate (1.67 g, 5.33 mmol) in dioxane/water (60 mL/6 mL) at RT was added 2,4,6-trimethyl-cyclotriboroxane (6.8 mL, purity: 50% in THF) and potassium phosphite (3.39 g, 15.99 mmol). The suspension was purged with N$_2$ twice then [1,1'-bis(diphenylphosphino)ferrocene] dichloropalladium(II) [Pd(dppf)Cl$_2$] (779 mg, 1.07 mmol) was added. The mixture was heated at 90° C. for 18 h under N$_2$. The reaction was cooled to RT and the solvent was removed. The residue was purified by silica gel chromatography eluting with EA/MeOH from 10% to 18% to give methyl 4-methyl-3-(morpholinomethyl)benzoate (1.16 g, 87.2%) as a white solid. MS (ESI) m/z 250.1 [M+H]$^+$.

To a solution of methyl 4-methyl-3-(morpholinomethyl)benzoate (1.36 g, 5.44 mmol) in MeOH (30 mL) was added NaOH (5.44 mL, 10.88 mmol, 2 M). The mixture was heated at 50° C. for 16 h. The solvent was removed and the residue was adjusted to pH=3 with 1M HCl. A white solid formed and was filtered. The solid was dissolved in ACN (15 mL) and concentrated to give 4-methyl-3-(morpholinomethyl)benzoic acid (1.30 g, 100%) as a white solid. $^1$H NMR (400 MHz, DMSO-d$_6$) δ 13.03 (s, 1H), 10.63 (s, 1H), 8.18 (s, 1H), 7.89 (d, J=7.6 Hz, 1H), 7.42 (d, J=7.6 Hz, 1H), 4.42 (d, J=4.4 Hz, 2H), 3.94-3.78 (m, 4H), 3.32-3.16 (m, 4H), 2.53 (s, 3H).

The solution of 4-methyl-3-(morpholinomethyl)benzoic acid (365 mg, 1.55 mmol) in thionyl chloride (5 mL) was heated at 80° C. for 1 h. The solvent was removed and the residue was dried in vacuo to give 4-methyl-3-(morpholinomethyl)benzoyl chloride as a white solid.

4-Methyl-3-(morpholinomethyl)benzoyl chloride was dissolved in THF (15 mL) and cooled to 0° C. trimethylsilyldiazomethane (1.55 mL, 3.1 mmol, 2M in hexane) was added, followed by TEA (313 mg, 3.1 mmol). The mixture was stirred at RT for 18 h. The reaction was poured into NaHCO$_3$ (sat., 20 mL) and extracted with EA (30 mL×2). The combined organic layers were dried over sodium sulfate, filtered and concentrated to give the crude 2-diazo-1-(4-methyl-3-(morpholinomethyl)phenyl)ethanone (300 mg, 75%) used directly for the next step without further purification.

To a mixture of EtOH/toluene (10 mL/4 mL) was added (benzoyloxy)silver (106 mg, 0.47 mmol) and TEA (351 mg, 3.48 mmol). The mixture was refluxed at 90° C. for 1 min. The solution of 2-diazo-1-(4-methyl-3-(morpholinomethyl)phenyl)ethanone (300 mg, 1.16 mmol) in EtOH (2 mL) was added and the solution was stirred at 90° C. for 2 h. The suspension was filtered and the filtrate was concentrated to give a yellow gum, which was purified by silica gel chromatography eluting with EA/petroleum ether from 5% to 18% to give ethyl 2-(4-methyl-3-(morpholinomethyl)phenyl)acetate (110 mg, 34.4%) as a yellow oil. $^1$H NMR (300 MHz, CDCl$_3$) δ 7.19 (s, 1H), 7.12 (s, 1H), 4.15 (q, J=7.5 Hz, 2H), 3.73-3.69 (m, 4H), 3.58 (s, 2H), 3.47 (s, 2H), 2.48 (s, 4H), 2.36 (s, 3H), 1.25 (t, J=7.2 Hz, 3H).

To a solution of ethyl 2-(4-methyl-3-(morpholinomethyl)phenyl)acetate (110 mg, 0.398 mmol) in EtOH (10 mL) was added NaOH (0.4 mL, 0.796 mmol, 2 M). The mixture was heated at 50° C. for 16 h. The solvent was removed and the residue was adjusted to pH=3 with 1M HCl. The suspension was concentrated to give crude 2-(4-methyl-3-(morpholinomethyl)phenyl)acetic acid (98 mg) as a white solid. $^1$H NMR (400 MHz, DMSO-d$_6$) δ 12.39 (s, 1H), 11.19 (s, 1H), 7.55 (s, 1H), 7.23 (s, 2H), 4.31 (d, J=4.0 Hz, 2H), 3.90 (s, 4H), 3.54 (s, 2H), 3.26-3.19 (m, 4H), 2.43 (s, 3H).

To a solution of 2-(4-methyl-3-(morpholinomethyl)phenyl)acetic acid (64.2 mg, 0.258 mmol) in DMF (10 mL) at RT was added HOBt (53.4 mg, 0.387 mmol) and EDCI (74.3 mg, 0.387 mmol), followed by DIEA (99.8 mg, 0.774 mmol). Then to the reaction was added (S)-3-(5-(aminomethyl)-1-oxoisoindolin-2-yl)azepane-2,7-dione (TFA salt) (74 mg, 0.258 mmol). The solution was stirred at RT for 16 h. The reaction was diluted with water (10 mL), extracted with EA (20 mL×2). The combined organic layers were concentrated to give the crude product purified by silica gel chromatography eluting with DCM/MeOH from 0% to 6% to give Compound 11 (50 mg, 37.4%) as a white solid. MS (ESI) m/z 519.1 [M+H]$^+$. $^1$H NMR (400 MHz, DMSO-d$_6$) δ 10.73 (s, 1H), 8.62 (t, J=5.6 Hz, 1H), 7.64 (d, J=8.0 Hz, 1H), 7.39 (s, 1H), 7.35 (d, J=8.0 Hz, 1H), 7.14 (s, 1H), 7.09

(s, 2H), 5.23 (dd, J=4.8, 12.0 Hz, 1H), 4.46 (s, 2H), 4.37 (d, J=5.6 Hz, 2H), 3.53 (s, 4H), 3.43 (s, 2H), 3.08 (t, J=10.2 Hz, 1H), 2.58 (d, J=16.4 Hz, 1H), 2.33 (s, 14H), 2.29 (s, 3H), 2.25-2.23 (m, 1H), 2.13-2.00 (m, 2H), 1.83-1.81 (m, 1H).

(S)-1-(3-chloro-4-(trifluoromethyl)phenyl)-3-((2-(2,7-dioxoazepan-3-yl)-1-oxoisoindolin-5-yl)methyl) urea (Compound 12)

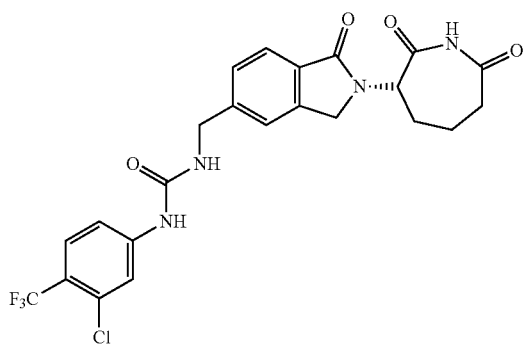

To a solution of triphosgene (609 mg, 2.14 mmol) in toluene (5 mL) was added dropwise a solution of 3-chloro-4-(trifluoromethyl)aniline (100 mg, 0.51 mmol) and refluxed at 80° C. for 0.5 h. Then the mixture was concentrated to give crude 2-chloro-4-isocyanato-1-(trifluoromethyl)benzene used in the next step without purification. To the solution of 2-chloro-4-isocyanato-1-(trifluoromethyl)benzene in THF was added (S)-3-(5-(aminomethyl)-1-oxoisoindolin-2-yl)azepane-2,7-dione (TFA salt) (59.1 mg, 0.21 mmol), followed by TEA (42 mg, 0.42 mmol). The mixture was stirred at RT for 2 h. The mixture was concentrated and purified by silica gel chromatography eluting with MeOH/DCM from 0% to 8% to give Compound 12 (29.4 mg, 28%) as a white solid. MS (ESI) m/z 509.0 [M+H]$^+$. $^1$H NMR (400 MHz, DMSO-d6) δ 10.72 (s, 1H), 9.36 (s, 1H), 7.91 (s, 1H), 7.70-7.68 (m, 2H), 7.54 (s, 1H), 7.45-7.41 (m, 2H), 7.06 (t, J=14 Hz, 1H), 5.23 (dd, J=7.6, 12.8 Hz, 1H), 4.52 (s, 2H), 4.43 (d, J=6.0 Hz, 2H), 3.12-3.04 (m, 1H), 2.61-2.55 (m, 1H), 2.28-2.22 (m, 1H), 2.12-1.96 (m, 2H), 1.84-1.76 (m, 1H).

(S)-2-(3-chloro-4-methoxyphenyl)-N-((2-(2,7-dioxoazepan-3-yl)-1-oxoisoindolin-5-yl)methyl)acetamide (Compound 13)

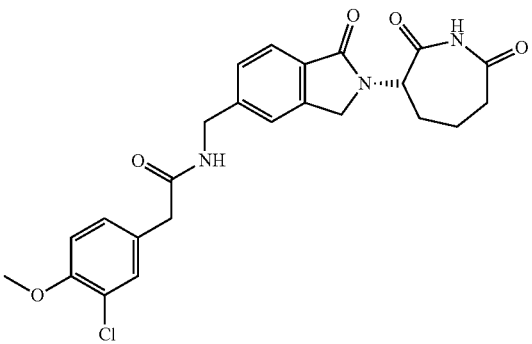

To a solution of 2-(4-methoxy-3-methylphenyl)acetic acid (25.8 mg, 0.13 mmol) in DMF (5 mL) was added HOBt (26.7 mg, 0.19 mmol) and EDCI (37.2 mg, 0.19 mmol), followed by DIEA (33.0 mg, 0.26 mmol). Then to the reaction was added (S)-3-(5-(aminomethyl)-1-oxoisoindolin-2-yl)azepane-2,7-dione (TFA salt) (37.0 mg, 0.13 mmol). The solution was stirred at RT for 16 h. The reaction was diluted with water (10 mL), extracted with EA (20 mL×2). The combined organic layers were concentrated to give the crude product, which was purified by silica gel chromatography eluting with MeOH/DCM from 0% to 10% to give Compound 13 (38.6 mg, 63.8%) as white solid. MS (ESI) m/z 470.1, 472.1 [M+H]$^+$. $^1$H NMR (400 MHz, DMSO-d6) δ 10.73 (s, 1H), 8.64 (t, J=6.0 Hz, 1H), 7.66 (d, J=8.0 Hz, 1H), 7.42 (s, 1H), 7.37-7.34 (m, 2H), 7.22-7.19 (m, 1H), 7.08 (d, J=8.4 Hz, 1H), 5.23 (dd, J=7.2, 12.0 Hz, 1H), 4.48 (s, 2H), 4.37 (d, J=5.6 Hz, 2H), 3.83 (s, 3H), 3.44 (s, 2H), 3.12-3.04 (m, 1H), 2.59-2.55 (m, 1H), 2.26-2.23 (m, 1H), 2.13-2.01 (m, 2H), 1.85-1.80 (m, 1H).

(S)—N-((2-(2,7-dioxoazepan-3-yl)-1-oxoisoindolin-5-yl)methyl)-2-(3-(morpholinomethyl)phenyl)acetamide (Compound 14)

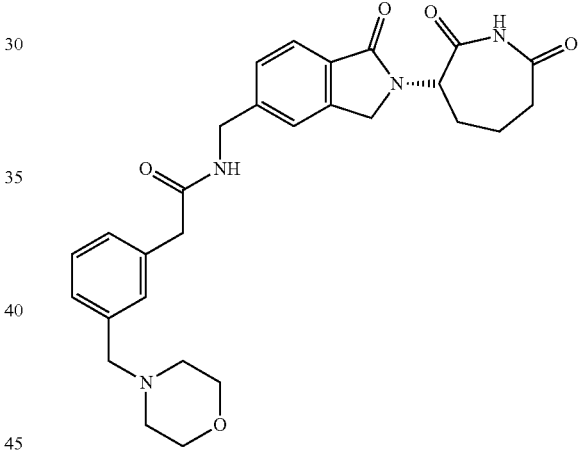

To a solution of methyl 3-methylbenzoate (4.0 g, 26.60 mmol) in CCl$_4$ (150 mL) was added NBS (5.69 g, 31.96 mmol), and the suspension was heated at 80° C. for 5 min and AIBN (2.18 g, 13.30 mmol) was added. The suspension continued to stir at 80° C. for 16 h. The mixture was cooled to RT and filtered. The filtrate was concentrated to give the crude product, which was purified by silica gel chromatography eluting with EA/petroleum ether from 0% to 3% to give methyl 3-(bromomethyl)benzoate (5.7 g, 94%) as a white oil.

To a solution of methyl 3-(bromomethyl)benzoate (7.0 g, 26.3 mmol) in ACN (100 mL) was added morpholine (3 g, 28.9 mmol), then DIEA (8.0 g, 52.6 mmol) was added. The reaction was stirred at RT for 1 h. The solvent was removed and the residue was purified by silica gel chromatography eluting with EA/petroleum ether from 10% to 18% to give methyl 3-(morpholinomethyl)benzoate (5.02 g, 82.5%) as a white oil.

To a solution of methyl 3-(morpholinomethyl)benzoate (5.02 g, 21.0 mmol) in MeOH (100 mL) was added sodium hydroxide (21.0 mL, 42.0 mmol, 2 M). The mixture was heated at 50° C. for 16 h. The solvent was removed, residue was adjusted to pH=3 with 1M HCl, and the suspension was filtered. The solid was dissolved in ACN (15 mL) and concentrated to give 3-(morpholinomethyl)benzoic acid (4.6 g, 100%) as a white solid used without further purification in the next step.

The solution of 3-(morpholinomethyl)benzoic acid (4.6 g, 22.7 mmol) in thionyl chloride (30 mL) was heated at 80° C. for 1 h. The solvent was removed and the residue was dried in vacuo to give 3-(morpholinomethyl)benzoyl chloride as a white solid used without further purification in the next step.

3-(Morpholinomethyl)benzoyl chloride was dissolved in THF (100 mL) and cooled to 0° C. trimethylsilyldiazomethane (22.7 mL, 45.4 mmol, 2M in hexane) was added, followed by TEA (3.4 g, 34.1 mmol). The mixture was stirred at RT for 18 h. The reaction was poured into NaHCO₃ (sat., 50 mL) and extracted with EA (50 mL×2). The combined organic layers were dried over sodium sulfate, filtered and concentrated to give the crude 2-diazo-1-(3-(morpholinomethyl)phenyl)ethanone (5.97 g, 100%) used directly for the next step without further purification.

To a mixture of EtOH/toluene (60 mL/24 mL) was added (benzoyloxy)silver (1.1 g, 4.9 mmol) and TEA (3.7 g, 36.6 mmol). The mixture was refluxed at 80° C. for 5 mins. The solution of 2-diazo-1-(3-(morpholinomethyl)phenyl)ethanone (3 g, 12.2 mmol) in EtOH (5 mL) was added and the solution was stirred at 80° C. for 2 h. The suspension was filtered and the filtrate was concentrated to give a yellow gum, which was purified by silica gel chromatography eluting with EA/petroleum ether from 5% to 18% to give ethyl 2-(3-(morpholinomethyl)phenyl)acetate (3 g, 54.5%) as a yellow oil.

To a solution of ethyl 2-(3-(morpholinomethyl)phenyl) acetate (159 mg, 0.605 mmol) in EtOH (10 mL) was added NaOH (0.6 mL, 1.2 mmol, 2 M). The mixture was heated at 50° C. for 2 h. The solvent was removed and the residue was adjusted to pH=3 with 1M HCl. The suspension was concentrated to give crude 2-(3-(morpholinomethyl)phenyl) acetic acid (142 mg) as a white solid.

To a solution of 2-(3-(morpholinomethyl)phenyl)acetic acid (41 mg, 0.176 mmol) in DMF (4 mL) at RT was added HOBt (36 mg, 0.264 mmol) and EDCI (50 mg, 0.264 mmol), followed by DIEA (45 mg, 0.351 mmol). Then to the reaction was added (S)-3-(5-(aminomethyl)-1-oxoisoindolin-2-yl)azepane-2,7-dione (TFA salt) (68 mg, 0.176 mmol). The solution was stirred at RT for 16 h. The reaction was diluted with water (10 mL), extracted with EA (10 mL×2). The combined organic layers were concentrated to give the crude product, which was purified by silica gel chromatography eluting with DCM/MeOH from 0% to 6% to give Compound 14 (27 mg, 30.6%) as a white solid. MS (ESI) m/z 505.3 [M+H]⁺. ¹H NMR (400 MHz, DMSO-d₆) δ 10.71 (s, 1H), 8.66 (t, J=6.0 Hz, 1H), 7.65 (d, J=7.6 Hz, 1H), 7.42 (s, 1H), 7.35 (d, J=8.0 Hz, 1H), 7.14 (s, 1H), 7.27-7.16 (m, 4H), 5.25-5.20 (m, 1H), 4.47 (s, 2H), 4.37 (d, J=5.6 Hz, 2H), 3.55 (s, 4H), 3.49 (s, 2H), 3.42 (s, 2H), 3.08 (t, J=10.2 Hz, 1H), 2.59-2.55 (m, 1H), 2.28-2.23 (m, 5H), 2.12-1.99 (m, 2H), 1.84-1.81 (m, 1H).

(S)-2-(4-chloro-3-(morpholinomethyl)phenyl)-N-((2-(2,7-dioxoazepan-3-yl)-1-oxoisoindolin-5-yl)methyl) acetamide (Compound 15)

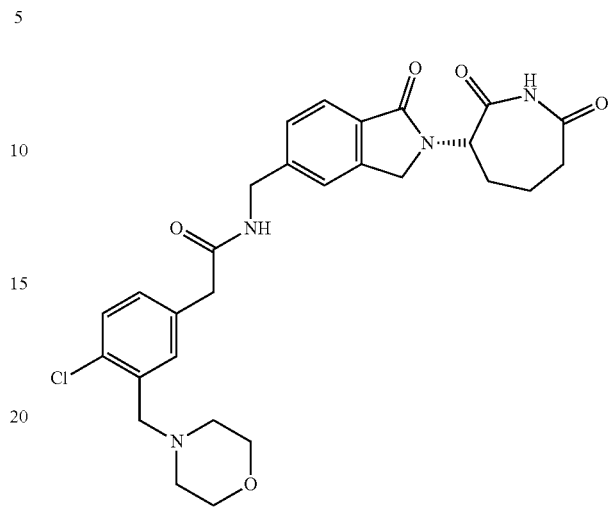

To a solution of methyl 4-chloro-3-methylbenzoate (4.0 g, 21.67 mmol) in CCl₄ (150 mL) was added NBS (4.6 g, 25.99 mmol) and the suspension was heated at 80° C. for 5 min and AIBN (1.78 g, 10.84 mmol) was added. The suspension was continued to stir at 80° C. for 16 h. The mixture was cooled to RT and filtered. The filtrate was concentrated to give the crude product, which was purified by silica gel chromatography eluting with EA/petroleum ether from 0% to 3% to give methyl 3-(bromomethyl)-4-chlorobenzoate (4.92 g, 86.6%) as a white oil.

To a solution of methyl 3-(bromomethyl)-4-chlorobenzoate (4.92 g, 18.78 mmol) in ACN (50 mL) was added morpholine (1.79 g, 20.66 mmol), then DIEA (4.85 g, 37.56 mmol) was added. The reaction was stirred at RT for 1 h. The solvent was removed and the residue was purified by silica gel chromatography eluting with EA/petroleum ether from 10% to 18% to give methyl 4-chloro-3-(morpholinomethyl) benzoate (3.39 g, 67%) as a white oil.

To a solution of methyl 4-chloro-3-(morpholinomethyl) benzoate (3.39 g, 12.6 mmol) in MeOH (40 mL) was added sodium hydroxide (12.6 mL, 25.2 mmol, 2 M). The mixture was heated at 50° C. for 3 h. The solvent was removed and the residue was adjusted to pH=3 with 1M HCl. The suspension was filtered and the filtrate dissolved in ACN (15 mL) and concentrated to give 4-chloro-3-(morpholinomethyl)benzoic acid (3.2 g, 100%) as a white solid.

The solution of 4-chloro-3-(morpholinomethyl)benzoic acid (3.2 g, 12.55 mmol) in thionyl chloride (40 mL) was heated at 80° C. for 3 h. The solvent was removed and the residue was dried in vacuo to give 4-chloro-3-(morpholinomethyl)benzoyl chloride as a white solid.

4-chloro-3-(morpholinomethyl)benzoyl chloride was dissolved in THF (40 mL) and cooled to 0° C. trimethylsilyldiazomethane (12.55 mL, 25.1 mmol, 2M in hexane) was added, followed by TEA (1.9 g, 18.83 mmol). The mixture was stirred at RT for 18 h. The reaction was poured into NaHCO₃ (sat., 50 mL) and extracted with EA (50 mL×2). The combined organic layers were dried over sodium sulfate, filtered and concentrated to give the crude 1-(4-chloro-3-(morpholinomethyl)phenyl)-2-diazoethanone (3.5 g, 100%). It was used directly for the next step without further purification.

To a mixture of EtOH/toluene (60 mL/24 mL) was added (benzoyloxy)silver (984 mg, 4.3 mmol) and TEA (3.57 g, 32.25 mmol). The mixture was refluxed at 80° C. for 5 mins. The solution of 1-(4-chloro-3-(morpholinomethyl)phenyl)-2-diazoethanone (3 g, 10.75 mmol) in EtOH (5 mL) was added at this temperature. The solution was stirred at 80° C. for 2 h. The suspension was filtered and the filtrate was concentrated to give a yellow gum, which was purified by silica gel chromatography eluting with EA/petroleum ether from 5% to 18% to give ethyl 2-(4-chloro-3-(morpholinomethyl)phenyl)acetate (1.9 g, 59%) as a yellow oil.

To a solution of ethyl 2-(4-chloro-3-(morpholinomethyl)phenyl)acetate (900 mg, 3.03 mmol) in EtOH (15 mL) was added sodium hydroxide (3.03 mL, 6.06 mmol, 2 M). The mixture was heated at 50° C. for 2 h. The solvent was removed and the residue was adjusted to pH=3 with 1M HCl. The suspension was concentrated to give crude 2-(4-chloro-3-(morpholinomethyl)phenyl)acetic acid (1.02 g) as a white solid.

To a solution of 2-(4-chloro-3-(morpholinomethyl)phenyl)acetic acid (48 mg, 0.176 mmol) in DMF (4 mL) at RT was added HOBt (37 mg, 0.27 mmol) and EDCI (52 mg, 0.27 mmol), followed by DIEA (46 mg, 0.36 mmol). Then to the reaction was added (S)-3-(5-(aminomethyl)-1-oxoisoindolin-2-yl)azepane-2,7-dione (TFA salt) (51 mg, 0.18 mmol). The solution was stirred at RT for 16 h. The reaction was diluted with water (10 mL), extracted with EA (10 mL×2). The combined organic layers were concentrated to give the crude product which was purified by silica gel chromatography eluting with DCM/MeOH from 0% to 6% to give Compound 15 (23.3 mg, 24%) as a white solid. MS (ESI) m/z 539.0 [M+H]$^+$. $^1$H NMR (400 MHz, DMSO-d$_6$) δ 10.70 (s, 1H), 8.73 (t, J=5.6 Hz, 1H), 7.67 (d, J=8.4 Hz, 1H), 7.60 (s, 1H), 7.54 (d, J=8.4 Hz, 1H), 7.45-7.36 (m, 3H), 5.25-5.21 (m, 1H), 4.48 (s, 2H), 4.41 (d, J=7.6 Hz, 2H), 3.55 (s, 4H), 3.25-3.20 (m, 4H), 3.08 (t, J=10.2 Hz, 1H), 2.59-2.55 (m, 1H), 2.28-2.23 (m, 5H), 2.12-1.99 (m, 2H), 1.84-1.81 (m, 1H).

(S)-1-(3-chloro-4-methylphenyl)-3-((2-(2,7-dioxoazepan-3-yl)-4-methyl-1-oxoisoindolin-5-yl)methyl)urea (Compound 16)

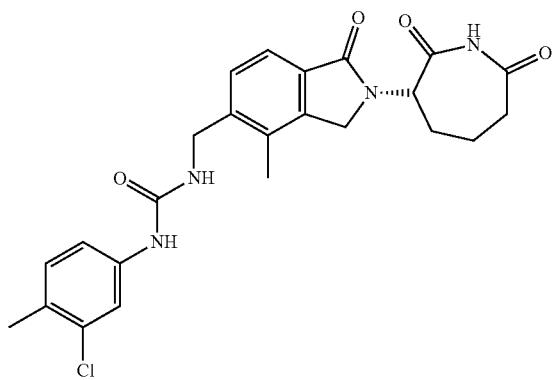

To a solution of methyl 4-bromo-2,3-dimethylbenzoate (3.0 g, 12.4 mmol) in carbon tetrachloride (100 mL) was added NBS (2.65 g, 14.9 mmol), the suspension was heated at 80° C. for 5 min, then AIBN (1.02 g, 6.2 mmol) was added. The suspension was stirred at 80° C. for 16 h, cooled to RT and filtered. The filtrate was concentrated to give the crude methyl 4-bromo-2-(bromomethyl)-3-methylbenzoate (3.9 g, 100%) as a yellow oil, which was used for next step directly without further purification.

To a solution of methyl 4-bromo-2-(bromomethyl)-3-methylbenzoate (3.9 g, 12.4 mmol) in DMF (50 mL) at RT was added (S)-3-aminoazepan-2-one (1.9 g, 14.9 mmol), followed by TEA (2.5 g, 24.8 mmol). The suspension was stirred at 50° C. for 1 h. Then the mixture was heated at 85° C. and stirred overnight. The solvent was removed and the residue was diluted with water (20 mL). The suspension was stirred at RT for 30 min. The white suspension was filtered and the filter cake was washed with water, dried in vacuo to give (S)-5-bromo-4-methyl-2-(2-oxoazepan-3-yl)isoindolin-1-one (1.51 g, 36%) as a light yellow solid.

To a solution of (S)-5-bromo-4-methyl-2-(2-oxoazepan-3-yl)isoindolin-1-one (300 mg, 0.89 mmol) in DMF (15 mL) was added Zn(CN)$_2$ (114 mg, 0.98 mmol) and [1,1'-bis(diphenylphosphino)ferrocene]dichloropalladium(II) [Pd(dppf)Cl$_2$] (84 mg, 0.09 mmol) and the mixture was heated in a microwave at 150° C. for 1 h. The mixture was concentrated and purified by silica gel chromatography to give (S)-4-methyl-1-oxo-2-(2-oxoazepan-3-yl)isoindoline-5-carbonitrile (1.26 g, 100%) as a yellow solid.

To a solution of (S)-4-methyl-1-oxo-2-(2-oxoazepan-3-yl)isoindoline-5-carbonitrile (300 mg, 1.06 mmol) in fluorobenzene/DMSO (18 mL/3 mL, 1 drop of water in DMSO) was added Dess-Martin reagent (1.12 g, 2.65 mmol). The suspension was heated at 80° C. for 18 h. The suspension was added to sat. sodium thiosulfate (20 mL). The suspension was stirred at 0° C. for 5 min then it was extracted with DCM (40 mL×2). The combined organic layers were washed with 10% sodium thiosulfate/sat. NaHCO$_3$ (1:1, 50 mL), brine, dried over sodium sulfate, filtered, concentrated and purified by silica gel chromatography to give (S)-2-(2,7-dioxoazepan-3-yl)-4-methyl-1-oxoisoindoline-5-carbonitrile (125 mg, 40%) as a white solid. MS (ESI) m/z 298.1 [M+H]$^+$. $^1$H NMR (400 MHz, DMSO-d$_6$) δ 10.76 (s, 1H), 7.93 (d, J=8.0 Hz, 1H), 7.72 (d, J=7.8 Hz, 1H), 5.31-5.26 (m, 1H), 4.60 (d, J=1.6 Hz, 2H), 3.13-3.06 (m, 1H), 2.61-2.50 (m, 1H), 2.35-2.31 (m, 1H), 2.15-2.02 (m, 2H), 1.86-1.83 (m, 1H).

To a solution of (S)-2-(2,7-dioxoazepan-3-yl)-4-methyl-1-oxoisoindoline-5-carbonitrile (550 mg, 1.85 mmol) in THF (10 mL) at RT was added Raney Ni (200 mg), followed by di-tert-butyl dicarbonate (Boc$_2$O) (484 g, 2.22 mmol) was added. The suspension was stirred at 25° C. under hydrogen for 14 h. The suspension was filtered and the filter cake was washed with EA (10 mL), the combined filtrate was concentrated to give the crude product, which was purified by silica gel chromatography to give (S)-tert-butyl ((2-(2,7-dioxoazepan-3-yl)-4-methyl-1-oxoisoindolin-5-yl)methyl)carbamate (140 mg, 18.8%) as a white solid.

To a solution of (S)-tert-butyl ((2-(2,7-dioxoazepan-3-yl)-4-methyl-1-oxoisoindolin-5-yl) methyl)carbamate (50 mg, 0.12 mmol) in DCM (3 mL) was added 2,2,2-trifluoroacetic acid (1 mL), the solution was stirred at RT for 1 h. The solvent was removed and the residue was diluted with water (2 mL) and extracted with DCM (3 mL). The aqueous layer was lyophilized to give (S)-3-(5-(aminomethyl)-4-methyl-1-oxoisoindolin-2-yl)azepane-2,7-dione (35 mg, TFA salt) as a white solid. MS (ESI) m/z 302.1 [M+H]$^+$. $^1$H NMR (400 MHz, DMSO-d$_6$) δ 10.72 (s, 1H), 8.37 (s, 3H), 7.63 (d, J=7.8 Hz, 1H), 7.54 (d, J=7.8 Hz, 1H), 5.26 (dd, J=5.2, 12.4 Hz, 1H), 4.52 (s, 2H), 4.18 (s, 2H), 3.14-3.05 (m, 1H), 2.61-2.57 (m, 1H), 2.35-2.30 (m, 4H), 2.15-2.02 (m, 2H), 1.84-1.82 (m, 1H).

To a solution of (S)-3-(5-(aminomethyl)-4-methyl-1-oxoisoindolin-2-yl)azepane-2,7-dione (TFA salt) (53 mg, 0.17 mmol) in tetrahydrofuran (5 mL) at RT was added 2-chloro-4-isocyanato-1-methylbenzene (32 mg, 0.193 mmol), followed by TEA (35 mg, 0.35 mmol) was added. The suspension was stirred at 25° C. for 1 h. The solvent was removed and the residue was purified by triturated with EA to give Compound 16 (27.7 mg, 33%) as a white solid. MS (ESI) m/z 469.1 [M+H]$^+$. $^1$H NMR (400 MHz, DMSO-d$_6$) δ 10.71 (d, J=3.6 Hz, 1H), 8.69 (d, J=5.2 Hz, 1H), 7.65 (d, J=8.4 Hz, 1H), 7.54 (s, 1H), 7.43-7.42 (m, 1H), 7.17-7.10 (m, 2H), 6.71 (s, 1H), 5.24 (m, 1H), 4.49-4.36 (m, 4H), 3.09-3.07 (m, 1H), 2.60-2.50 (m, 1H), 2.41-1.99 (m, 9H), 1.84-1.82 (m, 1H).

(S)-1-(3-chloro-4-methylphenyl)-3-((2-(2,7-dioxoazepan-3-yl)-1-oxoisoindolin-4-yl)methyl)urea
(Compound 17)

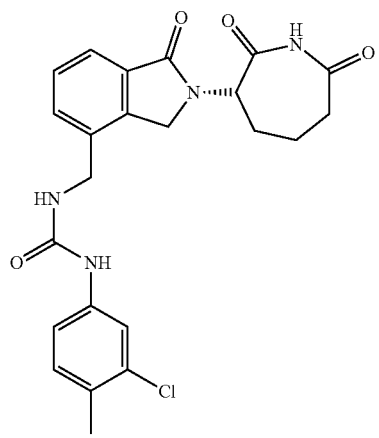

To a solution of (S)-3-(4-(aminomethyl)-1-oxoisoindolin-2-yl)azepane-2,7-dione (TFA salt) (51.6 mg, 0.18 mmol) in THF (5 mL) at 0° C. was added 2-chloro-4-isocyanato-1-methylbenzene (33.0 mg, 0.19 mmol) and TEA (39.1 mg, 0.39 mmol). The mixture was warmed to RT and stirred for 2 h. The mixture was concentrated and purified by silica gel chromatography eluting with MeOH/DCM from 0% to 6% to give Compound 17 (32.9 mg, 41.1%) as white solid. MS (ESI) m/z 454.8, 456.8 [M+H]$^+$. $^1$H NMR (400 MHz, DMSO-d$_6$) δ 10.70 (s, 1H), 8.77 (s, 1H), 7.64-7.60 (m, 2H), 7.56-7.48 (m, 2H), 7.17 (d, J=8.4 Hz, 1H), 7.12 (d, J=6.0 Hz, 1H), 6.82 (t, J=6.0 Hz, 1H), 5.26 (dd, J=7.2, 12.4 Hz, 1H), 4.59 (s, 2H), 4.38 (d, J=5.6 Hz, 1H), 3.13-3.05 (m, 1H), 2.62-2.52 (m, 1H), 2.33-2.24 (m, 1H), 2.23 (s, 3H), 2.17-2.01 (m, 2H), 1.86-1.79 (m, 1H).

(S)-1-(3-chloro-4-methylbenzyl)-3-((2-(2,7-dioxoazepan-3-yl)-1-oxoisoindolin-5-yl)methyl)urea
(Compound 18)

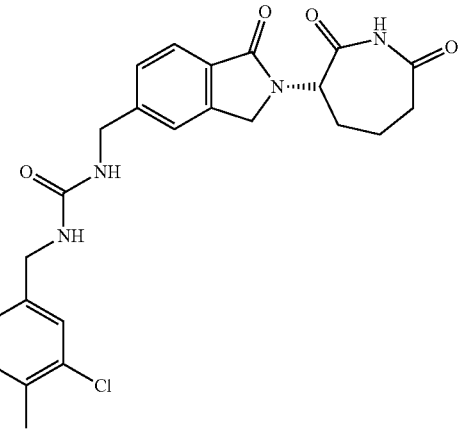

To a solution of (S)-3-(5-(aminomethyl)-1-oxoisoindolin-2-yl)azepane-2,7-dione (TFA salt) (68 mg, 0.176 mmol) in DMF (4 mL) was added CDI (29.0 mg, 0.18 mmol) and the suspension was stirred at RT for 14 h. Then (3-chloro-4-methylphenyl) methanamine (28.0 mg, 0.18 mmol) was added and the mixture was stirred at RT for 8 h. The suspension was diluted with water and extracted with DCM. The combined organic layers were dried over sodium sulfate, filtered and concentrated to give the crude product, which was purified by silica gel chromatography eluting with MeOH/DCM from 0% to 10% to give Compound 18 (21.0 mg, 25.1%) as a white solid. MS (ESI) m/z 469.1 [M+H]$^+$. $^1$H NMR (400 MHz, DMSO-d$_6$) δ 10.69 (s, 1H), 7.66 (d, J=8 Hz, 1H), 7.46 (s, 1H), 7.38 (d, J=8 Hz, 1H), 7.28 (d, J=7.2 Hz, 2H), 7.11 (d, J=8.8 Hz, 1H), 6.64-6.55 (m, 2H), 5.25-5.21 (m, 1H), 4.49 (s, 2H), 4.34 (d, J=6 Hz, 2H), 4.19 (d, J=6 Hz, 2H), 3.12-3.04 (m, 1H), 2.57 (d, J=16.8 Hz, 1H), 2.28-2.23 (m, 1H), 2.29 (s, 3H), 2.12-1.99 (m, 2H), 1.84-1.81 (m, 1H).

(S)-1-(3-chloro-4-methylphenethyl)-3-((2-(2,7-dioxoazepan-3-v)-1-oxoisoindolin-5-yl)methyl)urea
(Compound 19)

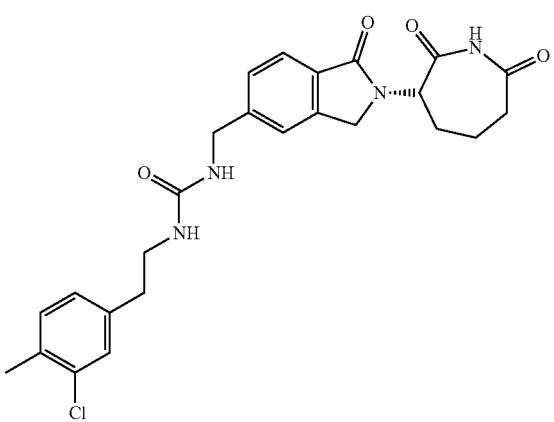

To a solution of (S)-3-(5-(aminomethyl)-1-oxoisoindolin-2-yl)azepane-2,7-dione (TFA salt) (68 mg, 0.176 mmol) in DMF (4 mL) was added CDI (29.0 mg, 0.18 mmol) and the suspension was stirred at RT for 14 h. Then 2-(3-chloro-4-methylphenyl)ethanamine (30.4 mg, 0.18 mmol) was added and the mixture was stirred at RT for 8 h. The suspension was diluted with water and extracted with DCM. The combined organic layers were dried over sodium sulfate, filtered and concentrated to give the crude product, which was purified by silica gel chromatography eluting with MeOH/DCM from 0% to 10% to give Compound 19 (33.5 mg, 34.1%) as a white solid. MS (ESI) m/z 483.1 [M+H]$^+$. $^1$H NMR (400 MHz, DMSO-d$_6$) δ 10.70 (s, 1H), 7.66 (d, J=7.6 Hz, 1H), 7.45 (s, 1H), 7.35 (d, J=7.6 Hz, 1H), 7.26-7.24 (m, 2H), 7.07 (d, J=8 Hz, 1H), 6.49 (t, J=5.6 Hz, 1H), 6.01 (t, J=8.4 Hz, 1H), 5.25-5.21 (m, 1H), 4.50 (s, 2H), 4.30 (s, 2H), 3.24 (q, J=6.4 Hz, 2H), 3.08 (t, J=13.6 Hz 1H), 2.67 (t, J=7.2 Hz, 2H), 2.59-2.55 (m, 1H), 2.36-2.22 (m, 4H), 2.12-1.99 (m, 2H), 1.84-1.78 (m, 1H).

(S)-1-(3-chloro-4-methylbenzyl)-3-((2-(2,7-dioxoazepan-3-yl)-1-oxoisoindolin-4-yl)methyl)urea (Compound 20)

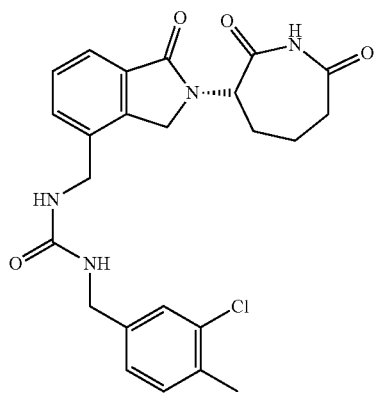

To a solution of (S)-3-(4-(aminomethyl)-1-oxoisoindolin-2-yl)azepane-2,7-dione (TFA salt) (59.3 mg, 0.21 mmol) in DMF (4 mL) was added CDI (34.1 mg, 0.21 mmol) and the suspension was stirred at RT for 14 h. Then (3-chloro-4-methylphenyl)methanamine (32.7 mg, 0.21 mmol) was added and the mixture was stirred at RT for 8 h. The suspension was diluted with water and extracted with DCM. The combined organic layers were dried over sodium sulfate, filtered and concentrated to give the crude product, which was purified by silica gel chromatography eluting with MeOH/DCM from 0% to 10% to give Compound 20 (26.5 mg, 31.5%) as a white solid. MS (ESI) m/z 469.1, 471.1 [M+H]$^+$. $^1$H NMR (400 MHz, DMSO-d$_6$) δ 10.73 (s, 1H), 7.62-7.59 (m, 1H), 7.50-7.47 (m, 2H), 7.27 (d, J=7.2 Hz, 2H), 7.11 (d, J=8.0 Hz, 1H), 6.63-6.56 (m, 2H), 5.25 (dd, J=7.2, 12.0 Hz, 1H), 4.55 (s, 2H), 4.33 (d, J=6.0 Hz, 2H), 4.19 (d, J=6.0 Hz, 2H), 3.13-3.06 (m, 1H), 2.60-2.56 (m, 1H), 2.32-2.19 (m, 4H), 2.11-1.96 (m, 2H), 1.84-1.76 (m, 1H).

(S)-1-(3-chloro-4-methylphenyl)-3-((2-(2,7-dioxoazepan-3-yl)-1-oxoisoindolin-5-yl)methyl)-1-methylurea (Compound 21)

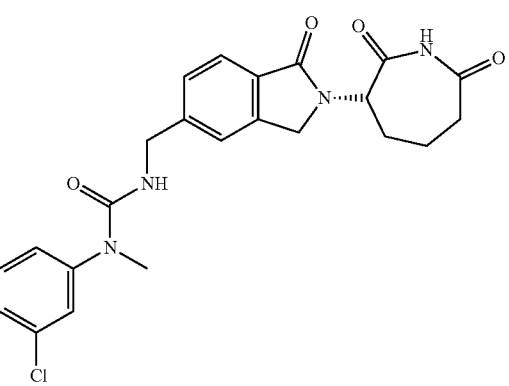

To a solution of (S)-3-(5-(aminomethyl)-1-oxoisoindolin-2-yl)azepane-2,7-dione (TFA salt) (74.2 mg, 0.26 mmol) in DMF (4 mL) was added CDI (42.1 mg, 0.26 mmol) and the suspension was stirred at RT for 14 h. Then 3-chloro-N,4-dimethylaniline (37.3 mg, 0.26 mmol) was added and the mixture stirred at RT for 8 h. The suspension was diluted with water and extracted with DCM. The combined organic layers were washed with water, dried over sodium sulfate, filtered and concentrated to give the crude product, which was purified by silica gel chromatography eluting with MeOH/DCM from 0% to 10% to give Compound 21 (23.2 mg, 19.1%) as a white solid. MS (ESI) m/z 469.1, 471.1 [M+H]$^+$. $^1$H NMR (400 MHz, DMSO-d$_6$) δ 10.70 (s, 1H), 7.65 (d, J=8.0 Hz, 1H), 7.48 (s, 1H), 7.39-7.34 (m, 3H), 7.17 (d, J=8.4 Hz, 1H), 6.87 (t, J=6.0 Hz, 1H), 5.23 (dd, J=6.8, 12.0 Hz, 1H), 4.51 (s, 2H), 4.31 (d, J=6.0 Hz, 2H), 3.08 (s, 3H), 3.12-3.04 (m, 1H), 2.61-2.55 (m, 1H), 2.31 (s, 3H), 2.28-2.22 (m, 1H), 2.12-1.97 (m, 2H), 1.85-1.80 (m, 1H).

(S)-1-(3-chloro-4-methylphenyl)-3-((2-(2,7-dioxoazepan-3-yl)-6-fluoro-1-oxoisoindolin-5-yl)methyl)urea (Compound 22)

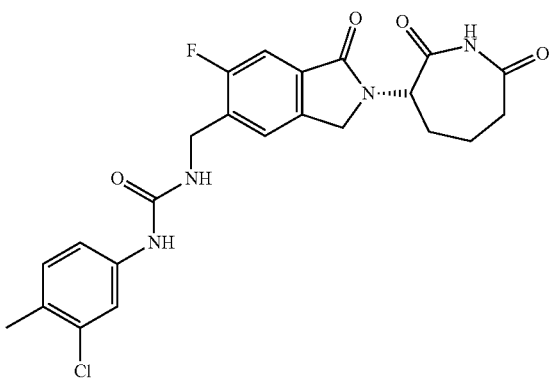

To a solution of 4-bromo-2-fluoro-5-methylbenzonitrile (10.0 g, 46.7 mmol) in N,N-dimethylacetamide (30 mL) was added Pd(dppf)Cl$_2$ (5.1 g, 7.0 mmol) and MeOH (10 mL), followed by TEA (14.3 g, 140.1 mmol). The mixture was heated at 90° C. overnight under carbon monoxide (5 MPa).

The mixture was cooled to RT and the mixture was diluted with water, extracted with EA. The combined organic layers were concentrated to give the crude product, which was purified by silica gel chromatography eluting with EA/petroleum ether from 5% to 10% to give methyl 4-cyano-5-fluoro-2-methylbenzoate (7.33 g, 81%) as a white solid.

To a solution of methyl 4-cyano-5-fluoro-2-methylbenzoate (4.0 g, 20.80 mmol) in carbon tetrachloride (150 mL) was added NBS (3.9 g, 21.84 mmol), the suspension was heated at 80° C. for 5 min, then AIBN (1.7 g, 10.40 mmol) was added. The suspension continued to stir at 80° C. for 16 h. The mixture was cooled to RT and filtered. The filtrate was concentrated to give the crude product, which was purified by silica gel chromatography eluting with EA/petroleum ether from 0% to 3% to give methyl 2-(bromomethyl)-4-cyano-5-fluorobenzoate (3.41 g, 60%) as a yellow solid.

To a solution of methyl 2-(bromomethyl)-4-cyano-5-fluorobenzoate (1.19 g, 4.375 mmol) in DMF (40 mL) was added (S)-3-aminoazepan-2-one (0.67 g, 5.25 mmol), followed by TEA (0.884 g, 8.75 mmol). The suspension was heated at 50° C. for 1 h, and then stirred at 85° C. overnight. The mixture was concentrated and the residue diluted with water at 0° C. Then the mixture was filtered and the solid recrystallized to give (S)-6-fluoro-1-oxo-2-(2-oxoazepan-3-yl)isoindoline-5-carbonitrile (0.69 g, 54.8%) as a light yellow solid. MS (ESI) m/z 288.0 [M+H]⁺.

To a solution of (S)-6-fluoro-1-oxo-2-(2-oxoazepan-3-yl) isoindoline-5-carbonitrile (584 mg, 2.03 mmol) in fluorobenzene/DMSO (18 mL/3 mL, 1 drop of water in DMSO) was added Dess-Martin reagent (2.58 g, 6.09 mmol). The mixture was stirred at 80° C. overnight, filtered and quenched with sat. sodium thiosulfate (10 mL). After stirring 10 minutes, it was extracted with DCM. The combined organic layers were washed with sat. NaHCO₃, dried over sodium sulfate, filtered and concentrated to give the crude product, which was purified by silica gel chromatography to give (S)-2-(2,7-dioxoazepan-3-yl)-6-fluoro-1-oxoisoindoline-5-carbonitrile (250 mg, 41%) as a white solid. MS (ESI) m/z 300.8 [M+H]⁺.

To a solution of (S)-2-(2,7-dioxoazepan-3-yl)-6-fluoro-1-oxoisoindoline-5-carbonitrile (222 mg, 0.738 mmol) in THF (5 mL) was added Raney Ni (22 mg) and Boc₂O (322 mg, 1.476 mmol). The suspension was stirred at RT under hydrogen overnight then filtered, concentrated and purified by silica gel chromatography to give (S)-tert-butyl ((2-(2,7-dioxoazepan-3-yl)-6-fluoro-1-oxoisoindolin-5-yl)methyl) carbamate (180 mg, 60%) as a white solid. MS (ESI) m/z 406.2 [M+H]⁺.

To a solution of (S)-tert-butyl ((2-(2,7-dioxoazepan-3-yl)-6-fluoro-1-oxoisoindolin-5-yl)methyl)carbamate (90 mg, 0.222 mmol) in DCM (6 mL) at 0° C. was added TFA (1.5 mL). The suspension was stirred at RT for 1 h. The solvent was removed to give the crude product (67.8 mg, 100%) as a yellow oil, which was dissolved in THF (10 mL) at RT, followed by TEA (56 mg, 0.555 mmol) and 2-chloro-4-isocyanato-1-methylbenzene (44.6 mg, 0.266 mmol). The mixture was stirred at RT for 1 h. The solvent was removed to give the crude product, which was purified by prep-HPLC to give Compound 22 (67.2 mg, 64%) as a white solid. MS (ESI) m/z 473.0 [M+H]⁺. ¹H NMR (DMSO-d₆, 400 MHz) δ: 10.71 (s, 1H), 8.77 (s, 1H), 7.66 (d, J=2.4 Hz, 1H), 7.60 (d, J=6.4 Hz, 1H), 7.50 (d, J=9.4 Hz, 1H), 7.18 (d, J=8.4 Hz, 1H), 7.14-7.10 (m, 1H), 6.80-6.77 (m, 1H), 5.23 (dd, J=12.8, 4.2 Hz, 1H), 4.50 (s, 2H), 4.43 (d, J=6.0 Hz, 2H), 3.08 (t, J=15.6 Hz, 1H), 2.59-2.49 (m, 1H), 2.23 (s, 4H), 2.15-1.97 (m, 2H), 1.90-1.77 (m, 1H).

(S)-1-(3-chloro-4-methylphenyl)-3-(2-(2-(2,7-dioxoazepan-3-yl)-1-oxoisoindolin-4-yl)ethyl)urea
(Compound 23)

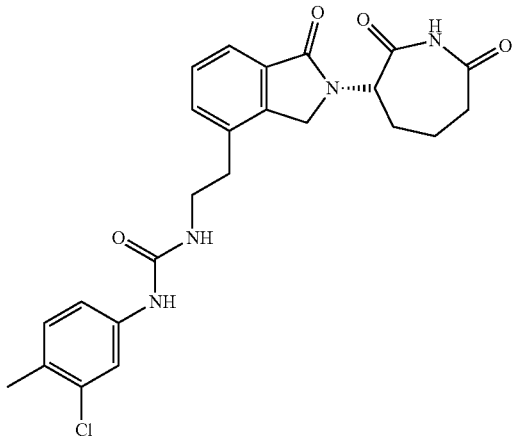

To a solution of methyl 3-iodo-2-methylbenzoate (10.0 g, 36.2 mmol) in carbon tetrachloride (200 mL) was added NBS (8.4 g, 47.1 mmol) and benzoyl peroxide (4.4 g, 18.1 mmol), the suspension was heated at 90° C. overnight. The mixture was then cooled to RT and filtered. The filtrate was concentrated to give the crude product, which was purified by silica-gel column (light petro 100%) to give methyl 2-(bromomethyl)-3-iodobenzoate (9.8 g, 76%) as a yellow solid.

To a solution of methyl 2-(bromomethyl)-3-iodobenzoate (6.3 g, 17.8 mmol) in DMF (60 mL) was added (S)-3-aminoazepan-2-one (4.0 g, 31.6 mmol), followed by TEA (5.4 g, 53.4 mmol). The mixture was stirred at 50° C. overnight. The mixture was then filtered to afford crude product, which was washed with EA and dried under vacuum to give (S)-4-iodo-2-(2-oxoazepan-3-yl)isoindolin-1-one (5.6 g, 85%) as a white solid.

To a solution of (S)-4-iodo-2-(2-oxoazepan-3-yl)isoindolin-1-one (3.7 g, 10.0 mmol) and benzyl acrylate (2.1 g, 13.0 mmol) in DMF (50 mL) was added tri-o-tolylphosphine (POT) (2.0 g, 6.5 mmol), TEA (3.0 g, 30.0 mmol) and palladium(II) acetate (740 mg, 3.2 mmol). The reaction was stirred at 100° C. overnight. The mixture was then diluted with water (100 mL) and extracted by EA (100 mL). The combined organic phase was washed with brine, dried over anhydrous magnesium sulfate, evaporated and purified by silica gel chromatography (EA 100%) to give (S, E)-benzyl 3-(1-oxo-2-(2-oxoazepan-3-yl)isoindolin-4-yl)acrylate (2.2 g, 54%) as a yellow solid. MS (ESI) m/z 405.3 [M+H]⁺.

To a solution of (S, E)-benzyl 3-(1-oxo-2-(2-oxoazepan-3-yl)isoindolin-4-yl)acrylate (2.1 g, 5.2 mmol) in fluorobenzene/DMSO (18 mL/3 mL, 1 drop of water in DMSO) was added Dess-Martin reagent (8.8 g, 20.8 mmol). The suspension was heated at 80° C. for 18 h. The suspension was added to sat. sodium thiosulfate (20 mL). The suspension was stirred at 0° C. for 5 min then it was extracted with DCM (40 mL×2). The combined organic layers were washed with 10% sodium thiosulfate/sat. NaHCO₃ (1:1, 50 mL), brine, dried over sodium sulfate, filtered, concentrated and triturated with EA (20 mL) to get (S, E)-benzyl 3-(2-(2,7-dioxoazepan-3-yl)-1-oxoisoindolin-4-yl)acrylate (1.3 g, 58%) as a yellow solid. MS (ESI) m/z 419.4 [M+H]⁺.

To a solution of (S, E)-benzyl 3-(2-(2,7-dioxoazepan-3-yl)-1-oxoisoindolin-4-yl)acrylate (600 mg, 1.4 mmol) in THF (40 mL), was added palladium on activated carbon (5% Pd, 600 mg), the solution was stirred at RT overnight under 1 atm hydrogen. The mixture was filtered through a celite pad, and the filtrate was concentrated to give (S)-3-(2-(2,7-dioxoazepan-3-yl)-1-oxoisoindolin-4-yl)propanoic acid (403 mg, 87%) as a white solid. MS (ESI) m/z 331.2 [M+H]$^+$.

To a solution of (S)-3-(2-(2,7-dioxoazepan-3-yl)-1-oxoisoindolin-4-yl)propanoic acid (200 mg, 0.6 mmol) in THF (15 mL) was added TEA (152 mg, 1.5 mmol) and followed by diphenylphosphoryl azide (250 mg, 0.9 mmol). The mixture was stirred at RT for 4 h. 3-Chloro-4-methylaniline (127 mg, 0.9 mmol) was added into the above mixture, and the mixture was heated to 80° C. overnight under nitrogen atmosphere. The result mixture was diluted with sat. NaHCO$_3$, extracted with EA (15 mL×3). The combined organic phase was washed with brine, dried over magnesium sulfate, concentrated to give a crude, which was triturated with a solution of DCM/MeOH (1:1) to afford Compound 23 (61 mg, 27%) as a white solid. MS (ESI) m/z 468.8 [M+H]$^+$. $^1$H NMR (400 MHz, DMSO-d$_6$) δ 10.70 (s, 1H), 8.57 (s, 1H), 7.65-7.60 (m, 1H), 7.60-7.58 (m, 1H), 7.51-7.46 (m, 2H), 7.16 (d, J=8.4 Hz, 1H), 7.08-7.06 (m, 1H), 6.22 (t, J=5.6 Hz, 1H), 5.24 (dd, J=4.8 Hz, J=5.2 Hz, 1H), 4.53 (s, 2H), 3.43-3.31 (m, 2H), 3.06 (t, J=14.0 Hz, 1H), 286-2.83 (m, 2H), 2.54 (m, 1H), 2.25-2.22 (m, 4H), 2.08-1.97 (m, 2H), 1.77-1.76 (m, 1H).

(S)-1-(3-chloro-4-methylphenyl)-3-(2-(2-(2,7-dioxoazepan-3-yl)-1-oxoisoindolin-5-yl)ethyl)urea (Compound 24)

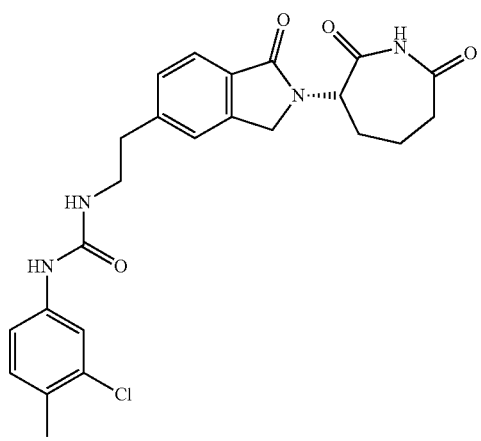

To a solution of methyl 4-bromo-2-methylbenzoate (5.0 g, 21.83 mmol) in carbon tetrachloride (100 mL) was added NBS (4.3 g, 24.01 mmol), the suspension was heated at 80° C. for 5 min, then AIBN (1.07 g, 6.55 mmol) was added. The suspension continued to stir at 80° C. for 16 h, then cooled to RT and filtered. The filtrate was concentrated to give the crude product, which was purified by silica-gel column to give methyl 4-bromo-2-methylbenzoate (4.6 g, 68%) as a white solid.

To a solution of methyl 4-bromo-2-methylbenzoate (4.6 g, 14.88 mmol) in DMF (50 mL) was added (S)-3-aminoazepan-2-one (1.9 g, 14.88 mmol), and then TEA (3.0 g, 29.76 mmol) was added. The reaction was stirred at 100° C. for 7 h. The solvent was then removed and the residue was purified by silica-gel column to give (S)-5-bromo-2-(2-oxoazepan-3-yl)isoindolin-1-one (3.0 g, 62%) as a white solid. MS (ESI) m/z 324.1 [M+H]$^+$.

To a solution of (S)-5-bromo-2-(2-oxoazepan-3-yl)isoindolin-1-one (1.4 g, 4.33 mmol) and benzyl acrylate (0.9 g, 5.56 mmol) in ACN (20 mL) was added tri-o-tolylphosphine (POT) (760 mg, 2.50 mmol), TEA (2.8 mL, 20.10 mmol) and palladium(II) acetate (140 mg, 0.62 mmol). The mixture was stirred at 95° C. overnight, diluted with water (20 mL) and EA (20 mL). The organic phase was separated and washed with brine, dried over anhydrous sodium sulfate, evaporated and purified by silica gel chromatography (EA 100%) to give (S, E)-benzyl 3-(1-oxo-2-(2-oxoazepan-3-yl)isoindolin-5-yl)acrylate (1.1 g, 63%) as a yellow solid. MS (ESI) m/z 405.3 [M+H]$^+$.

(S, E)-Benzyl 3-(1-oxo-2-(2-oxoazepan-3-yl)isoindolin-5-yl)acrylate (466 mg, 1.15 mmol) was slurried in fluorobenzene (30 mL) with 5 mL DMSO and 1 drop of water. The Dess-Martin reagent (1.96 g, 4.61 mmol) was added and the mixture was stirred at 90° C. overnight. The reaction was cooled to RT and sat. sodium thiosulfate solution (15 mL) was added followed by stirring for 5 min. The organic phase was washed with 10% aq. sodium thiosulfate/sat. NaHCO$_3$ (1:1 mixture) (20 mL) and brine. The organic layer was concentrated to afford the crude product, which was triturated with EA (4 mL) to get (S, E)-benzyl 3-(2-(2,7-dioxoazepan-3-yl)-1-oxoisoindolin-5-yl)acrylate (303 mg, 63%) as a white solid. MS (ESI) m/z 419.2 [M+H]$^+$.

To a solution of (S, E)-benzyl 3-(2-(2,7-dioxoazepan-3-yl)-1-oxoisoindolin-5-yl)acrylate (228 mg, 0.54 mmol) in THF (20 mL) and formic acid (3.5 mL) was added palladium on activated carbon (5% Pd, 400 mg) and the solution was stirred at 30° C. overnight under 1 atm hydrogen. The mixture was filtered through a celite pad, and the filtrate was concentrated to give (S)-3-(2-(2,7-dioxoazepan-3-yl)-1-oxoisoindolin-5-yl)propanoic acid (151 mg, 84%) as a white solid. MS (ESI) m/z 331.1 [M+H]$^+$.

To a solution of (S)-3-(2-(2,7-dioxoazepan-3-yl)-1-oxoisoindolin-5-yl)propanoic acid (151 mg, 0.46 mmol) in THF (5 mL) was added TEA (116 mg, 1.15 mmol) and diphenylphosphoryl azide (190 mg, 0.69 mmol). The mixture was stirred at RT for 4 h. 3-chloro-4-methylaniline (97 mg, 0.69 mmol) was added and the reaction was heated to 89° C. overnight under nitrogen. The mixture was diluted with sat. NaHCO$_3$, extracted with EA (10 mL×3). The organic phase was washed with brine, dried over magnesium sulfate, concentrated to give a crude, which was purified by prep-TLC (petroleum ether:EA=1:3) to afford Compound 24 (12.5 mg, 5.8%) as a yellow solid. MS (ESI) m/z 469.1 [M+H]$^+$. $^1$H NMR (400 MHz, DMSO-d$_6$) δ 10.73 (br, 1H), 8.59 (s, 1H), 7.68-7.65 (m, 2H), 7.50 (s, 1H), 7.39 (d, J=8.0 Hz, 1H), 7.17 (d, J=8.4 Hz, 1H), 7.09 (d, J=8.0 Hz, 1H), 6.20-6.17 (m, 1H), 5.25-5.22 (m, 1H), 4.51 (s, 2H), 3.37-3.31 (m, 2H), 3.09 (t, J=14.0 Hz, 1H), 2.90-2.86 (m, 2H), 2.51 (m, 1H), 2.23 (m, 1H), 2.13 (s, 3H), 2.08-2.01 (m, 2H), 1.86-1.85 (m, 1H).

(S)—N-((2-(2,7-dioxoazepan-3-yl)-1-oxoisoindolin-5-yl)methyl)-2,2-difluoro-2-(4-fluorophenyl)acetamide (Compound 25)

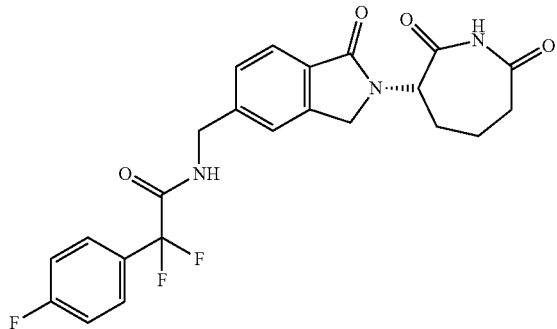

To a solution of 2,2-difluoro-2-(4-fluorophenyl)acetic acid (65.0 mg, 0.34 mmol) in DMF (5 mL) was added HOBt (58.8 mg, 0.43 mmol) and EDCI (81.8 mg, 0.43 mmol), followed by DIEA (72.2 mg, 0.56 mmol). Then to the reaction was added (S)-3-(5-(aminomethyl)-1-oxoisoindolin-2-yl)azepane-2,7-dione (TFA salt) (80.4 mg, 0.28 mmol). The solution was stirred at RT for 16 h. The reaction was diluted with water (10 mL), extracted with EA (20 mL×2). The combined organic layers were concentrated to give the crude product, which was purified by prep-HPLC to give Compound 25 (25.3 mg, 19.5%) as white solid. MS (ESI) m/z 460.1 [M+H]$^+$. $^1$H NMR (400 MHz, DMSO-d6) δ 10.72 (s, 1H), 9.69 (t, J=5.6 Hz, 1H), 7.68-7.64 (m, 3H), 7.42-7.34 (m, 4H), 5.23 (dd, J=7.2, 12.0 Hz, 1H), 4.49 (s, 2H), 4.46 (d, J=5.6 Hz, 2H), 3.12-3.05 (m, 1H), 2.60-2.51 (m, 1H), 2.31-2.27 (m, 1H), 2.22-2.00 (m, 2H), 1.87-1.80 (m, 1H).

(S)-1-(3-chloro-4-methylphenyl)-3-((2-(2,7-dioxoazepan-3-yl)-1-oxoisoindolin-5-yl)methyl)thiourea (Compound 26)

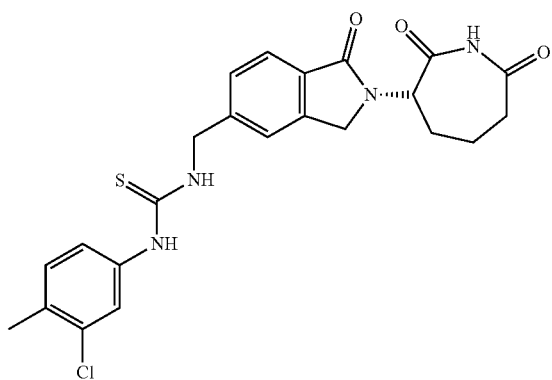

To a solution of (S)-3-(5-(aminomethyl)-1-oxoisoindolin-2-yl)azepane-2,7-dione (TFA salt) (59.3 mg, 0.21 mmol) in THF (3 mL) at 0° C. was added 2-chloro-4-isothiocyanato-1-methylbenzene (45.6 mg, 0.25 mmol) and TEA (42.4 mg, 0.42 mmol). The mixture was warmed to RT and stirred for 2 h. It was concentrated and purified by prep-HPLC to give Compound 26 (36.4 mg, 37.5%) as white solid. MS (ESI) m/z 470.8, 472.8 [M+H]$^+$. $^1$H NMR (400 MHz, DMSO-d$_6$) δ 10.73 (s, 1H), 9.75 (t, J=5.2 Hz, 1H), 8.38 (s, 1H), 7.69 (d, J=7.2 Hz, 1H), 7.61 (s, 1H), 7.55 (s, 1H), 7.45 (d, J=3.6 Hz, 1H), 7.30 (d, J=8.0 Hz, 1H), 7.24-7.22 (m, 1H), 5.23 (dd, J=7.2, 12.4 Hz, 1H), 4.85 (d, J=5.2 Hz, 2H), 4.52 (s, 2H), 3.13-3.05 (m, 1H), 2.59-2.54 (m, 1H), 2.32-2.22 (m, 4H), 2.14-1.97 (m, 2H), 1.87-1.76 (m, 1H).

(S)-1-(3-chloro-4-methylphenyl)-3-((2-(2,7-dioxoazepan-3-yl)-1,3-dioxoisoindolin-5-yl)methyl)urea (Compound 27)

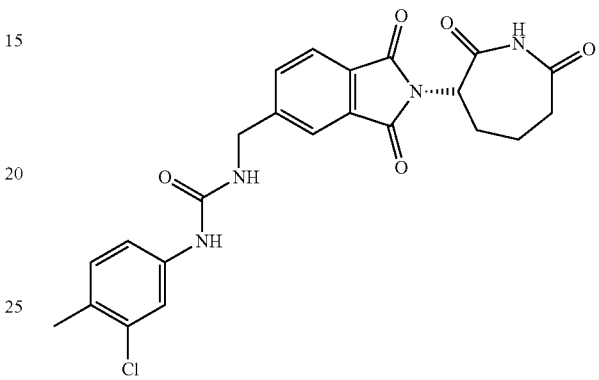

To a solution of methyl 5-bromoisobenzofuran-1,3-dione (3.5 g, 15.4 mmol) in THF (50 mL) was added (S)-3-aminoazepan-2-one (1.97 g, 15.4 mmol), the suspension was stirred at RT for 3 h. The mixture was then concentrated to give 4-bromo-2-((2-oxoazepan-3-yl)carbamoyl)benzoic acid (5.0 g, crude), which was used directly for the next step without purification.

To a solution of 4-bromo-2-((2-oxoazepan-3-yl)carbamoyl)benzoic acid (5.0 g, 14.84 mmol) in DMF (50 mL) was added HOBt (3.0 g, 22.3 mmol) and EDCI (4.28 g, 22.3 mmol) followed by DIEA (5.75 g, 44.6 mmol). The suspension was stirred at RT for 5 h. The mixture was concentrated and purified by silica gel chromatography eluting with petroleum ether/EA from 50% to 100% to give (S)-5-bromo-2-(2-oxoazepan-3-yl)isoindoline-1,3-dione (3.2 g, 69%) as a white solid. MS (ESI) m/z 336.9 [M+H]$^+$.

To a solution of (S)-5-bromo-2-(2-oxoazepan-3-yl)isoindoline-1,3-dione (3.2 g, 9.5 mmol) in DMF was added tris(dibenzylideneacetone)dipalladium(0) [Pd$_2$(dba)$_3$] (902 mg, 0.95 mmol), 1,1'-bisdiphenylphosphinoferrocene [dppf] (1.02 g, 1.9 mmol) and zinc cyanide (1.23 g, 10.45 mmol). The mixture was heated to 150° C. for 1 h in a microwave under nitrogen. The mixture was concentrated and purified by silica gel chromatography eluting with petroleum ether/EA from 50% to 100% to give (S)-1,3-dioxo-2-(2-oxoazepan-3-yl)isoindoline-5-carbonitrile (1.5 g, 56%) a yellow solid. MS (ESI) m/z 284.0 [M+H]$^+$.

To a solution of (S)-1,3-dioxo-2-(2-oxoazepan-3-yl)isoindoline-5-carbonitrile (1.2 g, 4.24 mmol) in ACN/DMSO (15 mL/2.5 mL, 2 drops of water in DMSO) was added Dess-Martin periodinane (4.47 g, 10.6 mmol). The suspension was heated at 80° C. for 4 h. The mixture was cooled down to RT and 50 mL of a sat. sodium thiosulfate solution was added followed by stirring for 5 min. The mixture was extracted with DCM (50 mL×2) and the combined solution was washed with 10% aq. sodium thiosulfate/sat. NaHCO$_3$ (1:1 mixture) (50 mL) and brine (50 mL). The organic layer was dried over sodium sulfate, filtered and concentrated to afford the crude product, which was purified by silica gel chromatography eluting with petroleum ether/EA from 50% to 100% to give (S)-2-(2,7-dioxoazepan-3-yl)-1,3-dioxoisoindoline-5-carbonitrile (1.0 g, 68%) as a white solid.

To a solution of (S)-2-(2,7-dioxoazepan-3-yl)-1,3-dioxoisoindoline-5-carbonitrile (500 mg, 1.68 mmol) in THF (20 mL) was added Raney Ni (200 mg), followed by (Boc)$_2$O (734 mg, 3.36 mmol). The suspension was stirred at RT under hydrogen for 16 h. The suspension was filtered and the filter cake was washed with DCM (10 mL). The combined filtrate was concentrated to give the crude product, which was purified by silica gel chromatography eluting with petroleum ether/EA from 50% to 100% to give (S)-tert-butyl ((2-(2,7-dioxoazepan-3-yl)-1,3-dioxoisoindolin-5-yl)methyl)carbamate (380 mg, 56%) as a white solid. MS (ESI) m/z 419.1 [M+18]$^+$.

To a solution of (S)-tert-butyl ((2-(2,7-dioxoazepan-3-yl)-1,3-dioxoisoindolin-5-yl)methyl)carbamate (120 mg, 0.30 mmol) in DCM (5 mL) was added TFA (1.5 mL) at 0° C., the solution was stirred at RT for 2 h. The suspension was concentrated to give crude (S)-5-(aminomethyl)-2-(2,7-dioxoazepan-3-yl)isoindoline-1,3-dione (TFA salt) (120 mg), which was used directly for next step without further purification.

To a solution of (S)-5-(aminomethyl)-2-(2,7-dioxoazepan-3-yl)isoindoline-1,3-dione (TFA salt) (120 mg, 0.28 mmol) dissolved in THF (4 mL) was added TEA (45 mg, 0.43 mmol) and the suspension was stirred at RT, then 2-chloro-4-isocyanato-1-methylbenzene (58 mg, 0.35 mmol) was added into the mixture and stirred at RT for 2 h. The mixture was purified by silica gel chromatography eluting with petroleum ether/EA from 50% to 100% to give Compound 27 (70 mg, 52%) as a white solid. MS (ESI) m/z 469.1 [M+H]$^+$. $^1$H NMR (400 MHz, DMSO-d$_6$) δ 10.84 (s, 1H), 8.84 (s, 1H), 7.90-7.88 (m, 1H), 7.82-7.79 (m, 2H), 7.65-7.64 (m, 1H), 7.19-7.13 (m, 2H), 6.93-6.90 (m, 1H), 5.24-5.20 (m, 1H), 4.46 (d, J=6 Hz, 2H), 3.18-3.09 (m, 1H), 2.69-2.63 (m, 1H), 2.55-2.50 (m, 1H), 2.23 (s, 3H), 2.14-2.07 (m, 1H) 1.98-1.85 (m, 2H).

Pharmaceutical Compositions
Parenteral Pharmaceutical Composition

To prepare a parenteral pharmaceutical composition suitable for administration by injection (subcutaneous, intravenous, or the like), 0.1 mg to 100 mg of a water-soluble salt/soluble material itself/solubilized complex of a compound of a preferred embodiment is dissolved in sterile water and then mixed with 10 mL of 0.9% sterile saline. The mixture is incorporated into a dosage unit form suitable for administration by injection.

Injectable Pharmaceutical Composition

To prepare an injectable formulation, 0.1 mg to 100 mg of a compound of Formula I, 2.0 mL of sodium acetate buffer solution (0.4 M), HCl (1 N) or NaOH (1 M) (q.s. to suitable pH), water (distilled, sterile) (q.s. to 20 mL) are mixed. All of the above ingredients, except water, are combined and stirred and if necessary, with slight heating if necessary. A sufficient quantity of water is then added.

Oral Pharmaceutical Composition

To prepare a pharmaceutical composition for oral delivery, 0.1 mg to 100 mg of a compound of a preferred embodiment is mixed with 750 mg of starch. The mixture is incorporated into an oral dosage unit, such as a hard gelatin capsule, or 0.1 mg to 100 mg of compound is granulated with binder solution such as starch solution along with suitable diluents such as microcrystalline cellulose or like, disintegrants such as croscarmellose sodium, dry the resultant mixture and add lubricant and compress into tablet which is suitable for oral administration.

Sublingual (Hard Lozenge) Pharmaceutical Composition

To prepare a pharmaceutical composition for buccal delivery, such as a hard lozenge, 0.1 mg to 100 mg of a compound of a preferred embodiment is mixed with 420 mg of powdered sugar/mannitol/xylitol or such sugars that provide negative heat of solution to the system, 1.6 mL of light corn syrup, 2.4 mL distilled water, and 0.42 mL mint extract or other flavorants. The mixture is blended and poured into a mold to form a lozenge suitable for buccal administration.

Fast-Disintegrating Sublingual Tablet

A fast-disintegrating sublingual tablet is prepared by mixing 48.5% by weigh of a compound of a preferred embodiment, 20% by weight of microcrystalline cellulose (KG-802), 24.5% by weight of either mannitol or modified dextrose or combination that help dissolve the compressed tablet faster in the mouth, 5% by weight of low-substituted hydroxypropyl cellulose (50 μm), and 2% by weight of magnesium stearate. Tablets are prepared by direct compression (AAPS PharmSciTech. 2006; 7(2):E41). The total weight of the compressed tablets is maintained at 150 mg. The formulation is prepared by mixing the amount of the compound of a preferred embodiment with the total quantity of microcrystalline cellulose (MCC) and mannitol/modified dextrose or combination, and two-thirds of the quantity of low-substituted hydroxypropyl cellulose (L-HPC) by using a three dimensional manual mixer (Inversina®, Bioengineering AG, Switzerland) for 4.5 minutes. All of the magnesium stearate (MS) and the remaining one-third of the quantity of L-HPC are added 30 seconds before the end of mixing.

Inhalation Pharmaceutical Composition

To prepare a pharmaceutical composition for inhalation delivery, 0.1 mg to 100 mg of a compound of a preferred embodiment is mixed with 50 mg of anhydrous citric acid and 100 mL of 0.9% sodium chloride solution. The mixture is incorporated into an inhalation delivery unit, such as a nebulizer, which is suitable for inhalation administration.

Nebulizer Suspension Pharmaceutical Composition

In another embodiment, a compound of a preferred embodiment (0.1 mg to 100 mg) is suspended in sterile water (100 mL); Span 85 (1 g) is added followed by addition of dextrose (5.5 g) and ascorbic acid (10 mg). Benzalkonium chloride (3 mL of a 1:750 aqueous solution) is added and the pH is adjusted to 7 with phosphate buffer. The suspension is packaged in sterile nebulizers.

Transdermal Patch Pharmaceutical Composition

To prepare a pharmaceutical composition for transdermal delivery, 0.1 mg to 100 mg of a compound of a preferred embodiment is embedded in, or deposited on, a patch with a single adhesive face. The patch is then attached to the skin via the adhesive face for transdermal administration.

Topical Gel Pharmaceutical Composition

To prepare a pharmaceutical topical gel composition, 0.1 mg to 100 mg of a compound of a preferred embodiment is mixed with 1.75 g of hydroxypropyl cellulose, 10 mL of propylene glycol, 10 mL of isopropyl myristate and 100 mL of purified alcohol USP. The gel mixture is then incorporated into containers, such as tubes, which are suitable for topical administration.

Ophthalmic Solution

To prepare a pharmaceutical ophthalmic solution composition, 0.1 mg to 100 mg of a compound of a preferred embodiment is mixed with 0.9 g of NaCl in 100 mL of purified water and filtered using a 0.2 micron filter. The isotonic solution is then incorporated into ophthalmic delivery units, such as eye drop containers, which are suitable for ophthalmic administration.

Nasal Spray Solution

To prepare a pharmaceutical nasal spray solution, 0.1 mg to 100 mg of a compound of a preferred embodiment is mixed with 30 mL of a 0.05M phosphate buffer solution (pH 4.4). The solution is placed in a nasal administrator designed to deliver 100 μl of spray for each application.

Cell-Based Assays

Either frozen primary blood mononuclear cells (PBMCs) or frozen CD14+ mobilized peripheral blood monocytes were purchased from AllCells (PB003F, Normal Peripheral Blood MNC (Alameda, Calif.)). Cells were quick thawed, washed 1-time with RPMI-1640 (10% FBS/1% Pen-Strep) and plated in 96 well plates at 200,000 cells per well. Cells were pretreated with DMSO only, pomalidomide or the indicated compounds for 1 h and then induced with 100 ng/mL lipopolysaccharide (LPS) for 18-24 h. The supernatant was analyzed for IL-1 beta, IL-6, and TNF-alpha, using Meso Scale assay according to manufacturer's protocol. The negative control wells were treated with DMSO.

For the IL-2 analysis, 96 well plates were precoated with 1 μg/mL anti-human CD3 antibody (OKT3, eBioscience Inc., San Diego, Calif.). After washing with PBS, compounds were added (50 μL/well) followed by PBMCs diluted at 3-4 million cells/mL (150 μL/well). Plates were incubated for 24 h and the supernatants collected for Mesoscale IL-2 analysis.

Figure 2:
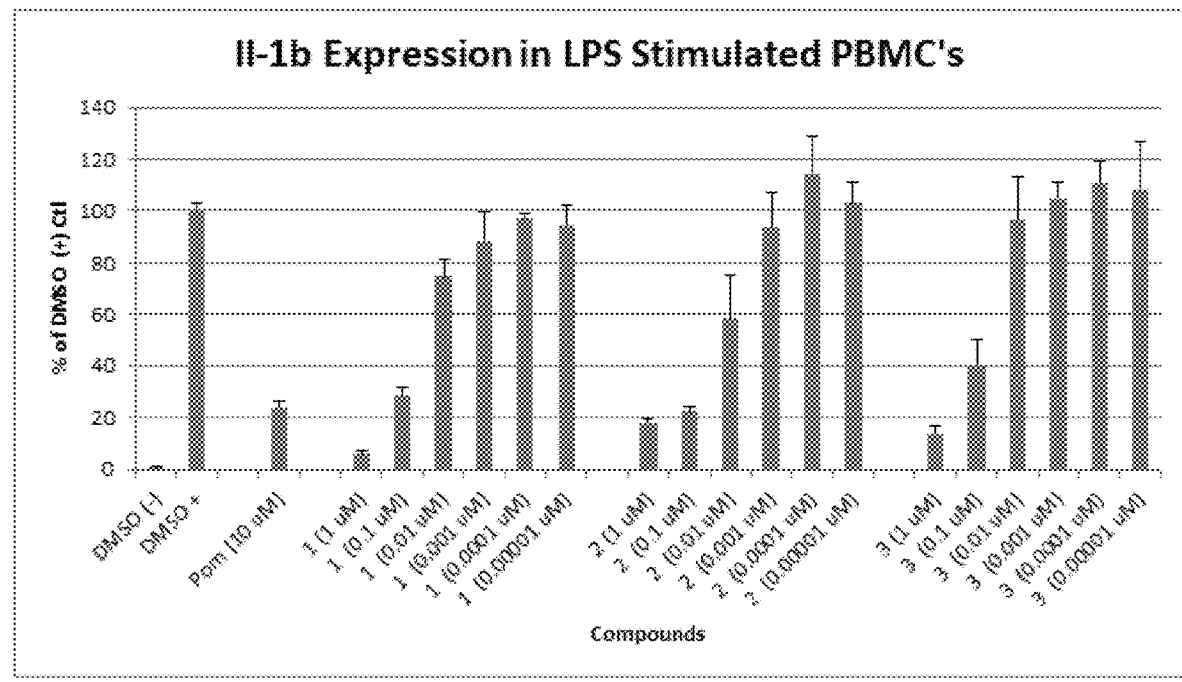
FIG. 2 represents the activity against IL-1-beta in CD14 monocytes, plated in 96 well plates and pretreated with Compounds 1, 2, or 3, or pomalidomide, for 1 h and then induced with 100 ng/mL LPS for 18-24 h. Cytokines were measured according to MesoScale protocol. Negative control wells were treated with DMSO. Compound activity was measured as a percentage of LPS-induced activity.
Figure 3:
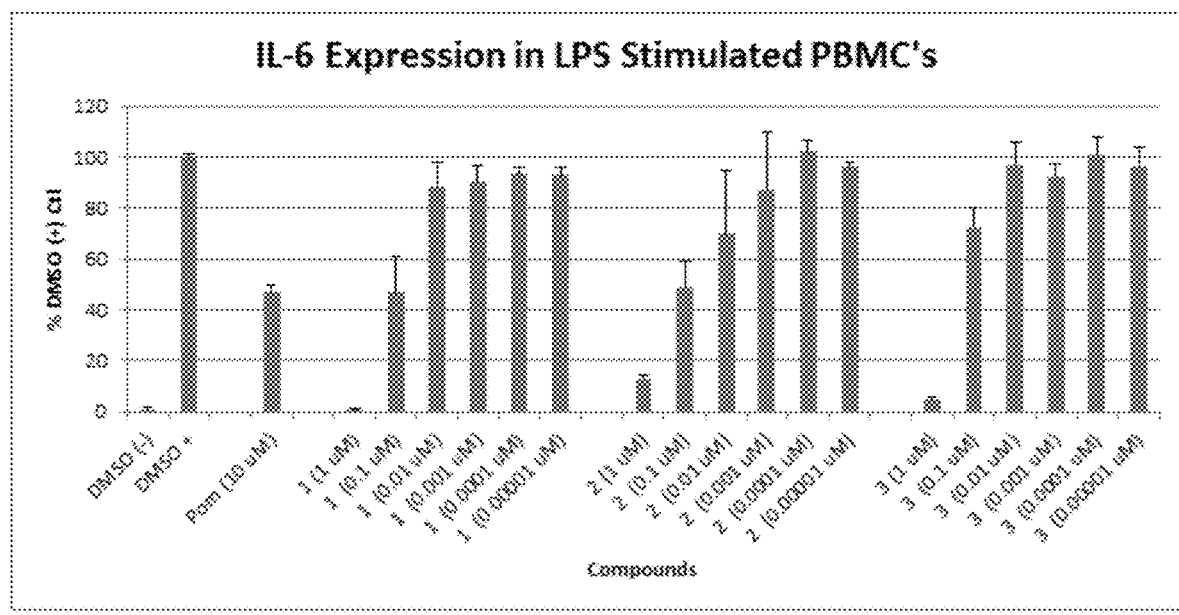
FIG. 3 represents the activity against IL-6 in CD14, monocytes, plated in 96 well plates and pretreated with Compounds 1, 2, or 3, or pomalidomide, for 1 h and then induced with 100 ng/mL LPS for 18-24 h. Cytokines were measured according to MesoScale protocol. Negative control wells were treated with DMSO. Cells were treated with compound (at the indicated concentrations) or 10 µM pomalidomide. Compound activity was measured as a percentage of LPS-induced activity.
Figure 4:
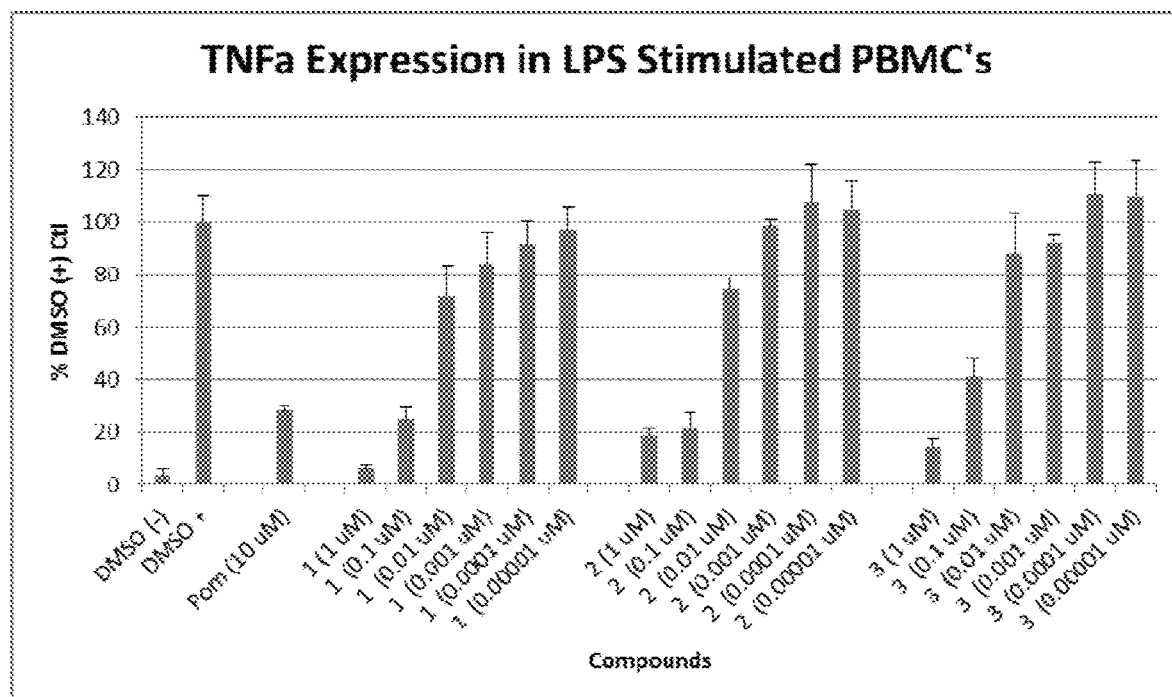
FIG. 4 represents the activity against TNF-alpha in CD14, monocytes, plated in 96 well plates and pretreated with Compounds 1, 2, or 3, or pomalidomide, for 1 h and then induced with 100 ng/mL LPS for 18-24 h. Cytokines were measured according to MesoScale protocol. The negative control wells were treated with DMSO. Cells were treated with compound (at the indicated concentrations) or 10 µM pomalidomide. Compound activity was measured as a percentage of LPS-induced activity.

Compound activity is measured as fold difference from the DMSO control. IL-1-beta activity is shown in FIG. 2; IL-6 activity is shown in FIG. 3; and TNF-alpha activity is shown in FIG. 4. Compounds 1, 2, and 3 each reduced expression of IL-1-b in LPS-stimulated PBMCs by over 80% at 1 uM, relative to a just under 80% reduction with pomalidomide at 10 μM (FIG. 2). Compounds 1, 2, and 3 each also reduced IL-6 levels in LPS-stimulated PBMCs by over 90% at 1 uM, relative to a just under 60% reduction with pomalidomide at 10 μM (FIG. 3). Compounds 1, 2, and 3 each also reduced expression of TNF-α in LPS-stimulated PBMCs by 90-95%, relative to about a 30% reduction with pomalidomide at 10 μM (FIG. 4).

Cell Viability Assay

Molm-13 cells were cultivated in RPMI-1640 (10% FBS/1% pen-strep) and were plated in white walled 96-well plates at 20,000 cells/well. H1048 cells were cultured in DMEM:F12 media supplemented with 5% fetal bovine serum, insulin, transferrin, sodium selenite, hydrocortisone, estradiol, penicillin and streptomycin, and were plated in white walled 96-well plates at 20,000 cells/well.

Cells were treated with compound at the indicated concentration or DMSO (control) and the cultures were incubated for 3 days at 37° C. and 5% $CO_2$. Following the incubation period, 100 μL of CellTiterGlow (CTG) reagent (CellTiter-Glo® Luminescent Cell Viability Assay, Promega (Madison, Wis.)) was added to each well. Following a 10 min incubation with shaking, luminescence was measured using a Victor Wallac Luminometer.

Figure 5:
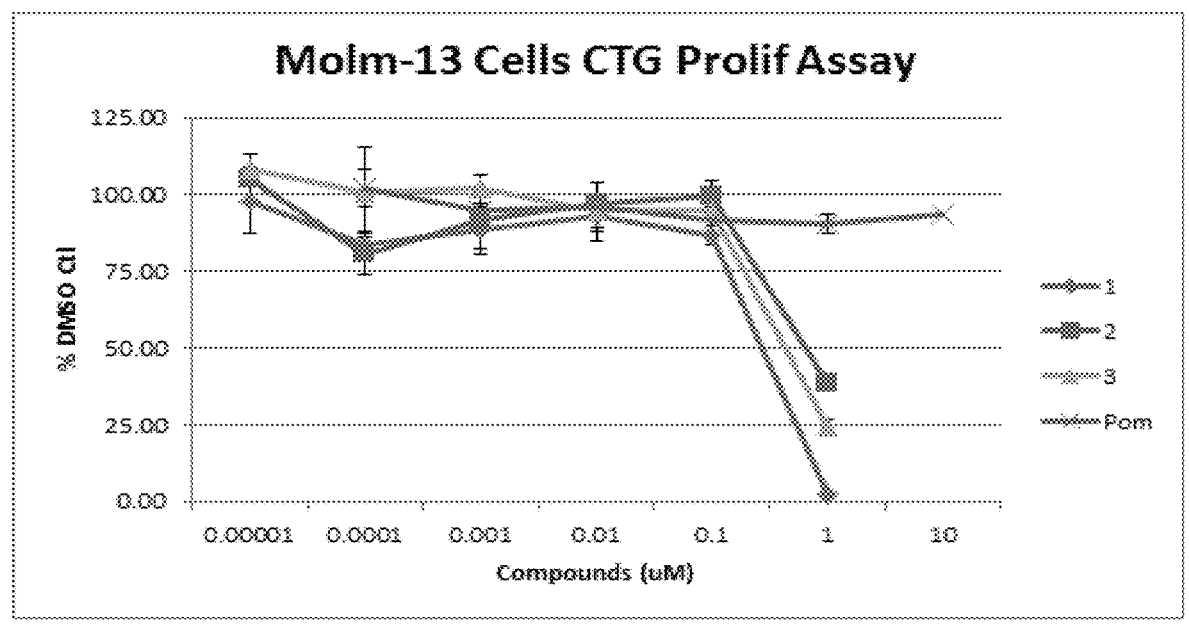
FIG. 5 represents antiproliferative activity in Molm-13 cells. The cells were incubated with Compound 1, 2, or 3 (at the indicated concentration), DMSO, or pomalidomide. Compound activity was measured based on the signal from remaining viable cells.

Compounds 1, 2 and 3 reduced cell viability in Molm-13 cells at 1 μM, whereas pomalidomide had no effect on cellular viability even at 10 μM (FIG. 5). $IC_{50}$ values for Compounds 1, 2, and 3 are approximately 450 nM, 800 nM, 1 μM, respectively.

Additional data for MOLM-13 and H1048 cell viability are shown in Tables A and B, below.

TABLE A

MOLM-13 Cell Viability

| Compound No. | Concentration (μM) | % Cell Viability |
|---|---|---|
| 1 | 0.3 | 50 |
| 2 | 0.4 | 50 |
| 3 | 0.6 | 50 |
| 4 | >1 | 50 |
| 5 | 0.6 | 50 |
| 6 | 0.7 | 50 |
| 7 | 1 | 70 |
| 8 | 0.5 | 48 |
| 9 | 10 | 99 |
| 10 | 10 | 96 |
| 11 | 10 | 99 |
| 12 | 10 | 11 |
| 13 | 10 | 84 |
| 14 | 10 | 28 |
| 15 | 10 | 84 |
| 16 | 0.5 | 70 |
| 17 | 10 | 91 |
| 18 | 0.5 | 68 |
| 19 | 1 | 79 |
| 20 | 10 | 23 |
| 21 | 10 | 25 |
| 22 | 1 | 2.45 |
| 23 | 10 | 96 |
| 24 | 10 | 98 |
| 25 | 10 | 96 |
| 26 | 1 | 79 |
| 27 | 10 | 89 |

TABLE B

H1048 Cell Viability

| Compound No. | Concentration | % Cell Viability |
|---|---|---|
| 1 | 1 μM | 8.39 |
| 2 | 1 μM | 28.32 |
| 3 | 1 μM | 47.12 |
| 4 | 1 μM | 102.64 |
| 5 | 1 μM | 27.27 |
| 6 | 1 μM | 45.73 |
| 7 | 1 μM | 44.13 |
| 8 | 1 μM | 17.39 |
| 9 | 1 μM | 57.12 |
| 10 | 1 μM | 82.08 |
| 11 | 1 μM | 70.78 |
| 12 | 1 μM | — |
| 13 | 1 μM | 97.79 |
| 14 | 1 μM | 101.19 |
| 15 | 1 μM | 93.34 |
| 16 | 1 μM | 7.66 |
| 17 | 1 μM | 95.50 |
| 18 | 1 μM | 14.22 |
| 19 | 1 μM | 8.26 |
| 20 | 1 μM | 98.55 |
| 21 | 1 μM | 95.52 |
| 22 | 1 μM | 11.50 |
| 25 | 1 μM | 88.08 |
| 26 | 1 μM | 46.37 |
| 27 | 1 μM | 100.73 |
| 1 | 10 μM | 3.51 |
| 2 | 10 μM | 4.93 |
| 3 | 10 μM | 6.25 |
| 4 | 10 μM | 97.45 |
| 5 | 10 μM | 2.36 |
| 6 | 10 μM | 5.42 |
| 7 | 10 μM | 7.25 |
| 8 | 10 μM | 4.40 |
| 9 | 10 μM | 7.27 |
| 10 | 10 μM | 21.53 |
| 11 | 10 μM | 11.55 |
| 12 | 10 μM | — |

TABLE B-continued

H1048 Cell Viability

| Compound No. | Concentration | % Cell Viability |
|---|---|---|
| 13 | 10 μM | 44.22 |
| 14 | 10 μM | 56.20 |
| 15 | 10 μM | 35.01 |
| 16 | 10 μM | 3.93 |
| 17 | 10 μM | 34.86 |
| 18 | 10 μM | 4.28 |
| 19 | 10 μM | 3.09 |
| 20 | 10 μM | 96.18 |
| 21 | 10 μM | 45.31 |
| 22 | 10 μM | 4.04 |
| 23 | 10 μM | 25.11 |
| 24 | 10 μM | 2.81 |
| 25 | 10 μM | 26.57 |
| 26 | 10 μM | 4.54 |
| 27 | 10 μM | 28.16 |

Western Blot Analysis

Western Blot Protocol: Cell lines were grown in RPMI 1640 supplemented with streptomycin, penicillin and 10% fetal bovine serum.

Jurkat cells were cultured at approximately $10^6$ cells per mL, DMSO or the indicated compound was added to the cells and allowed to incubate for 6-8 h. Whole cell extract was prepared with RIPA buffer according to manufacturer's protocol (Pierce (Dallas, Tex.)). Briefly, ~$2 \times 10^6$ cells were washed once in PBS, the cell pellet was resuspended in RIPA buffer and allowed to incubate for 15 min on ice. Cell debris was removed by centrifugation and the cleared whole cell lysate was transferred to a new tube for further analysis.

For western blot analysis, whole cell extracts were separated on 4-12% SDS-polyacrylamide gels, transferred to nitrocellulose and probed with the indicated primary antibodies. Membranes were subsequently washed and probed with the appropriate horseradish peroxidase (HRP)-conjugated secondary antibody. Membranes were subsequently washed and probed with the appropriate IRDye secondary antibodies (LI-COR). The signal was detected using the Odyssey Imaging System (LI-COR).

The decrease in GSPT1 protein levels after exposure to certain compounds is shown in Tables C and D, below.

TABLE C

GSPT1 Levels at 100 nM Compound Concentration

| Compound No. | GSPT1 Protein Levels |
|---|---|
| DMSO | 100.00 |
| 1 | 28.62 |
| 2 | 134.18 |
| 3 | 95.50 |
| 4 | 213.59 |
| 5 | 80.22 |
| 6 | 113.33 |
| 7 | 83.28 |
| 8 | 52.58 |
| 9 | 128.33 |
| 10 | 83.28 |
| 11 | 136.97 |
| 12 | — |
| 13 | 95.92 |
| 14 | 145.06 |
| 15 | 167.24 |
| 16 | 59.44 |
| 17 | 131.10 |
| 18 | 69.73 |
| 19 | — |
| 20 | 125.71 |
| 21 | 125.58 |
| 22 | 22.10 |
| 23 | 147.44 |
| 24 | 122.15 |
| 25 | 98.14 |
| 26 | 61.61 |
| 27 | 51.35 |

TABLE D

GSPT1 Levels at 1 uM Compound Concentration

| Compound No. | GSPT1 Protein Levels |
|---|---|
| DMSO | 100.00 |
| 1 | 3.63 |
| 2 | 23.01 |
| 3 | 46.81 |
| 4 | 115.50 |
| 5 | 15.65 |
| 6 | 37.86 |
| 7 | 18.47 |
| 8 | 14.93 |
| 9 | 32.10 |
| 10 | 49.27 |
| 11 | 55.98 |
| 12 | 18.56 |
| 13 | 46.22 |
| 14 | 82.76 |
| 15 | 110.71 |
| 16 | 39.27 |
| 17 | 80.46 |
| 18 | 20.23 |
| 19 | 26.77 |
| 20 | 160.08 |
| 21 | 134.34 |
| 22 | 5.56 |
| 23 | 104.70 |
| 24 | 126.08 |
| 25 | 63.54 |
| 26 | 20.79 |
| 27 | 23.75 |

The percent inhibition of IL-1β, IL-6, and TNF-α, and the fold change in IL-2 activity, after exposure to certain compounds is shown in Table E, below.

TABLE E

Change in IL-1β, IL-6, TNF-α, and IL-2 Activity

| Compound No. | Concentration (μM) | % Inhibition IL-1β | % Inhibition IL-6 | % Inhibition TNF-α | Fold Change IL-2 |
|---|---|---|---|---|---|
| 1 | 0.1 | 70 | 55 | 75 | 1.4 |
| 2 | 0.1 | 78 | 51 | 79 | 1.4 |
| 3 | 0.1 | 59 | 27 | 59 | 1.4 |
| 4 | 1 | 39 | 33 | 44 | 1.5 |
| 5 | 1 | 90 | 99 | 92 | 1.3 |
| 6 | 1 | 64 | 77 | 65 | 1.3 |
| 7 | 1 | 56 | 73 | 59 | 1.0 |
| 8 | 1 | 78 | 95 | 84 | 0.9 |
| 9 | 1 | 61 | 63 | 64 | 1.8 |

TABLE E-continued

Change in IL-1β, IL-6, TNF-α, and IL-2 Activity

| Compound No. | Concentration (μM) | % Inhibition IL-1β | % Inhibition IL-6 | % Inhibition TNF-α | Fold Change IL-2 |
|---|---|---|---|---|---|
| 10 | 1 | 68 | 67 | 67 | 1.5 |
| 11 | 1 | 0 | 5 | 12 | 0.6 |
| 12 | 1 | 75 | 90 | 59 | 1.5 |
| 13 | 1 | 77 | 85 | 53 | 2.6 |
| 14 | 0.1 | 0 | 0 | 0 | 0.9 |
| 15 | 0.1 | 0 | 0 | 0 | 1.0 |
| 16 | 0.1 | 72 | 72 | 78 | 1.7 |
| 17 | 0.1 | 19 | 0 | 18 | 1.3 |
| 18 | 0.1 | 53 | 41 | 48 | 1.5 |
| 19 | 0.1 | 37 | 17 | 33 | 1.2 |
| 20 | 0.1 | 12 | 7 | 11 | 1.1 |
| 21 | 0.1 | 27 | 18 | 20 | 0.9 |
| 22 | 0.1 | 82 | 58 | 74 | 2.0 |
| 23 | 0.1 | 21 | 0 | 25 | 0.8 |
| 24 | 0.1 | 26 | 0 | 42 | 0.9 |
| 25 | 0.1 | 38 | 12 | 36 | 1.4 |
| 26 | 0.1 | 1 | 0 | 3 | 0.8 |
| 27 | 0.1 | 9 | 0 | 19 | 1.1 |

The following antibodies were used in these studies:
Casein kinase 1 alpha: Abcam, catalogue number 108296 (Cambridge, UK)
Ikaros: Cell Signaling, catalogue number 9034 (Danvers, Mass.)
Actin: Cell Signaling, 8H10D10 (Danvers, Mass.)
GSPT1 (Rabbit): Abcam, ab126090 (Cambridge, Eng.)
GSPT1 (Goat): Santa Cruz Biotechnology, sc-6477 (Santa Cruz, Calif.)
IRDye 680RD Goat anti-rabbit antibody: LI-COR, 926-68071 (Lincoln, Nebr.)
IRDye 800CW Goat anti-mouse antibody: LI-COR, 926-32210 (Lincoln, Nebr.)

While the disclosure has been illustrated and described in detail in the drawings and foregoing description, such illustration and description are to be considered illustrative or exemplary and not restrictive. The disclosure is not limited to the disclosed embodiments. Variations to the disclosed embodiments can be understood and effected by those skilled in the art in practicing the claimed disclosure, from a study of the drawings, the disclosure and the appended claims.

All references cited herein are incorporated herein by reference in their entirety. To the extent publications and patents or patent applications incorporated by reference contradict the disclosure contained in the specification, the specification is intended to supersede and/or take precedence over any such contradictory material.

Unless otherwise defined, all terms (including technical and scientific terms) are to be given their ordinary and customary meaning to a person of ordinary skill in the art, and are not to be limited to a special or customized meaning unless expressly so defined herein. It should be noted that the use of particular terminology when describing certain features or aspects of the disclosure should not be taken to imply that the terminology is being re-defined herein to be restricted to include any specific characteristics of the features or aspects of the disclosure with which that terminology is associated.

Where a range of values is provided, it is understood that the upper and lower limit, and each intervening value between the upper and lower limit of the range is encompassed within the embodiments.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof; adjectives such as 'known', 'normal', 'standard', and terms of similar meaning should not be construed as limiting the item described to a given time period or to an item available as of a given time, but instead should be read to encompass known, normal, or standard technologies that may be available or known now or at any time in the future; and use of terms like 'preferably,' 'preferred,' 'desired,' or 'desirable,' and words of similar meaning should not be understood as implying that certain features are critical, essential, or even important to the structure or function of the invention, but instead as merely intended to highlight alternative or additional features that may or may not be utilized in a particular embodiment of the invention.

It will be further understood by those within the art that if a specific number of an introduced claim recitation is intended, such an intent will be explicitly recited in the claim, and in the absence of such recitation no such intent is present. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.).

All numbers expressing quantities of ingredients, reaction conditions, and so forth used in the specification are to be understood as being modified in all instances by the term 'about.' Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

Furthermore, although the foregoing has been described in some detail by way of illustrations and examples for purposes of clarity and understanding, it is apparent to those skilled in the art that certain changes and modifications may be practiced. Therefore, the description and examples should not be construed as limiting the scope of the invention to the specific embodiments and examples described herein, but rather to also cover all modification and alternatives coming with the true scope and spirit of the invention.

What is claimed is:

1. A method of inhibiting GSPT1 activity, comprising contacting a cell with a compound of Formula (I), or a pharmaceutically acceptable salt thereof;

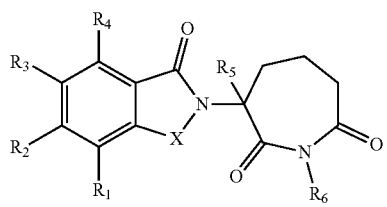
(I)

wherein:
$R_1$, $R_2$, $R_3$, and $R_4$, are each independently selected from the group consisting of H, deuterium, halogen, cyano, nitro, —$NH_2$, —$NHR_7$, $NR_7R_7$, an optionally substituted $C_1$ to $C_6$ alkoxy, an optionally substituted $C_1$ to $C_6$ alkyl,

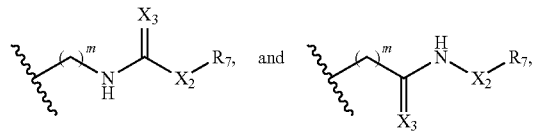

wherein at least one of $R_1$, $R_2$, $R_3$, and $R_4$ is

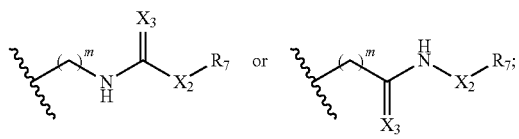

$R_5$ is selected from the group consisting of H, deuterium, fluoro, and an optionally substituted $C_1$ to $C_6$ alkyl;
$R_6$ is selected from the group consisting of H, deuterium, and an optionally substituted $C_1$ to $C_6$ alkyl;
X is selected from the group consisting of $CH_2$ and C=O;
each $X_2$ is independently selected from the group consisting of $(CH_2)_n$, $(CD_2)_n$, $(CF_2)_n$, C=O, NH, N-(an optionally substituted $C_1$ to $C_6$ alkyl), $[(CH_2)_p$—NH—$(CH_2)_q]_t$, and $[(CH_2)_p$—O—$(CH_2)_q]_t$;
each $X_3$ is independently selected from the group consisting of NH, O, and S;
wherein, when any of $R_1$, $R_2$, $R_3$, or $R_4$ is

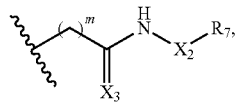

$X_2$ is selected from the group consisting of $(CH_2)_n$, $(CD_2)_n$, C=O, $[(CH_2)_p$—NH—$(CH_2)_q]_t$, and $[(CH_2)_p$—O—$(CH_2)_q]_t$;
each m is independently 1, 2, 3, 4, or 5;
each n is independently 0, 1, 2, 3, 4, 5, 6, 7, 8, 9, or 10;
each p and q is independently 0, 1, 2, 3, 4, 5, or 6;
each t is independently 0, 1, 2, 3, or 4; and
each $R_7$ is independently selected from the group consisting of an optionally substituted $C_3$ to $C_{10}$ cycloalkyl, an optionally substituted $C_6$ to $C_{10}$ aryl, an optionally substituted 5- to 10-membered heteroaryl, an optionally substituted 3- to 10-membered heterocyclyl, and an optionally substituted $C_1$ to $C_{10}$ alkyl.

2. The method of claim 1, wherein $R_1$ is H and $R_2$ is

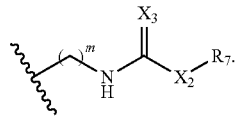

3. The method of claim 2, wherein $X_2$ is selected from the group consisting of NH, $(CH_2)_n$, $[(CH_2)_p$—NH—$(CH_2)_q]_t$, and N—(an optionally substituted $C_1$ to $C_6$ alkyl).

4. The method of claim 2, wherein $R_3$ and $R_4$ are each independently selected from the group consisting of H and halogen.

5. The method of claim 2, wherein each $R_5$ and $R_6$ is H.

6. The method of claim 2, wherein $R_7$ is selected from the group consisting of an optionally substituted $C_3$ to $C_{10}$ cycloalkyl, an optionally substituted $C_6$ to $C_{10}$ aryl, an optionally substituted 5- to 10-membered heteroaryl, and an optionally substituted 3- to 10-membered heterocyclyl.

7. The method compound of claim 6, wherein the phenyl group is substituted with 1 or 2 unsubstituted $C_1$ to $C_6$ alkyl groups and 1 or 2 halogens; or wherein the phenyl group is substituted with 1 unsubstituted $C_1$ to $C_6$ alkyl groups and 1 halogen.

8. The method of claim 2, wherein $R_3$ and R4 are both hydrogen; m is 1; $X_2$ is NH; and $X_3$ is O or S.

9. The method of claim 1, wherein the compound is selected form the group consisting of:

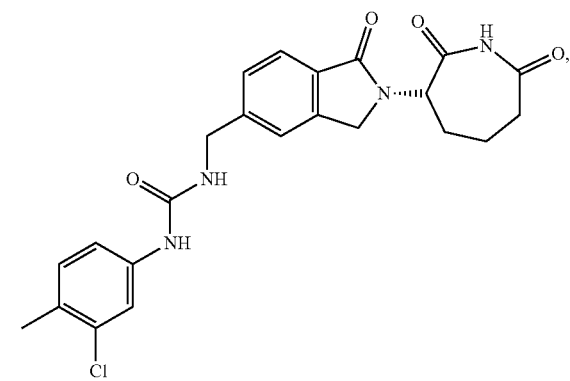

75
-continued
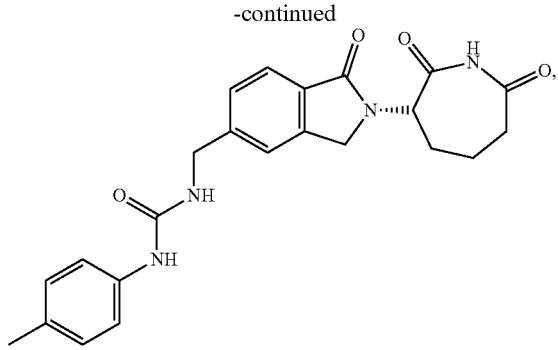
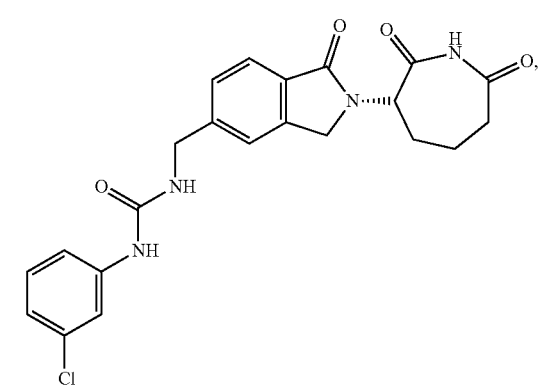
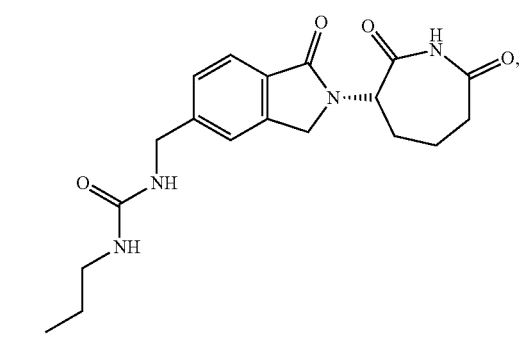
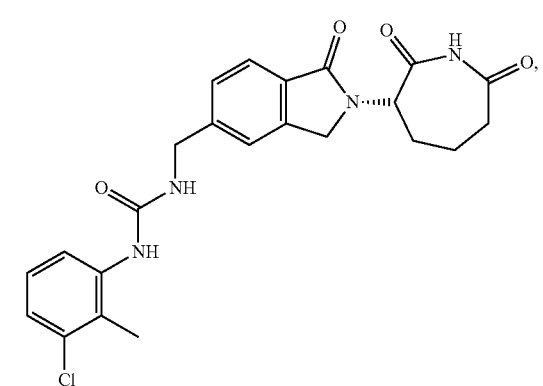
76
-continued
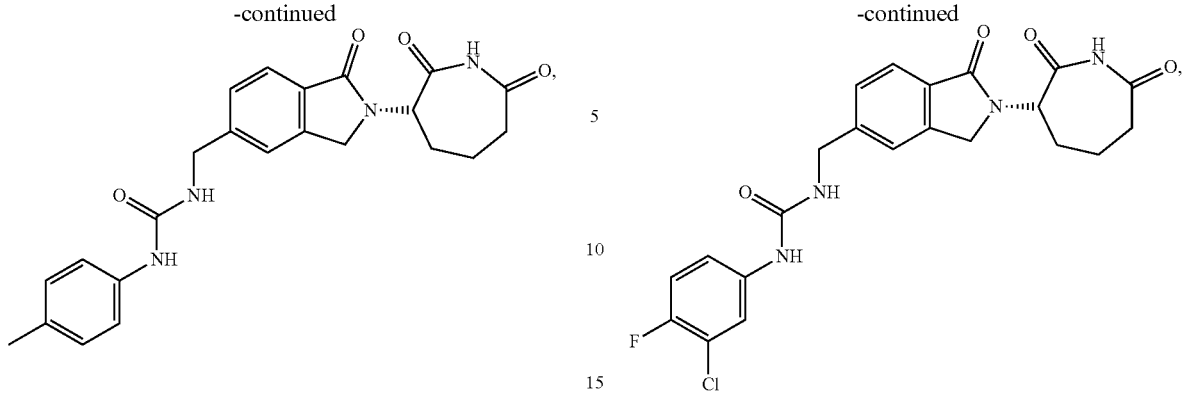
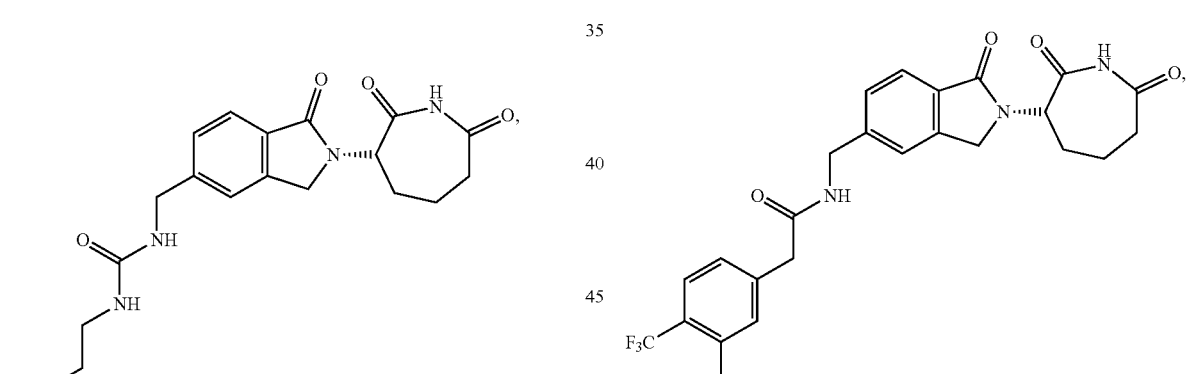
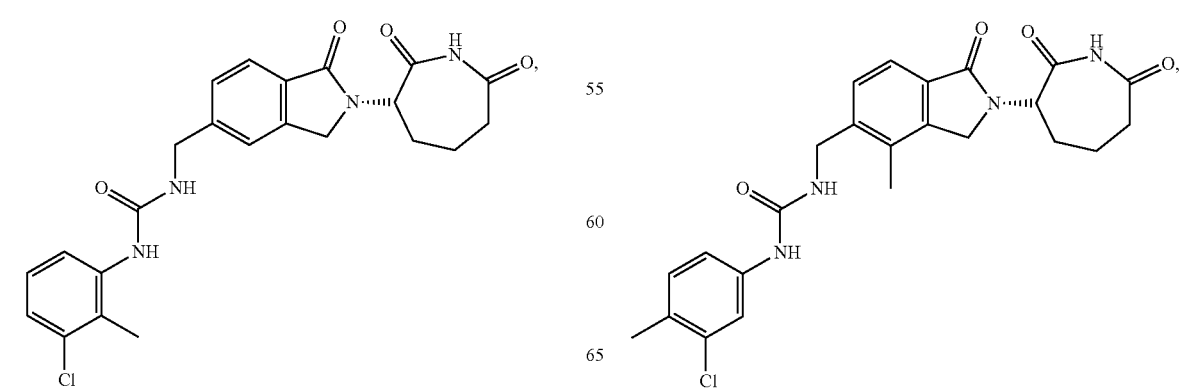
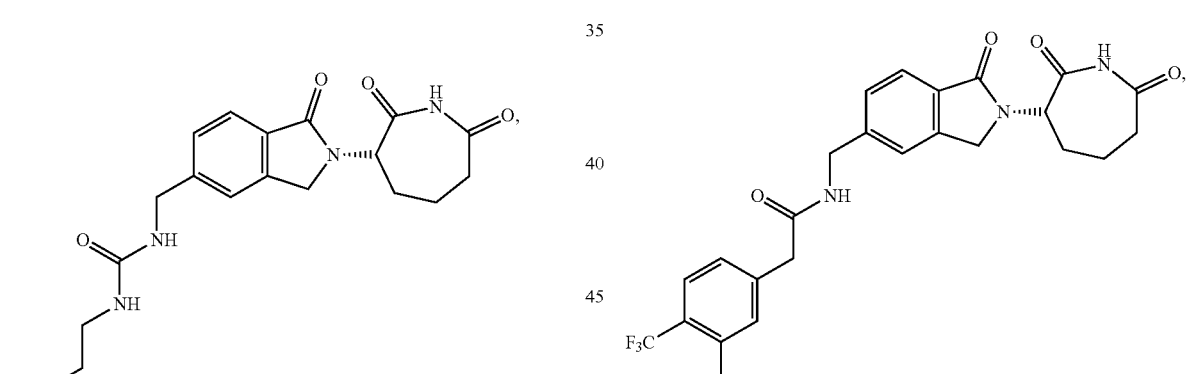

77
-continued
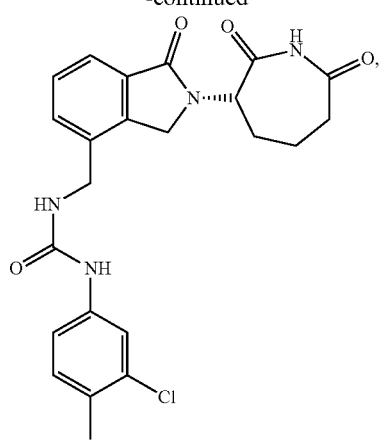
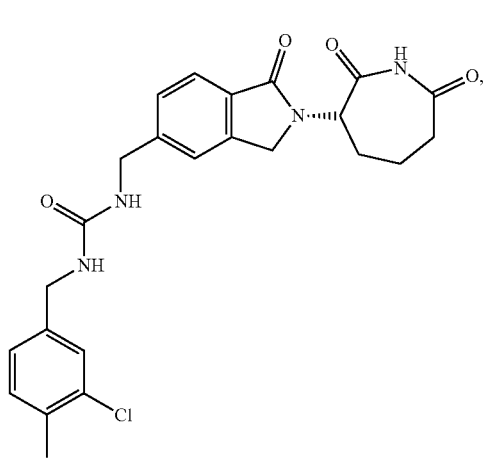
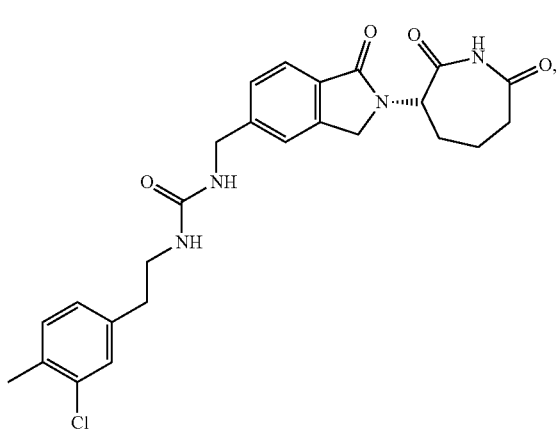
78
-continued
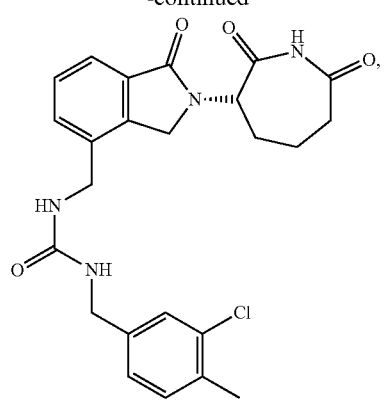
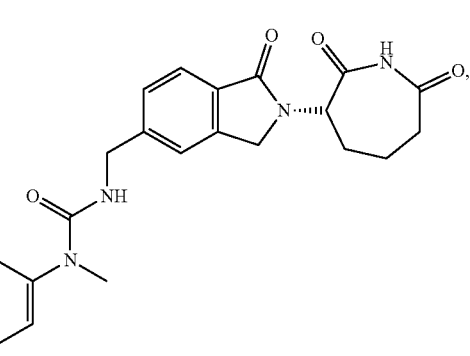
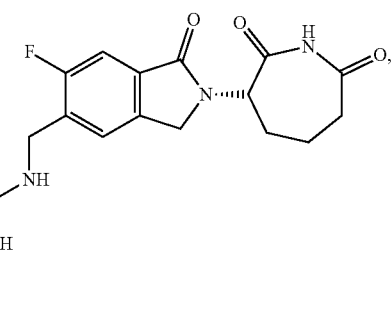

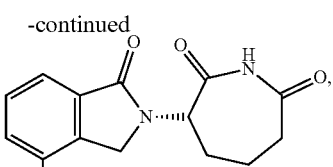
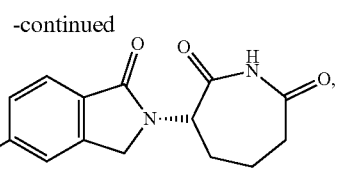
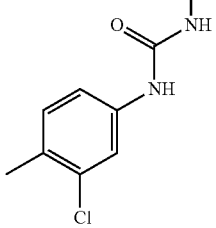
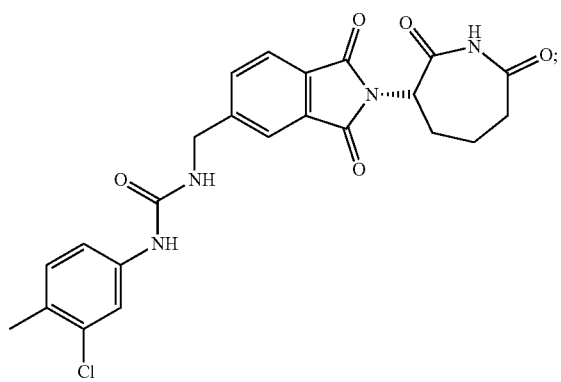
and pharmaceutically acceptable salts thereof.
* * * * *